United States Patent
Jiang et al.

(10) Patent No.: US 9,421,249 B2
(45) Date of Patent: *Aug. 23, 2016

(54) METHODS TO ACTIVATE OR BLOCK THE HLA-E/QA-1 RESTRICTED CD8+ T CELL REGULATORY PATHWAY TO TREAT IMMUNOLOGICAL DISEASE

(71) Applicant: THE TRUSTEES OF COLUMBIA UNIVERSITY IN THE CITY OF NEW YORK, New York, NY (US)

(72) Inventors: Hong Jiang, Fort Lee, NJ (US); Leonard Chess, Scarsdale, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/762,249

(22) Filed: Feb. 7, 2013

(65) Prior Publication Data

US 2013/0209498 A1  Aug. 15, 2013

Related U.S. Application Data

(63) Continuation of application No. 12/583,723, filed on Aug. 24, 2009, which is a continuation-in-part of application No. PCT/US2008/002391, filed on Feb. 22, 2008.

(60) Provisional application No. 61/004,358, filed on Nov. 26, 2007, provisional application No. 60/903,070, filed on Feb. 23, 2007.

(51) Int. Cl.
*C12N 5/00* (2006.01)
*C12N 5/02* (2006.01)
*C12N 5/071* (2010.01)
*A61K 39/00* (2006.01)

(52) U.S. Cl.
CPC ............ *A61K 39/00* (2013.01); *A61K 39/0008* (2013.01); *A61K 2039/5158* (2013.01); *A61K 2039/57* (2013.01); *A61K 2039/6043* (2013.01)

(58) Field of Classification Search
None
See application file for complete search history.

(56) References Cited

U.S. PATENT DOCUMENTS

2003/0171280 A1* 9/2003 Soderstrom ............... 514/12
2005/0208627 A1* 9/2005 Bowdish et al. .......... 435/70.21

OTHER PUBLICATIONS

Pietra et al., "Comparative analysis of NK- or NK-CTL-mediated lysis of immature or mature autologous dendritic cells", Eur. J. Immunol., 2003, pp. 3427-3432.*
Steinman et al., "Exploring dendritic cells to improve vaccine efficacy", The Journal of Clinical Investigation, 2002, p. 1519-1526.*
Hey et al., 2012, J. Cell. Mol. Med. vol. 11: 2611-19.*
Yi et al., 1997, Infect. Immun. vol. 65: 1669-74.*
Itoh et al., 1995, J. Biol. Chem. vol. 270: 13429-35.*

* cited by examiner

*Primary Examiner* — Amy Juedes
(74) *Attorney, Agent, or Firm* — Leason Ellis LLP

(57) ABSTRACT

Methods are provided for inhibiting or enhancing down-regulation of an antigen-activated HLA-E+ T cell by an HLA-E-restricted CD8+ T cell comprising contacting the HLA-E+ T cell and CD8+ T cell with an agent which inhibits or enhances, respectively, binding between (i) T cell receptor (TCR) on the surface of the CD8+ T cell and (ii) a self peptide presented by HLA-E on the surface of the HLA-E+ T cell, thereby inhibiting or enhancing, respectively, down-regulation of the antigen-activated HLA-E+ T cell. Compositions comprising agents which inhibit or enhance/activate, respectively, binding between (i) T cell receptor (TCR) on the surface of a CD8+ T cell and (ii) a self peptide presented by HLA-E on the surface of a HLA-E+ T cell, and assays for identifying such agents, are provided.

2 Claims, 25 Drawing Sheets

Figure 15-A
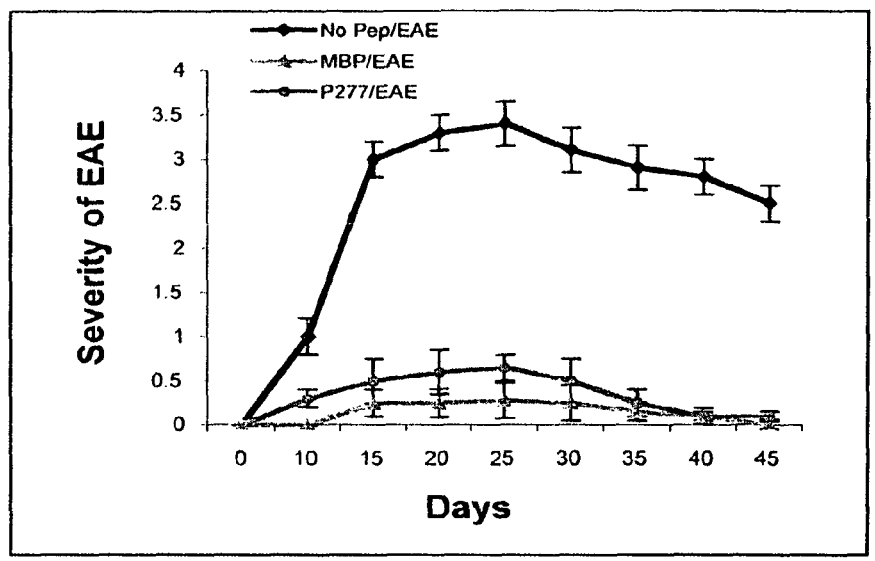
Figure 15-B
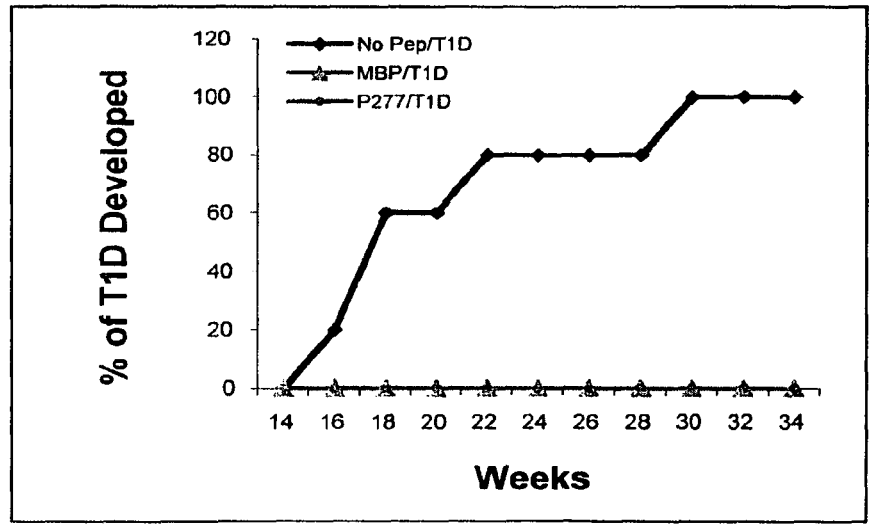

Figure 15-C
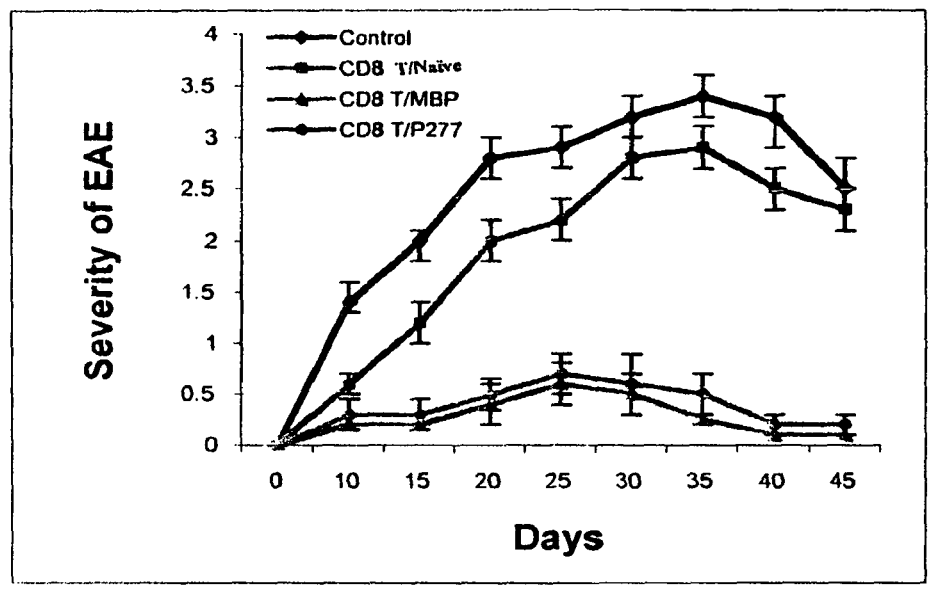
Figure 15-D
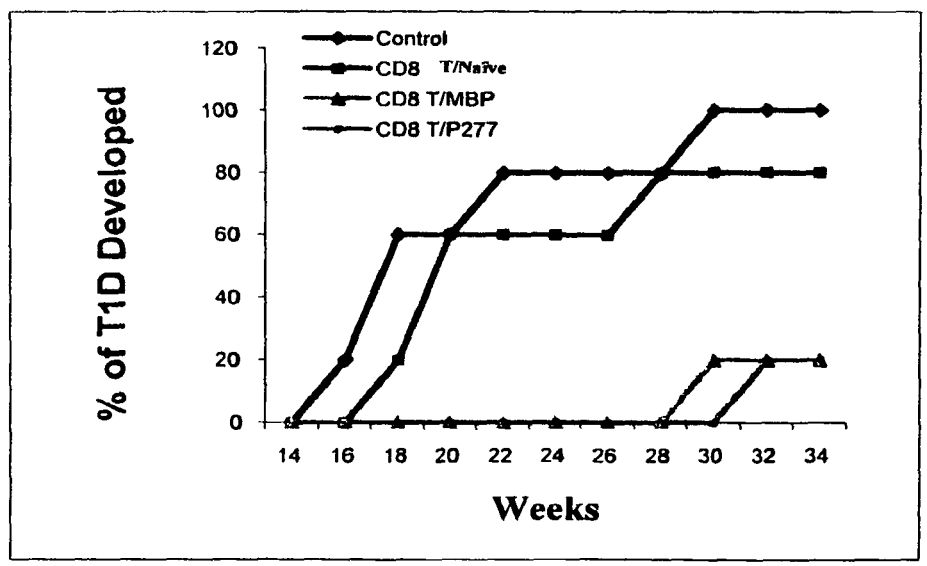

Figure 17-A
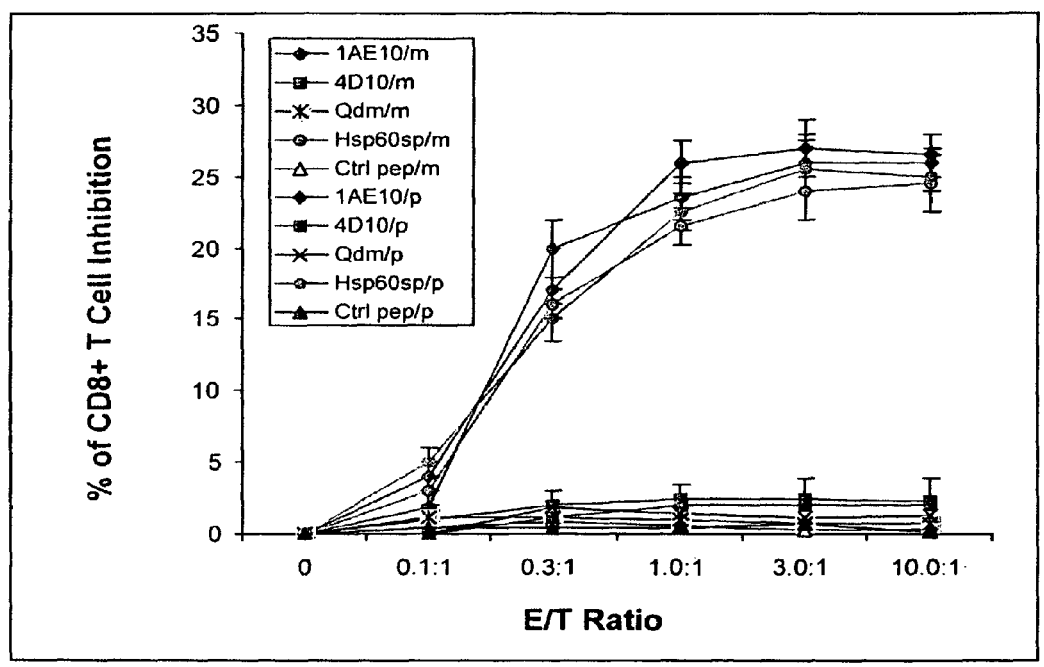

Figure 17-B
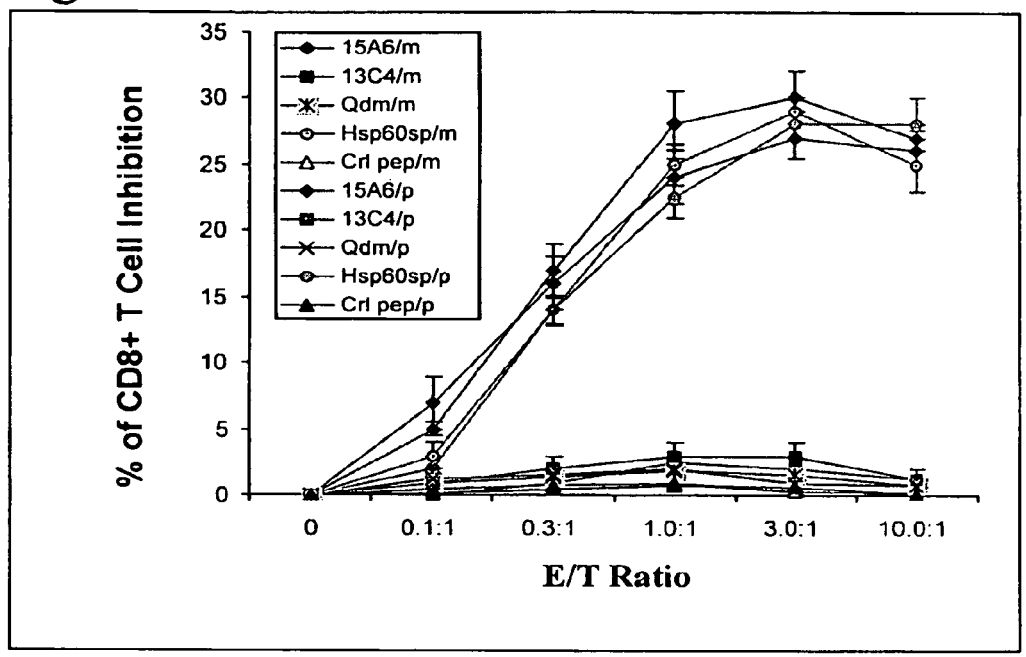

Figure 18-A
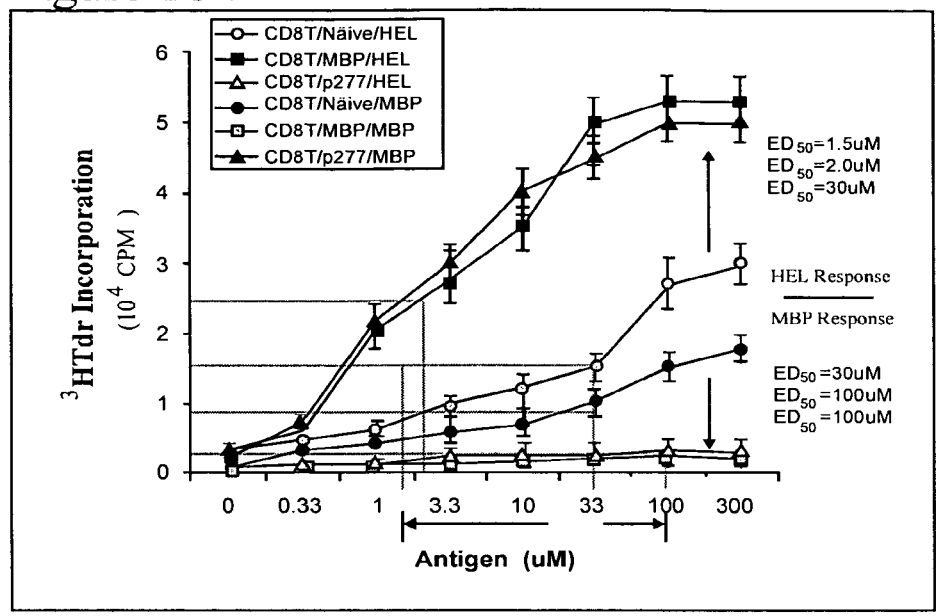
Figure 18-B
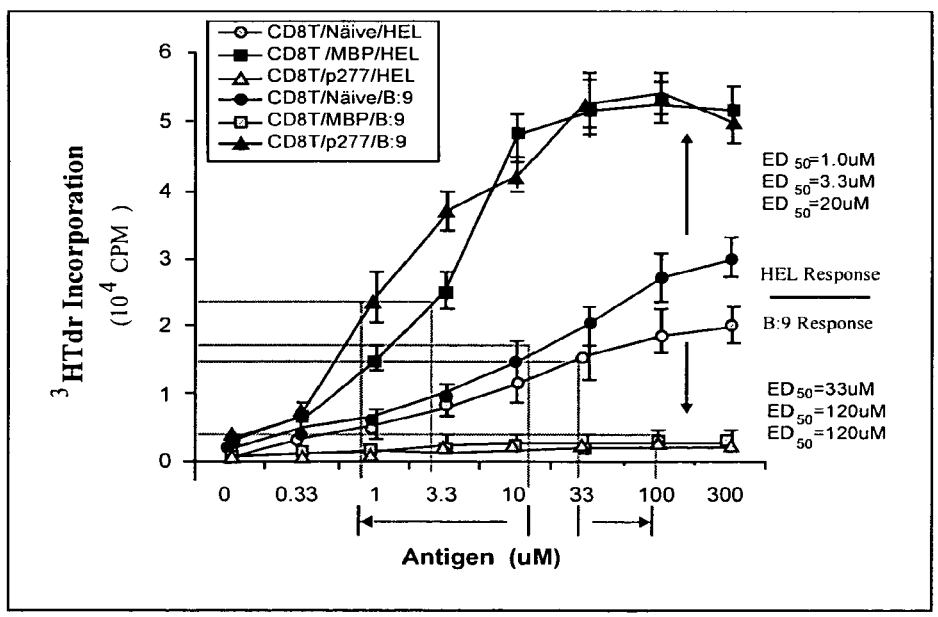

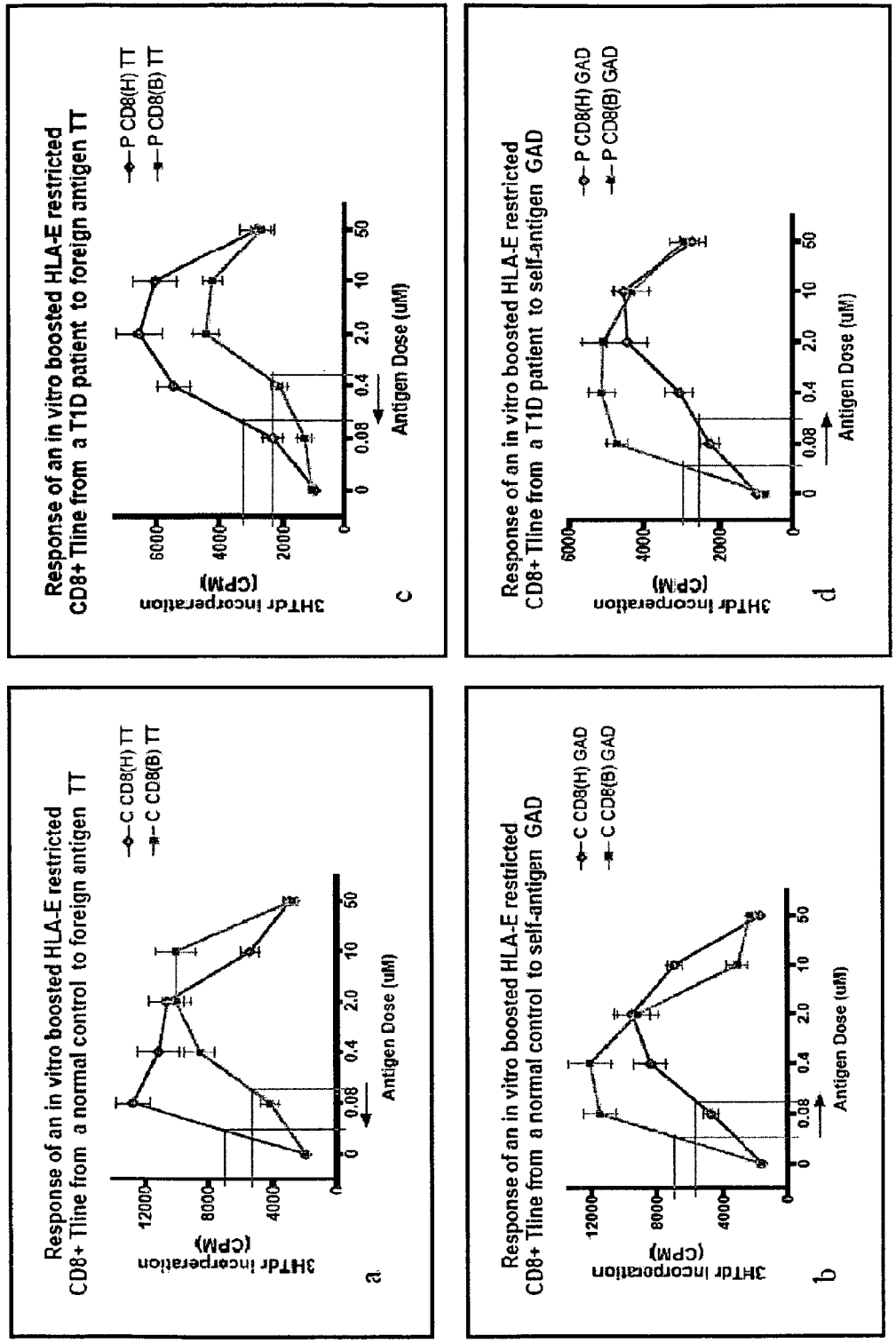
Figs. 21A-D.

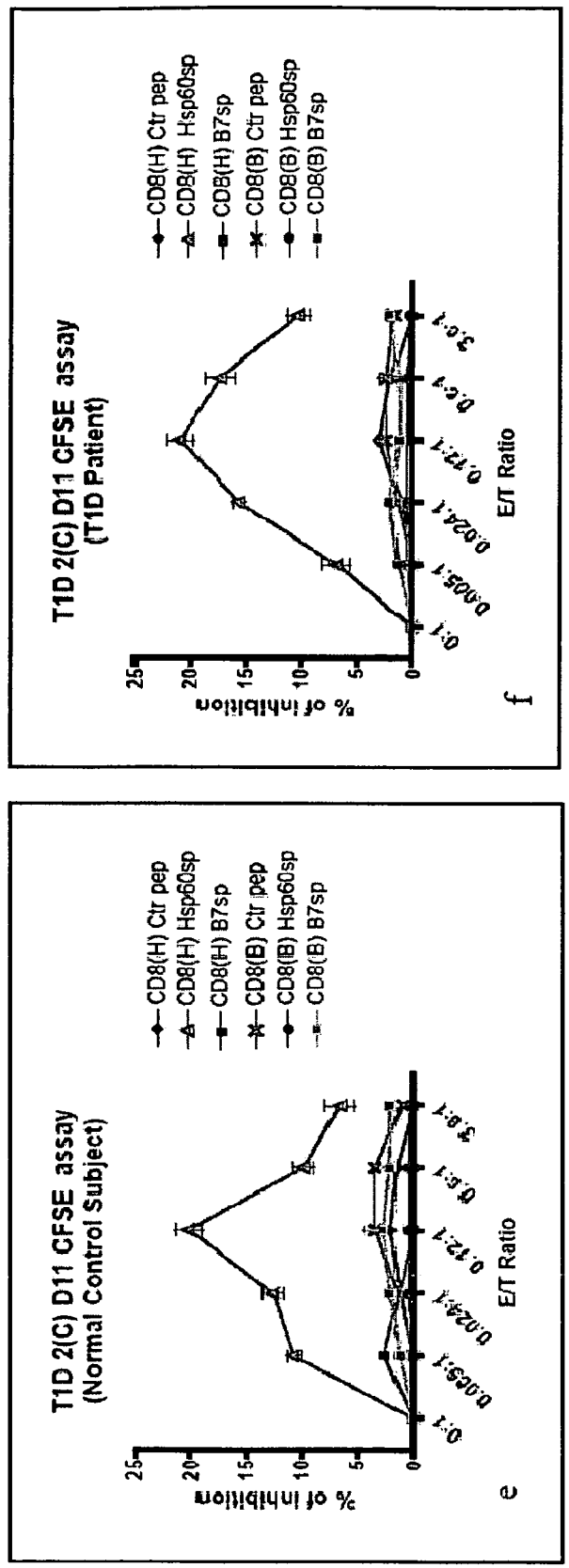
Figs. 21E-F

ID

SEQUENCE LISTING

```
<160> NUMBER OF SEQ ID NOS: 15

<210> SEQ ID NO 1
<211> LENGTH: 9
<212> TYPE: PRT
<213> ORGANISM: Mus musculus

<400> SEQUENCE: 1

Ala Met Ala Pro Arg Thr Leu Leu Leu
1               5

<210> SEQ ID NO 2
<211> LENGTH: 9
<212> TYPE: PRT
<213> ORGANISM: Mus musculus

<400> SEQUENCE: 2

Gln Met Arg Pro Val Ser Arg Ala Leu
1               5

<210> SEQ ID NO 3
<211> LENGTH: 53
<212> TYPE: DNA
<213> ORGANISM: Mus musculus

<400> SEQUENCE: 3
catctagagg atgttgcttc aaatgcgccc ggtcagccgc gctctcagcg cca         53

<210> SEQ ID NO 4
<211> LENGTH: 27
<212> TYPE: DNA
<213> ORGANISM: Artificial Sequence
<220> FEATURE:
<223> OTHER INFORMATION: pimer directed to murine Qa-1

<400> SEQUENCE: 4
cccagagtag cccacactcg ctgcggt                                       27

<210> SEQ ID NO 5
<211> LENGTH: 23
```

```
<212> TYPE: DNA
<213> ORGANISM: Artificial Sequence
<220> FEATURE:
<223> OTHER INFORMATION: primer directed to murine Qa-1

<400> SEQUENCE: 5
cccgaggctc catcctcgga ttt                                         23

<210> SEQ ID NO 6
<211> LENGTH: 26
<212> TYPE: DNA
<213> ORGANISM: Artificial Sequence
<220> FEATURE:
<223> OTHER INFORMATION: primer directed to murine Hsp60

<400> SEQUENCE: 6
gggatggcac caccactgcc actgtt                                      26

<210> SEQ ID NO 7
<211> LENGTH: 21
<212> TYPE: DNA
<213> ORGANISM: Artificial Sequence
<220> FEATURE:
<223> OTHER INFORMATION: primer directed to murine hsp60

<400> SEQUENCE: 7
tccatggtgc tagccatatg c                                           21

<210> SEQ ID NO 8
<211> LENGTH: 37
<212> TYPE: DNA
<213> ORGANISM: Artificial Sequence
<220> FEATURE:
<223> OTHER INFORMATION: primer directed to murine H-2Dd

<400> SEQUENCE: 8
gggcgatggc tccgcgcacg ctgctcctgc tcctgct                          37

<210> SEQ ID NO 9
<211> LENGTH: 30
<212> TYPE: DNA
<213> ORGANISM: Artificial Sequence
<220> FEATURE:
<223> OTHER INFORMATION: primer directed to murine H-2Dd

<400> SEQUENCE: 9
ccgtgttgtc cacgtagccg acttccatgt                                  30

<210> SEQ ID NO 10
<211> LENGTH: 50
<212> TYPE: DNA
<213> ORGANISM: Artificial Sequence
<220> FEATURE:
<223> OTHER INFORMATION: primer directed to murine Qa-1

<400> SEQUENCE: 10
catggtgagg atgttgcttt ttgcccactt gctccagctg ctggtcagcg            50

<210> SEQ ID NO 11
<211> LENGTH: 23
<212> TYPE: DNA
<213> ORGANISM: Artificial Sequence
<220> FEATURE:
<223> OTHER INFORMATION: primer directed to murine Qa-1

<400> SEQUENCE: 11
```

```
agaacatgag catagcatcc ttt                                           23

<210> SEQ ID NO 12
<211> LENGTH: 15
<212> TYPE: PRT
<213> ORGANISM: Mus musculus

<400> SEQUENCE: 12

Ser His Leu Val Glu Ala Leu Tyr Leu Val Cys Gly Glu Arg Gly
1               5                   10                  15

<210> SEQ ID NO 13
<211> LENGTH: 24
<212> TYPE: PRT
<213> ORGANISM: Mus musculus

<400> SEQUENCE: 13

Val Leu Gly Gly Gly Val Ala Leu Leu Arg Val Ile Pro Ala Leu Asp
1               5                   10                  15

Ser Leu Thr Pro Ala Asn Glu Asp
            20

<210> SEQ ID NO 14
<211> LENGTH: 9
<212> TYPE: PRT
<213> ORGANISM: Mus musculus

<400> SEQUENCE: 14

Ala Ser Gly Leu Ala Pro Ser Gly Ala
1               5

<210> SEQ ID NO 15
<211> LENGTH: 9
<212> TYPE: PRT
<213> ORGANISM: Artificial Sequence
<220> FEATURE:
<223> OTHER INFORMATION: chemically synthesized sequence
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = Met or Leu
<220> FEATURE:
<221> NAME/KEY: MISC_FEATURE
<222> LOCATION: (3)..(8)
<223> OTHER INFORMATION: Xaa = any amino acid

<400> SEQUENCE: 15

Xaa Xaa Xaa Xaa Xaa Xaa Xaa Xaa Leu
1               5
```

METHODS TO ACTIVATE OR BLOCK THE HLA-E/QA-1 RESTRICTED CD8+ T CELL REGULATORY PATHWAY TO TREAT IMMUNOLOGICAL DISEASE

This application is continuation of U.S. patent application Ser. No. 12/583,723 (filed Aug. 24, 2009), which is a continuation-in-part of International Application No. PCT/US2008/002391 (filed Feb. 22, 2008), which claims priority to U.S. Provisional Application No. 61/004,358 (filed Nov. 26, 2007) and U.S. Provisional Application No. 60/903,070 (filed Feb. 23, 2007), the contents of all of which are hereby incorporated by reference in their entirety into this application.

The work disclosed herein was made with government support under grant nos. R29 AI39630; RO1 AI44927; PO1 AI39675; RO1 AI065609; and U19 AI46132 from the National Institutes of Health. Accordingly, the U.S. Government has certain rights in this invention.

Throughout this application, various publications are referenced in parentheses by number. Citations for these references may be found at the end of the specification immediately preceding the claims. The disclosures of these publications in their entireties are hereby incorporated by reference into this application to more fully describe the state of the art to which this invention pertains.

INCORPORATION-BY-REFERENCE OF SEQUENCE LISTING

A sequence listing, created on Feb. 6, 2013 as the ASCII text file "4361-002-US-CON-TK1_Seq_Listing.txt" having a file size of 4 kilobytes, is incorporated herein by reference in its entirety.

BACKGROUND

By discriminating self from non-self and controlling the magnitude and class of immune responses, the immune system mounts effective immunity to virtually any foreign antigens but avoids harmful immune responses to self (26 and 27). Immunologically relevant clinical problems often occur due to failure of either process.

How the immune system achieves self/non-self discrimination remains a central issue in Immunology. Understanding the peripheral mechanisms of self/non-self discrimination is the key to the solution of a major contemporary biomedical problem which is how to selectively shut off the unwanted immune response but retain the normal on going immune responses intact.

The immune system accomplishes this task in part by employing cell-surface recognition molecules which when activated by non-self ligands leads to the elaboration of inflammatory molecules and/or the death of adjacent cells. For example, the cells of the innate immune system (NK cells, macrophages, dendritic cells and granulocytes) employ sets of germ-line encoded receptors that specifically recognize conserved molecular patterns found predominately in microorganisms and other non-self pathogens and particles. Thus, recognizing complement regulatory proteins and the toll like or pathogen associated molecular pattern recognition molecules (PAMPs), which define precise differences between foreign pathogens and self cells, by the innate receptors is one approach that the immune system achieves self non-self discrimination (28-30).

In contrast, the adaptive immune system operates predominantly on the somatically generated antigen receptors, which are clonally distributed on T and B cells. These antigen receptors are generated by random processes and the general design of the adaptive immune system is based on clonal selection of lymphocytes expressing receptors with particular antigenic specificities. Although the antigen receptors on T or B cells are capable of distinguishing an almost infinite number of distinctive self and foreign antigens, they cannot determine to which antigen they should and to which antigen they should not respond. As a consequence, the adaptive immune system does not achieve self non-self discrimination by using antigen receptors to recognize the structural differences between self and foreign antigens. In fact the antigen receptors are randomly generated (31 and 32) without knowledge of what is self and what is foreign, and basically without concern for discriminating self from non-self. Indeed, if there is any bias during the ontogeny of the adaptive immune system, it is towards self-recognition.

In the thymus the only peptides available to the developing T cells are self-peptides, and so from the onset T cells are positively and negatively selected on major histocompatibility complex (MHC)/self-peptide complexes. This selection is not based on the distinction between self and foreign antigens but instead is based, solely, on the distinction of the avidity of the interactions between T cell receptors (TCRs) on developing thymocytes and MHC/self-peptide molecules expressed on thymic antigen presenting cells (APCs). Thus, thymocytes expressing TCR of high avidity for MHC/self-peptide complexes undergo apoptosis and are deleted during thymic negative selection (33-35). The T cells which escape the thymic selection have either low or intermediate avidity to self but contain cells capable of reacting to the large universe of foreign antigens with potentially low, intermediate or high avidity.

Based on the "Tunable Activation Thresholds Hypothesis" (TAT hypothesis), recurrent interactions would modify the sensitivity of T cells to ambient signals and thus prevent "resting" lymphocytes from becoming activated and differentiating into effector cells (36 and 37). Although the thymic escapees could thus "ignore" the endogenous self-ligands that are repetitively and constantly presented to them in the periphery, they could be functionally activated by a rapid increase of the level of self-ligands presented, such as "danger signals" (38 and 39) generated during active infections or injuries. It is possible that the pathogenic self-reactive T cells capable of initiating autoimmune disease are included in the pool of intermediate avidity T cells (40 and 41).

Burnet and Medawar demonstrated that introducing a foreign antigen to animals during the neonatal period induces immunological tolerance to that foreign antigen and the animal will not make an immune response to reject the same antigen during adulthood (44,45). Since then understanding the mechanisms of self-tolerance has been a major focus of biomedical research in immunology.

Thymic negative selection, in which thymocytes expressing TCR of high avidity for MHC/self-peptide complexes are deleted (33-35) eliminates "imminent danger" of pathogenic autoimmunity in the periphery and is the major mechanism of self-tolerance. However, thymic negative selection also allows some self-reactive T cells with intermediate avidity to be released into the periphery (40, 45 and 46). These intermediate avidity self-reactive T cells are capable of self-peptide driven proliferation when they encounter self-peptides presented at a sufficient level in the periphery and some may differentiate into potentially pathogenic effector cells (40, 41). To ensure self-tolerance, peripheral regulatory mechanisms have evolved to fine tune the self-reactive TCR repertoire and suppress the clonal expansion of the self-reactive clones with TCRs of avidity that are not sufficiently high to be eliminated intrathymically, but high enough to induce pathogenic auto-immunity. Thus, under normal circumstances, despite the abundance of self-reactive clones in the periphery, clinical auto-immunity is usually well controlled.

The peripheral regulatory mechanisms involve mechanisms intrinsic to the antigen-activation and differentiation of T cells which include antigen-activation-induced cell death (48) and antigen-induced expression of co-stimulatory molecules including CD40L, CD28 and CTLA-4, which dictate whether immunity or anergy ensues (49-52). In addition, the functional activation and differentiation of the CD4+ T cells into the Th1 and Th2 subsets (53-55) or Tr1 and Tr3 subsets (56-58), phenotypically identified, in part, by the elaboration of distinctive cytokines are also considered an important aspect of the intrinsic mechanisms of regulation. Intrinsic mechanisms are usually induced by specific antigen but affect the immune responses either specifically or non-specifically. In general, the intrinsic mechanisms have evolved to control the magnitude and class of immune responses to ensure an optimal immune response to foreign antigens by avoiding the collateral damage due to excessive reactions. However, the intrinsic mechanisms, by dampening all immune responses, may also play a vital role in non-specific amelioration of pathogenic auto-immunity (27, 59).

Superimposed on the intrinsic mechanisms of homeostatic regulation are the extrinsic regulatory mechanisms mediated by distinct T subsets of regulatory NKT, CD4+ and CD8+ T cells, which may dominantly suppress the outgrowth of potentially pathogenic self-reactive T cells in the periphery either by controlling the magnitude and class of immune responses or by discriminating self from non-self (27, 59). Both self/non-self discrimination and the control of magnitude and class of immune response must function in concert to ensure the optimal function of the immune system.

A central issue is how the peripheral immune responses are regulated at a biological system level, which enables the immune system to discriminate self from non-self in order to maintain self-tolerance without damaging its capacity to react to the invasion of foreign pathogens. In this regard, there is currently no unified conceptual framework to characterize the precise relationship between thymic negative selection and peripheral immune regulation which is the basis for understanding self/non-self discrimination. The absence of a unified conceptual framework has led to confusion, at both theoretical and experimental levels, in the field of immune regulation. For example, the prevailing theory, which currently dominates the field of immune-regulation and profoundly influences the general thinking in this field, is the role of specialized Tregs. Specialized Tregs have been characterized by the expression of, initially, the CD25 molecule (60-62) and recently, the transcription factor Foxp3 (63-65), known to regulate T cell activation and expression of certain cytokines (66, 67). The Tregs were postulated to be a naturally occurring, lineage specific T cell subset with a rather diverse TCR repertoire similar to conventional CD4+ T cells (68,69). Selection of these cells by certain self-antigens expressed on stromal cells in the thymus has been proposed as the mechanism for the development of the Tregs (68-71). The precise nature of the self-peptides involved has not been elucidated.

The specialized Tregs have been considered to be the key mechanism mediating self-tolerance by suppression (69, 72-74). However, although the specialized Tregs can be activated and induced by both self and foreign antigens, the specificity of the suppression is unclear and the target cells, as well as the molecular interactions between target cells and the Tregs, are unknown (26, 27). In fact, the in vitro assay that has been universally employed to monitor the effector phase of suppression mediated by the specialized Tregs does not seem to involve T cell receptor nor to be MHC restricted (75, 76), although it has been shown that the in vivo suppression could be antigen specific (65, 71, 77).

At the effector phase, the suppression is, at least in part, cell-contact dependent, but the surface molecules involved in the cell contact are unidentified (76). In addition, IL-10 and TGF-β, which participate in the intrinsic mechanisms of suppression, have also been implicated in suppression by the specialized Tregs. Importantly, at a biological system level, while suppressing the auto-immunity, these cells are also found to suppress the immune responses to foreign antigens, including anti-bacteria, anti-virus, anti-fungi and anti-parasite responses in infectious disease (69, 78, 79), as well as anti-allo response in organ transplantation (69, 80-82). Thus, the suppression appears to be global, covering the entire spectrum of immune responses to both self and foreign antigens.

These observations strongly suggest that the specialized Tregs are unlikely to control auto-immunity by means of self non-self discrimination. Instead, the evidence suggests that the specialized Tregs may ameliorate pathogenic auto-immunity by controlling the magnitude and class of immune responses, much like the regulation mediated by conventional Th1 versus Th2 or Tr1 and Tr3 cells (26, 27). Currently, it is unclear whether these cells do commit to a stable lineage or whether the regulatory phenotype is a more plastic reversible state (68, 83), although recent studies showed that naïve CD4+ T cells can covert into antigen-specific Tregs triggered by foreign antigens under certain conditions (40). The conceptual dilemma is if the specialized Tregs are indeed a lineage-specific subset of T cells, what defines it? Can Foxp3 function as a lineage-specific marker to define the specialized Tregs when itself is an inducible gene which is dynamically regulated during effector T cell differentiation 66, 67, 84, 85 and is only linked to the functional stage of certain T cells (63-65). If the specialized Tregs are not a lineage-specific subset of T cells, what is the difference between the specialized Tregs and the conventional T cells, which exert the regulatory function (including Th1 versus Th2 or Tr1 and Tr3 cells) Taken together, the conceptual framework to uniformly explain the biological functions of specialized Tregs in vivo remains a work in progress (62, 86-88).

To classify the existing peripheral regulatory mechanisms, in the context of either self/non-self discrimination or control of magnitude and class of immune response, is not only conceptually important but also directly related to the development of precise and safe therapeutic approaches to solve clinical problems caused by different immune mechanisms.

An "Avidity Model" of Peripheral T Cell Regulation

During the past few years, an "Avidity Model" of Peripheral T Cell Regulation has been proposed and tested, which may provide a unifying conceptual framework to understand how peripheral immune responses, to both self and foreign antigens, are regulated (42,43). The concept of the Avidity Model first emerged from the observations that CD8+ T cells were involved in amelioration of Experimental Allergic Encephalomyelitis (EAE) by selectively down-regulating certain but not all self-peptide 1-9Nac MBP (myelin basic protein) reactive T cells enriched with encephalitogenic clones with higher growth potential to MBP (40, 89). This set of regulatory CD8+ T cells were initially discovered to be involved in the resistance to EAE that is induced during the first episode of the disease (89, 90). It was later shown that the interaction between the CD8+ T cells and the target T cells is restricted by the MHC class Ib molecule, Qa-1 (66-68). More severe symptoms of EAE, in a much less controllable fashion, develop in molecularly engineered CD8 or Qa-1 deficient mice exposed to myelin-associated peptides (90, 94). The experiments that directly led to the formulation of the Avidity Model were the further observations that the Qa-1 dependent CD8+ T cells were found to inhibit the immune response to a conventional antigen Hen Egg Lysozyme (HEL) when it functions as a self-antigen in HEL transgenic (TG) mice, but enhance the immune response to the same antigen when it functions as a foreign antigen in wild type (WT) mice (18). Thus, the Qa-1 dependent CD8+ T cells are involved in both the maintenance of peripheral tolerance to self-antigen and the optimization of T cell responses to foreign antigens.

Using a panel of HEL-specific CD4+ T cell clones with different avidity it was shown that the susceptibility of the target T cells to the down-regulation by the CD8+ T cells is determined by the avidity of the interactions which activates the T cell clones. In a wide range of the antigen doses used to activate the T cell clones, Qa-1 dependent CD8+ T cells selectively down-regulate the HEL-specific clones of intermediate but not high or low avidity, regardless whether these clones are derived from WT or from HEL TG mice (43). It was concluded from these studies that the strategy used by the Qa-1 dependent CD8+ T cells to accomplish their tasks in vivo is to selectively down-regulate activated T cells of intermediate avidity specific to both self and foreign antigens. Thus, the susceptibility of activated T cells to down-regulation by the Qa-1 dependent CD8+ T cells is determined by the avidity of the interactions during the initial T cell activation (43). This regulatory pathway is envisioned to be composed of a series of sequential cellular events as illustrated in FIG. 1.

However, although the recognition of T cell targets is blocked by mAbs to Qa-1, CD8 and TCR (43, 91-93), the actual target structure that is recognized by the TCR of CD8+ T cells is not known.

The identification of a universal target structure revealed herein, and the novel methods also disclosed herein, permit control and/or amelioration of autoimmune diseases that can be achieved independently of the knowledge of the particular self-antigens involved in the given autoimmune disease.

SUMMARY OF THE INVENTION

Identification herein of target structure on antigen-activated Qa-1+/HLA-E+ T cells that is recognized by the TCR of CD8+ T cells permits access to the only universal mechanism involved in autoimmunity only.

Thus, the novel methods disclosed herein permit control and/or amelioration of autoimmune diseases that can be achieved independent of the knowledge of the particular self-antigens involved in the given autoimmune disease.

A method is provided for enhancing down-regulation of an antigen-activated HLA-E+ T cell by an HLA-E-restricted or HLA-E-dependent CD8+ T cell comprising contacting the HLA-E+ T cell and CD8+ T cell with an agent which enhances binding between (i) T cell receptor (TCR) on the surface of the CD8+ T cell and (ii) a type B self peptide presented by HLA-E on the surface of the HLA-E+ T cell, thereby enhancing down-regulation of the antigen-activated HLA-E+ T cell.

A method is provided for enhancing down-regulation of an antigen-activated Qa-1+ T cell by a Qa-1-dependent CD8+ T cell comprising contacting the Qa-1+ T cell and CD8+ T cell with an agent which enhances binding between (i) T cell receptor (TCR) on the surface of the CD8+ T cell and (ii) a type B self peptide presented by Qa-1 on the surface of the Qa-1+ T cell, thereby enhancing down-regulation of the antigen-activated Qa-1+ T cell.

A method is provided for treating a human subject afflicted with a disorder selected from the group consisting of an autoimmune disease, graft transplant rejection and bacterial infection comprising administering to the subject a therapeutically effective amount of an agent which enhances binding between (i) a T cell receptor (TCR) on the surface of an HLA-E-restricted or HLA-E-dependent CD8+ T cell and (ii) a type B self peptide presented by HLA-E on the surface of an HLA-E+ T cell, thereby treating the subject.

A method is provided for inhibiting in a human subject the onset of a disorder selected from the group consisting of an autoimmune disease, graft transplant rejection and bacterial infection comprising administering to the subject a prophylactically effective amount of an agent which enhances binding between (i) a T cell receptor (TCR) on the surface of an HLA-E-restricted or HLA-E-dependent CD8+ T cell and (ii) a type-B self peptide presented by HLA-E on the surface of an HLA-E+ T cell, thereby treating the subject.

A dendritic cell-derived, Qa-1-bearing exosome loaded with self peptide is provided. A dendritic cell-derived, HLA-E-bearing exosome loaded with self peptide is provided. A membrane-bounded composition bearing Qa-1 and comprising type B self peptide is provided. A membrane-bounded composition bearing HLA-E and comprising type B self peptide is provided.

Membrane-bounded compositions may be derived from plasma membranes, or can be synthesized, for example liposomes.

A method is provided for inhibiting down-regulation of an antigen-activated HLA-E+ T cell by an HLA-E-restricted or HLA-E-dependent CD8+ T cell comprising contacting the HLA-E+ T cell and CD8+ T cell with an agent which inhibits binding between (i) T cell receptor (TCR) on the surface of the CD8+ T cell and (ii) a type B self peptide presented by HLA-E on the surface of the HLA-E+ T cell, thereby inhibiting down-regulation of the antigen-activated HLA-E+ T cell.

A method is provided for inhibiting down-regulation of an antigen-activated Qa-1+ T cell by a Qa-1-dependent CD8+ T cell comprising contacting the Qa-1+ T cell and CD8+ T cell with an agent which inhibits binding between (i) T cell receptor (TCR) on the surface of the CD8+ T cell and (ii) a type B self peptide presented by Qa-1 on the surface of the Qa-1+ T cell, thereby inhibiting down-regulation of the antigen-activated Qa-1+ T cell.

A method is provided for treating a human subject afflicted with a disorder characterized by excessive CD8+ T cell-mediated immunosuppression comprising administering to the subject a therapeutically effective amount of an agent which inhibits binding between (i) a T cell receptor (TCR) on the surface of an HLA-E-restricted or HLA-E-dependent CD8+ T cell and (ii) a type B self peptide presented by HLA-E on the surface of an HLA-E+ T cell, thereby treating the subject.

An isolated antibody is provided which specifically binds to a complex comprising a type B self peptide and Qa-1. An isolated antibody is provided which specifically binds to a complex comprising a type B self peptide and HLA-E.

A method is provided for isolating HLA-E-restricted or HLA-E-dependent CD8+ T cells present in a T cell-containing sample comprising:
(a) contacting the sample with immobilized HLA-E-presented type B self peptide under conditions permitting binding of the type B self peptide with HLA-E-restricted or HLA-E-dependent CD8+ T cells in the sample;
(b) removing unbound T cells; and (c) dissociating from the immobilized type B self peptide any bound HLA-E-restricted or HLA-E-dependent CD8+ T cells, thereby isolating HLA-E-restricted or HLA-E-dependent CD8+ T cells from the sample.

A method is provided of identifying an agent as an enhancer of down-regulation of antigen-activated intermediate avidity Qa-1+ T cells by Qa-1-dependent CD8+ T cells comprising:
 a) providing an antigen-activated Qa-1+ T cell and a Qa-1-dependent CD8+ T cell;
 b) contacting the antigen-activated Qa-1+ T cell with the Qa-1-dependent CD8+ T cell;
 c) quantitating down-regulation of the antigen-activated Qa-1+ T cell;
 d) repeating steps b) and c) in the presence of the agent; and
 e) comparing the down-regulation quantitated in step d) with the down-regulation quantitated in step c), wherein down-regulation quantitated in step d) greater than that quantitated in step c) indicates that the agent is an enhancer of down-regulation of antigen-activated intermediate avidity Qa-1+ T cells by Qa-1-dependent CD8+ T cells.

A method is provided of identifying an agent as an inhibitor of down-regulation of intermediate avidity antigen-activated Qa-1+ T cells by Qa-1-dependent CD8+ T cells comprising:
 a) providing an activated Qa-1+ T cell and a Qa-1-dependent CD8+ T cell;
 b) contacting the activated Qa-1+ T cell with the Qa-1-dependent CD8+ T cell;
 c) quantitating down-regulation of the activated Qa-1+ T cell;
 d) repeating steps b) and c) in the presence of the agent; and
 e) comparing the down-regulation quantitated in step d) with the down-regulation quantitated in step c), wherein down-regulation quantitated in step d) less than that quantitated in step c) indicates that the agent is an inhibitor of down-regulation of intermediate avidity antigen-activated Qa-1+ T cells by Qa-1-dependent CD8+ T cells.

A method is provided of inhibiting down-regulation of an antigen-activated HLA-E+ T cell by an HLA-E-restricted or HLA-E-dependent CD8+ T cell comprising introducing a nucleic acid into the HLA-E+ T cell or CD8+ T cell so as to inhibit binding between (i) T cell receptor (TCR) on the surface of the CD8+ T cell and (ii) a type B self peptide presented by HLA-E on the surface of the HLA-E+ T cell, thereby inhibiting down-regulation of the antigen-activated HLA-E+ T cell.

A method is provided of inhibiting an antigen-activated HLA-E+ T cell comprising contacting an HLA-E-restricted CD8+ T cell with an agent which activates the HLA-E-restricted CD8+ T cell to inhibit the HLA-E+ T cell.

A process is provided of manufacturing a pharmaceutical for treating an autoimmune disease comprising:
 a) identifying an agent that enhances binding between an HLA-E-restricted CD8+ T cell and an antigen-activated HLA-E+ T cell; and
 b) admixing the agent identified in step a) with a pharmaceutically acceptable carrier so as to thereby manufacture the pharmaceutical.

An isolated peptide having the sequence set forth in SEQ ID NO:2.

A vaccine composition is provided comprising an HLA-E/type B self peptide tetramer.

▲ ● ◆ :
Represent H/M/Qa-1 Protein Indexes of T cell clones from three separate experiments;

△ ▲ ▲ :
Represent H/M/Qa-1 Protein Indexes of T cell clones stimulated with different doses (1 μM, 10 μM and 50 μM) of HEL in each experiment.

Figure 6:
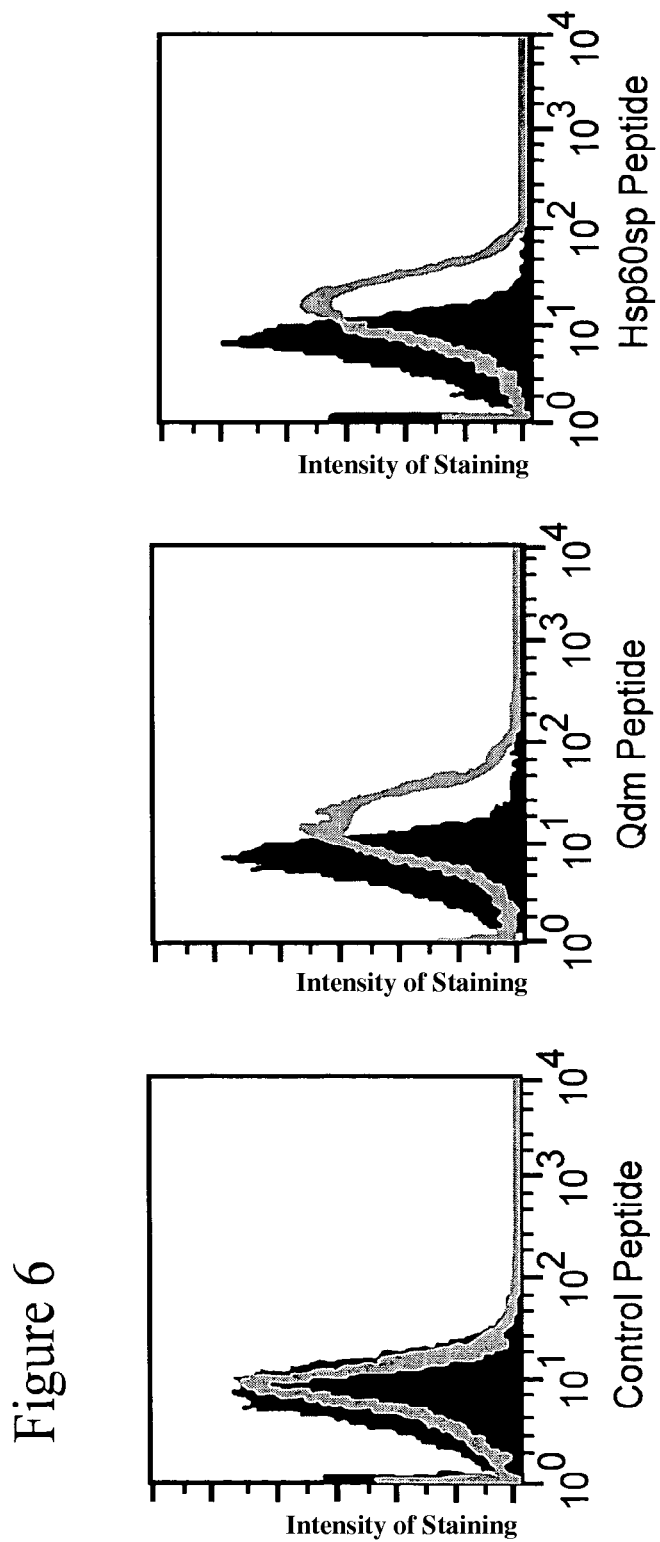

FIG. 6: Hsp60sp peptide is a specific target for Qa-1 dependent CD8+ T cells. Hsp60sp peptide is capable of binding to Qa-1. 3F4 cells were incubated with Hsp60sp, Qdm and control peptides at 26° C. and 37° C. for 18 hrs, and stained with anti Qa-1a serum revealed by Goat anti-Mouse-PE, analyzed by FACS as described in the Method. Shaded curves represent the Qa-1 staining of samples loaded with peptide at 37° C. and light curves represent the Qa-1 staining of samples loaded with peptide at 26° C.

Figure 7:
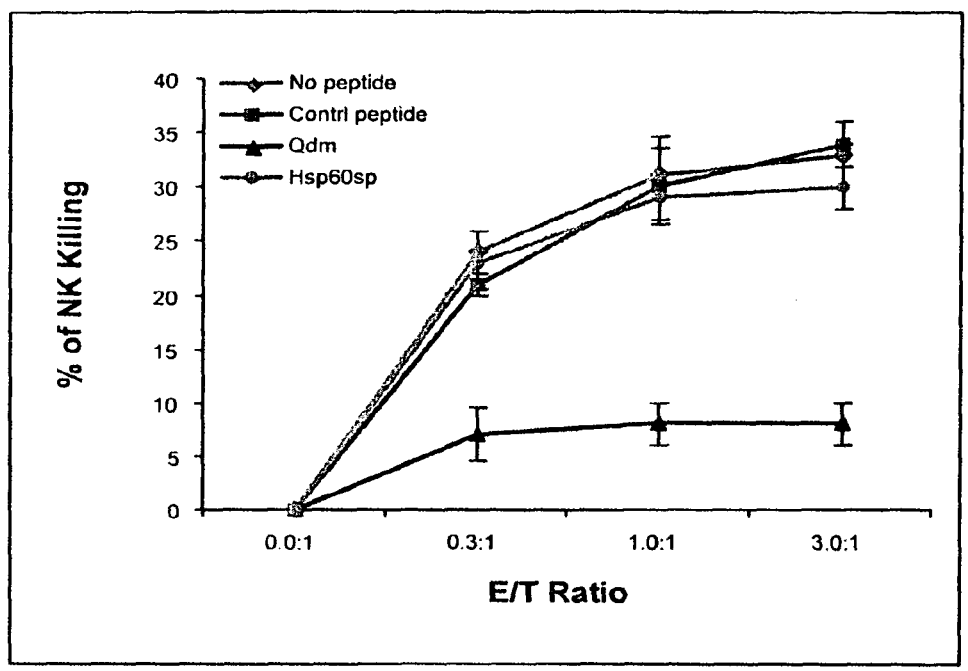

FIG. 7: Hsp60sp peptide does not inhibit NK killing when coupled with Qa-1, indicating that Qa-1/Hsp60sp does not interact with CD94/NKG2A receptor on the NK cells. 3F4 cells loaded with Hsp60sp, Qdm and control peptides were used as peptide-presenting cells in a standard NK assay as described in the Methods. The figure is representative of four separate experiments.

Figure 8:
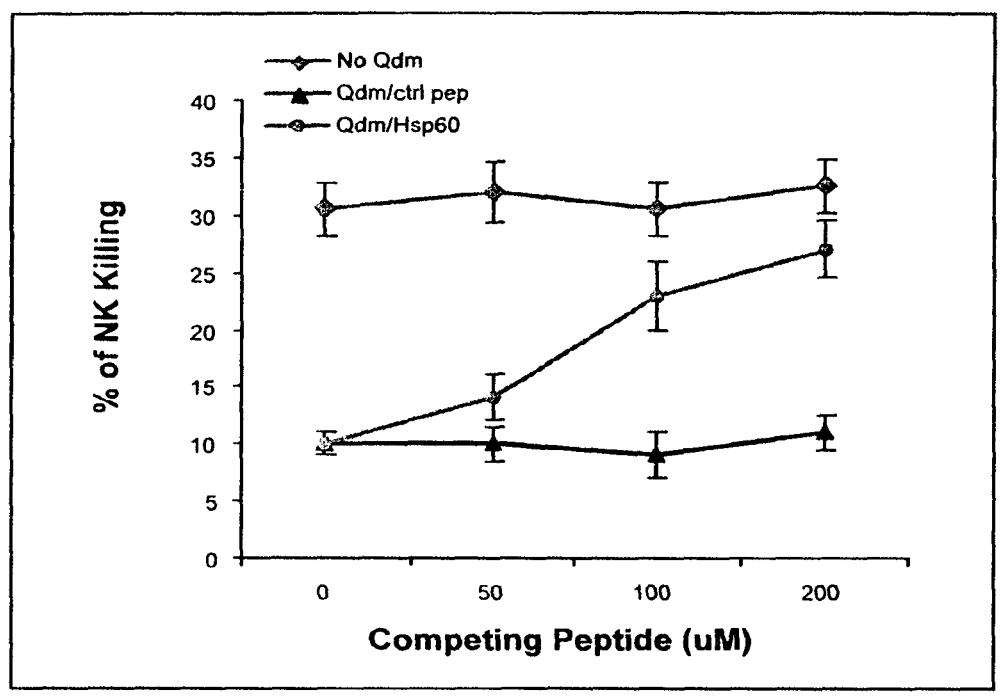

FIG. 8: Hsp60sp peptide is capable of competing with Qdm for binding to Qa-1. Hsp60 and control peptide were loaded, together with Qdm (20 μM), to the 3F4 for 18 hrs at 26° C. and tested in a standard NK assay (E/T ratio 2:1) as described in the methods. Hsp60sp peptide but not control peptide abrogated the inhibition of killing of 3F4 by Qdm, in a dose dependent manner, indicating that Hsp60sp is capable of competing with Qdm for binding to Qa-1. The figure is representative of four separate experiments.

Figure 9:
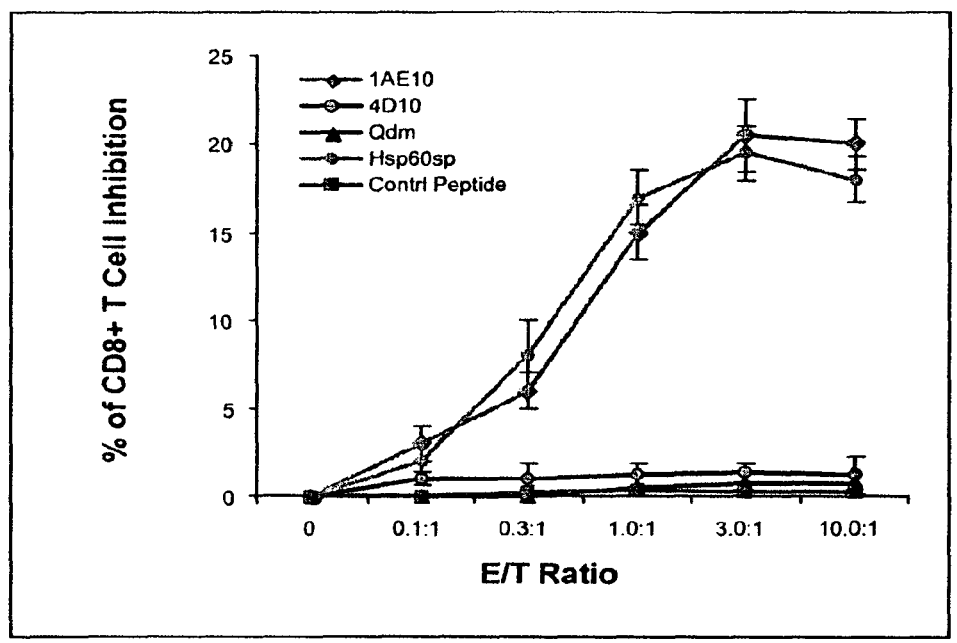

FIG. 9: Hsp60sp peptide renders Qa-1 expressing cells susceptible to the down-regulation by the Qa-1 dependent CD8+ T cells. 3F4 cells loaded with Hsp60sp, Qdm and control peptides were used as peptide-presenting cells in a standard CD8+ T cell inhibition assay as described in the Methods. Intermediate avidity 1-9NacMBP specific encephalitogenic clone 1AE10 and low avidity 1-9NacMBP specific non-encephalitogenic clone 4D10 was used as controls. CD8+ T cells were isolated from the EAE protected B10PL mice and CD8+ T cells from naïve mice used as controls as described (1). It has been established by our previous and current studies that CD8+ T cells isolated from naïve mice has no effect on clone 1AE10 and 3F4 cells loaded with Hsp60sp peptide. The figure is representative of four separate experiments.

Figure 10:
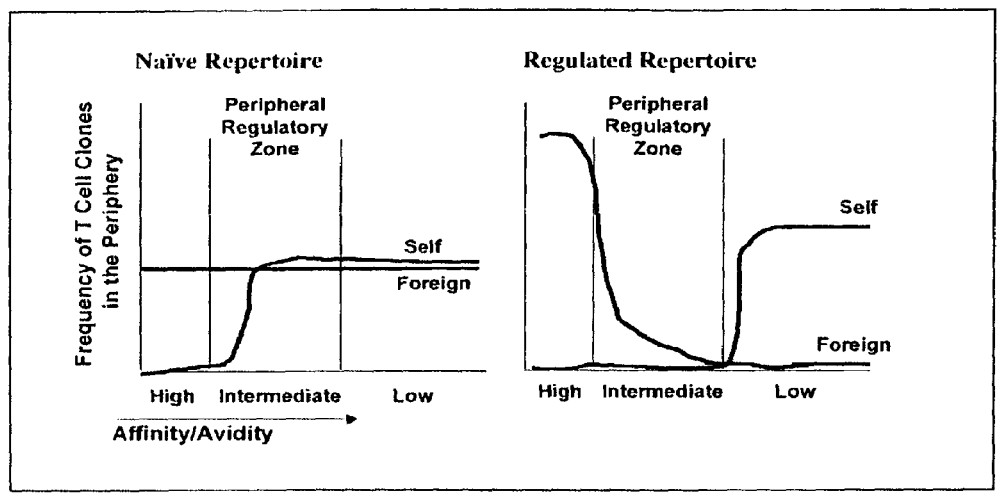

FIG. 10: The selective down-regulation of intermediate avidity T cells by the CD8+ T cells shapes the peripheral T cell repertoire to both self and foreign antigens during the evolution of immune responses. Because the compositions of the naïve peripheral TCR repertoires to self and foreign antigens are different due to thymic negative selection, the biological consequences of selective down-regulation of the intermediate avidity T cells to self and foreign antigens are also different. Intrathymic deletion of high avidity self-reactive T cell clones generates a truncated peripheral self-reactive repertoire only composed of intermediate and low but devoid of high avidity clones compared with the foreign-reactive repertoire. Thus, selective down-regulation of the intermediate avidity T cell populations containing potentially pathogenic self-reactive T cells provides a mechanism to specifically control autoimmune diseases without damaging the effective anti-infection immunity, which is, largely, mediated by high avidity T cells specific to the infectious pathogens.

Figure 11:
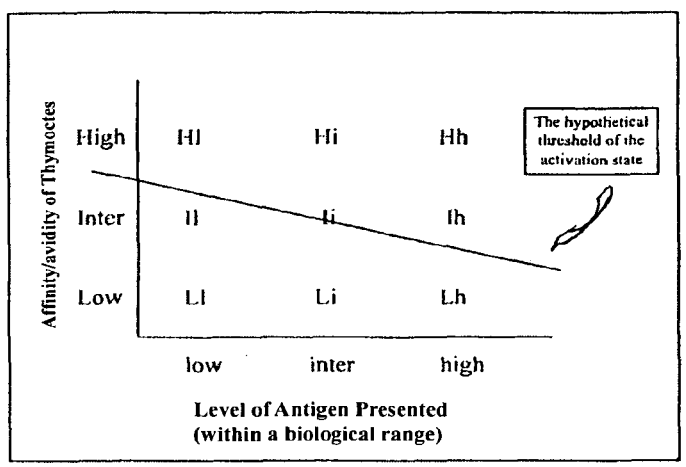

FIG. 11: A hypothetical threshold of activation state of thymocytes to undergo apoptosis during thymic negative selection. The Y-axis represents TCR avidity, which is determined by the affinity dictated by the structures of the TCRs and the density of TCRs expressed on each thymocyte. The X-axis represents the level of self-antigens presented in the thymus, which is determined by the number and the affinity of the MHC/self-peptide complex expressed on the surface of APCs, as well as the presentation capacity of the APCs. Thymocytes of activation state beyond the threshold undergo apoptosis and thymocytes of activation state below the threshold are spared from apoptosis and released into the periphery FIG. 12: The functional window of the peripheral T cell regulation by the Qa-1 dependent CD8+ T cells. It covers the intermediate avidity T cells activated by a wide spectrum of the levels that the antigen is presented, especially when the level of antigen presented moves from low to intermediate or from intermediate to middle high. The small tail area that is pushed outside the regulatory window represents certain rare extreme cases which are likely occur due to potent co-stimulation during T cell activation by clinical therapies.

Figure 13:
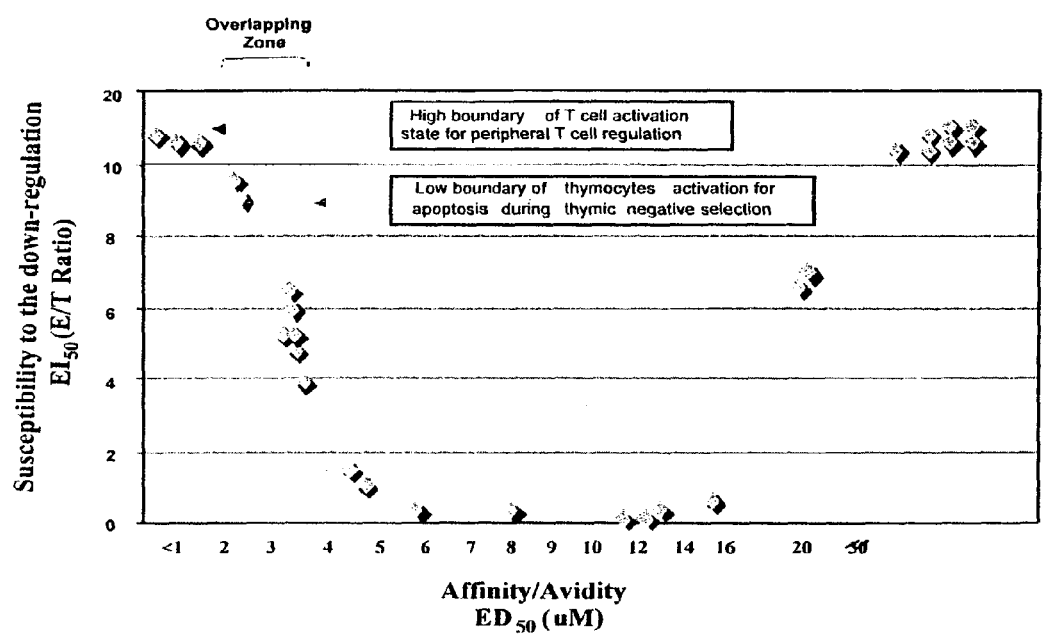

FIG. 13: An overlapping zone of avidity in the periphery between the low boundary of the activation state of thymocytes for apoptosis in thymus and the high boundary of the T cell activation state for peripheral down-regulation exist in the periphery. The low boundary for thymocytes to undergo apoptosis during thymic negative selection is much lower than the high boundary of T cell activation state for peripheral T cell regulation. This creates an overlapping zone in the periphery between the low boundary of the activation state of thymocytes for apoptosis in thymus, which allows intermediate avidity T ells to escape into the periphery, and the high boundary of the T cell activation state for down-regulation. The overlapping zone provides a safe guard for maintaining the peripheral self-tolerance. Each dot represents one actual HEL clone with its susceptibility to the down-regulation by the Qa-1 dependent CD8+ T cells.

Figure 14:
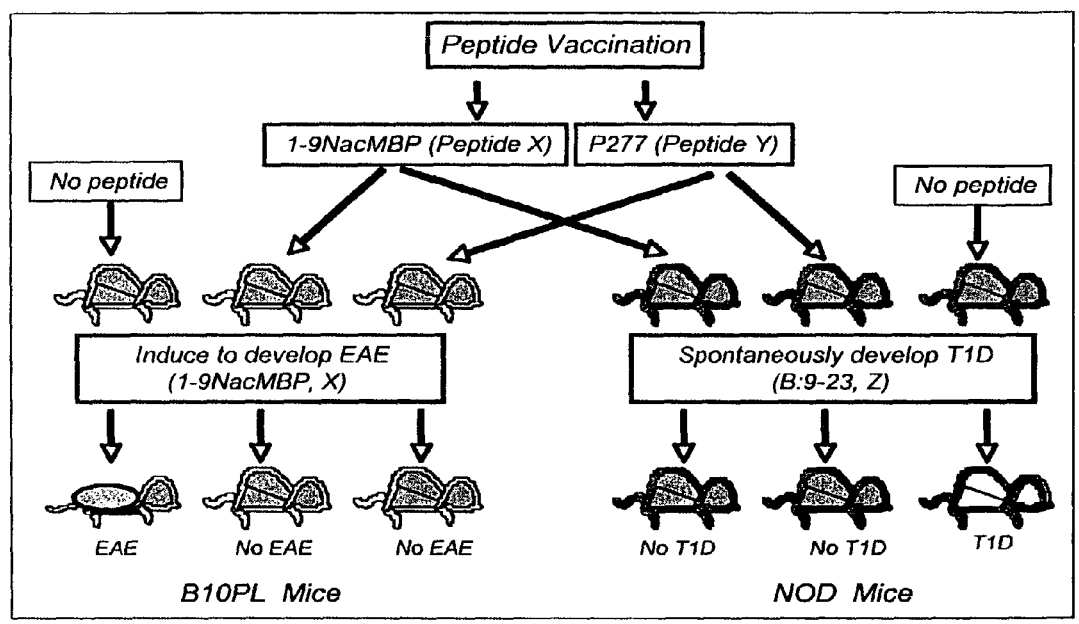

FIG. 14: "Cross-protection" phenomenon in both EAE and T1D autoimmune disease models. Animals are protected by vaccination with different antigen peptides.

FIG. 15A-15D: Vaccination with self-peptide 1-9NacMBP or P277 "cross-protected" B10PL mice from EAE and NOD mice from T1D and the protection is CD8+ T cell dependent.

15A. Vaccination of B10PL mice with 1-9Nac MBP or P277 peptide equally protected B10PL mice from the subsequent induction of EAE. The figure is representative of four separate experiments with 4-5 mice/group.

15B. Vaccination of NOD mice with 1-9Nac MBP or P277 peptide equally protected NOD mice from the spontaneously developed T1D. The figure is representative of four separate experiments with 4-5 mice/group.

15C. CD8+T cells isolated from either 1-9NacMBP or P277 peptide vaccination protected EAE mice further protected naïve B10PL mice from the subsequently induced EAE when adoptively transferred. Control: Mice induced to develop EAE without CD8+ T cell transfer. CD8T/Naïve: Mice induced to develop EAE after adoptively transferred with CD8+ T cells from naïve mice. CD8T/MBP: Mice induced to develop EAE but protected when adoptively transferred with CD8+ T cells from 1-9MacMBP vaccination protected EAE mice. CD8T/p277: Mice induced to develop EAE but protected when adoptively transferred with CD8+ T cells from p277 vaccination protected EAE mice. The figure is representative of four separate experiments with 4-5 mice/group.

15D. CD8+T cells isolated from either 1-9NacMBP or P277 peptide vaccination protected T1D mice further protected naïve NOD mice from the spontaneously developed T1D when adoptively transferred. Control: Mice spontaneously developed T1D without CD8+ T cell transfer. CD8T/Naïve: Mice spontaneously developed T1D after adoptively transferred with CD8+ T cells from naïve mice. CD8T/MBP: Mice were protected from T1D when adoptively transferred with CD8+ T cells from 1-9MacMBP vaccination protected T1D mice. CD8T/p277: Mice were protected from T1D when adoptively transferred with CD8+ T cells from p277 vaccination protected T1D mice. The figure is representative of four separate experiments with 4-5 mice/group.

Figure 16:
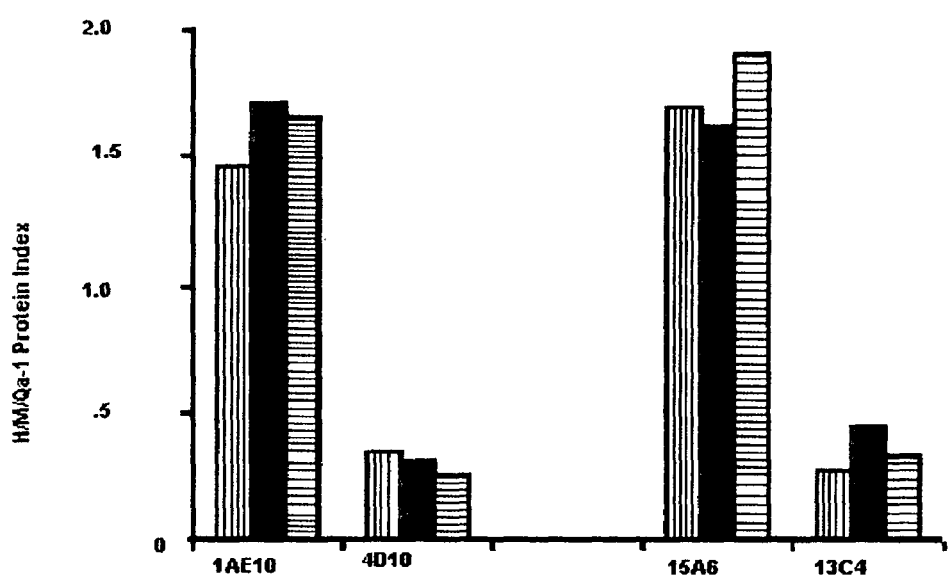

FIG. 16: The H/M/Qa-1 Protein Index of 1-9Nac MBP specific intermediate avidity clone 1AE10 and low avidity clone 4D10 as well as p277 specific intermediate avidity clone 15A6 and low avidity clone 13C4. The figure summarizes three separate experiments. H/M/Qa-1 protein Index is calculated as H/M Protein Expression Ratio times Protein Expression Index of Qa-1, which represents the ratio of Hsp60 versus MHC Class Ia, normalized to Qa-1 at protein expression level; Protein Expression Index is the ratio of protein expression between a given protein and β-actin in the same cells, and H/M protein Expression ratio is the ratio of protein Expression Index between Hsp60 and MHC Class Ia.

FIG. 17A-17B: 17A. CD8+ T cells isolated from either 1-9NacMBP or p277 peptide vaccination protected EAE mice selectively inhibit an encephalitogenic intermediate avidity 1-9NacMBP specific T cell clone 1AE10 or transfectant 3F4 loaded with Hsp60sp but not control low avidity clone 4D10 or transfectant 3F4 loaded with Qdm and control peptide. Xxx/m represent experiments assayed for CD8+ T cells isolated from MBP peptide vaccination protected mice and xxx/p represent experiments assayed for CD8+ T cells isolated from p277 peptide vaccination protected mice. The figure is representative of four separate experiments performed in B10PL mice.

17B. CD8+ T cells isolated from either 1-9NacMBP or p277 peptide vaccination protected T1D mice selectively inhibit a intermediate avidity p277 specific T cell clone 15A6 or transfectant 3F4 loaded with Hsp60sp but not control low avidity clone 13C4 or transfectant 3F4 loaded with Qdm and control peptide. Xxx/m represent experiments assayed for CD8+ T cells isolated from MBP peptide vaccination protected mice and xxx/p represent experiments assayed for CD8+ T cells isolated from p277 peptide vaccination protected mice. The figure is representative of four separate experiments performed in NOD mice.

FIG. 18A-18B: 18A. CD8+ T cells isolated from either 1-9NacMBP or p277 vaccination protected B10PL mice inhibited the overall immune response to the pathogenic self-antigen 1-9NacMBP but not to the conventional foreign antigen HEL, in an ex-vivo primary response in the recipient mice, when adoptively transferred. The ex-vivo primary responses of T cells from the draining lymph nodes were tested in a standard T cell proliferation assay one week after in vivo antigen challenge. CD8T/Naïve/HEL: Mice receive the CD8+ T cells from naïve B10PL mice before immunization with HEL and tested for HEL response. CD8T/MBP/HEL: Mice receive the CD8+ T cells from 1-9NacMBP vaccinated B10PL mice before immunization with HEL and tested for HEL. CD8T/p277/HEL: Mice receive the CD8+ T cells from p277 vaccinated B10PL mice before immunization with HEL and tested for HEL. CD8T/Naïve/MBP: Mice receive the CD8+ T cells from naive B10PL mice before immunization with MBP and tested for MBP response. CD8T/MBP/MBP: Mice receive the CD8+ T cells from 1-9NacMBP vaccinated B10PL mice before immunization with MBP and tested for MBP response. CD8T/p277/MBP: Mice receive the CD8+ T cells from p277 vaccinated B10PL mice before immunization with MBP and tested for MBP response. The figure is representative of four separate experiments.

18B. CD8+ T cells isolated from either 1-9NacMBP or p277 vaccination protected NOD mice inhibited the overall immune response to the pathogenic self-antigen B: 9-23 but not to the conventional foreign antigen HEL, in an ex-vivo primary response in the recipient mice, when adoptively transferred. The ex-vivo primary responses of T cells from the draining lymph nodes were tested in a standard T cell proliferation assay one week after in vivo antigen challenge. CD8T/Naïve/HEL: Mice receive the CD8+ T cells from naïve NOD mice before immunization with HEL and tested for HEL response. CD8T/MBP/HEL: Mice receive the CD8+ T cells from 1-9NacMBP vaccinated NOD mice before immunization with HEL and tested for HEL. CD8T/p277/HEL: Mice receive the CD8+ T cells from p277 vaccinated NOD mice before immunization with HEL and tested for HEL. CD8T/Naïve/B: 9: Mice receive the CD8+ T cells from naive NOD mice before immunization with B: 9-23 and tested for B: 9-23 response. CD8T/MBP/B: 9: Mice receive the CD8+ T cells from 1-9NacMBP vaccinated NOD mice before immunization with B: 9-23 and tested for B: 9-23 response. CD8T/p277/B: 9: Mice receive the CD8+ T cells from p277 vaccinated NOD mice before immunization with B: 9-23 and tested for B: 9-23 response. The figure is representative of four separate experiments.

Figure 19:
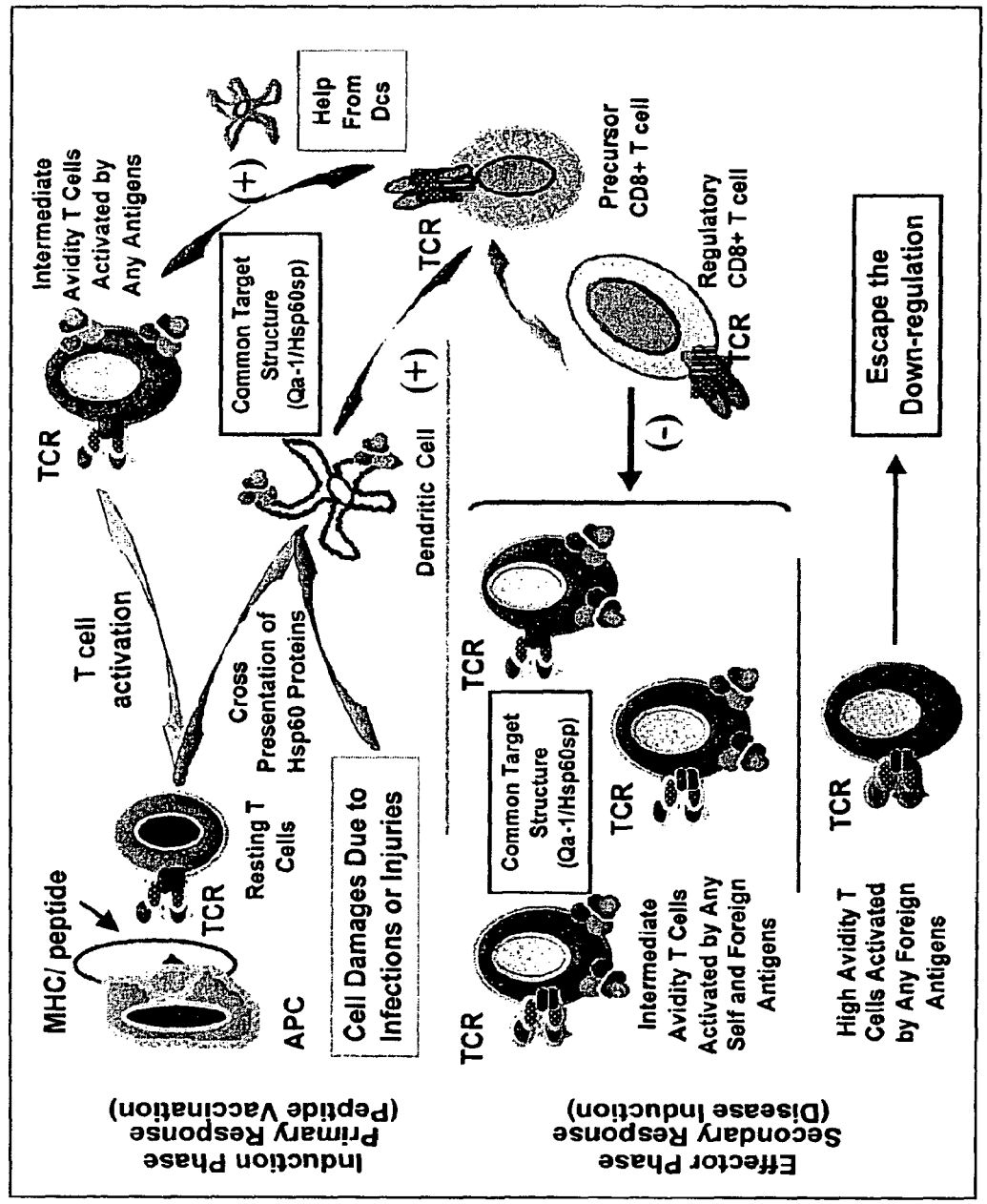

FIG. 19: The cellular events of the cross-protection mediated by Qa-1 restricted CD8+ T cells. The link between the induction and effector phases of the Qa-1 restricted CD8+ T cell mediated pathway is the common surrogate target structure, such as Qa-1/Hsp60sp, predominantly expressed on both inducing and target T cells that are of intermediate avidity, regardless of which antigens these T cells are triggered by.

FIGS. 20A-20E: CD8+ T Cells in the freshly isolated PBMC from a T1D patient lost the capacity to discriminate self from nonself (20A-D) and lost the capacity to specifically recognize HLA-E/HSP60SP target structure (20E), compared with normal individual.

FIGS. 21A-21E: 21A-E—CD8+ T cells restored the capacity to discriminate self from nonself after in vitro boosted with autologous DCs loaded with hsp60sp peptide, compared with normal individual. 21E-F. CD8+ T cells restored the capacity to specifically recognize the target structure HLA-E/Hsp60sp, after in vitro boosted with autologous DCs loaded with Hsp60sp Peptide, compared with normal individual.

DETAILED DESCRIPTION OF THE INVENTION

As used herein, a "prophylactically effective" amount is an amount of a substance effective to prevent or to delay the onset of a given pathological condition in a subject to which the substance is to be administered.

As used herein, a "therapeutically effective" amount is an amount of a substance effective to treat, ameliorate or lessen a symptom or cause of a given pathological condition in a subject suffering therefrom to which the substance is to be administered.

In one embodiment, the therapeutically or prophylactically effective amount is from about 1 mg of agent/subject to about 1 g of agent/subject per dosing. In another embodiment, the therapeutically or prophylactically effective amount is from about 10 mg of agent/subject to 500 mg of agent/subject. In a further embodiment, the therapeutically or prophylactically effective amount is from about 50 mg of agent/subject to 200 mg of agent/subject. In a further embodiment, the therapeutically or prophylactically effective amount is about 100 mg of agent/subject. In still a further embodiment, the therapeutically or prophylactically effective amount is selected from 50 mg of agent/subject, 100 mg of agent/subject, 150 mg of agent/subject, 200 mg of agent/subject, 250 mg of agent/subject, 300 mg of agent/subject, 400 mg of agent/subject and 500 mg of agent/subject.

As used herein a "type-B peptide" or "type-B self peptide" is a Qa-1-binding or HLA-E-binding peptide, as appropriate, that (i) does not inhibit NK cells by binding to CD94/NKG2A when bound to Qa-1 or HLA-E, respectively (ii) is recognized by regulatory CD8+ T cells when bound to Qa-1 or HLA-E, respectively, and (iii) can compete with type-A QA-1/HLA-E binding peptides, such as Qdm or B7sp, for binding to Qa-1 or HLA-E, respectively. Preferably, the type-B peptide is a nonomer.

As used herein "HLA-E" has the common meaning as used in the art, i.e. human leukocyte antigen system E.

As used herein a "Qa-1 or HLA-E restricted CD8+ T cell" is a regulatory CD8+ T cell that recognizes the peptides presented by the Qa-1 or HLA-E molecule, respectively, on the immune system antigen presenting cells (APC). The APC for the Qa-1/HLA-E restricted CD8+ T cells as encompassed herein are intermediate avidity T cells, which are also specific targets for these CD8+ T cells.

"Administering" an agent can be effected or performed using any of the various methods and delivery systems known to those skilled in the art. The administering can be performed, for example, intravenously, orally, nasally, via the cerebrospinal fluid, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, a "pharmaceutically acceptable carrier" is a pharmaceutically acceptable solvent, suspending agent or vehicle, for delivering the instant compounds to the animal or human. The carrier may be liquid, aerosol, gel or solid and is selected with the planned manner of administration in mind.

"Agent" shall mean any chemical entity, including, without limitation, a glycomer, a protein, an antibody, a lectin, a nucleic acid, a small molecule, and any combination thereof, as well as biological entities such as exosomes or liposomes. Examples of possible agents include, but are not limited to, monoclonal antibody, a ribozyme, a DNAzyme and an siRNA molecule.

"siRNA" shall mean small interfering ribonucleic acid. Methods of designing and producing siRNA to decrease the expression of a target protein are well known in the art.

"Structurally related peptide" with regard to Hsp60sp means a peptide having from 70% to 99% sequence similarity with the sequence set forth in SEQ ID NO:2.

"Tumor" includes cancerous and non-cancerous tumors. Cancerous tumors include, without limitation, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor.

As used herein "antigen-activated HLA-E$^+$ T cell" encompasses, as appropriate, autoreactive T cells, i.e. where the "antigen" is self. Accordingly, in an embodiment of each of the methods described herein reciting antigen-activated HLA-E$^+$ T cell, the cell is a self-antigen activated HLA-E$^+$ T cell.

A method is provided for enhancing or activating down-regulation of an antigen-activated HLA-E$^+$ T cell by an HLA-E-dependent or HLA-E-restricted CD8$^+$ T cell comprising contacting the HLA-E$^+$ T cell and CD8$^+$ T cell with an agent which enhances or activates binding between (i) T cell receptor (TCR) on the surface of the CD8$^+$ T cell and (ii) a type B self peptide presented by HLA-E on the surface of the HLA-E$^+$ T cell, thereby enhancing or activating down-regulation of the antigen-activated HLA-E$^+$ T cell.

In embodiments, the HLA-E$^+$ T cell is a CD4$^+$/HLA-E$^+$ T cell, the HLA-E$^+$ T cell is a CD8$^+$/HLA-E$^+$ T cell, the type B self peptide is Hsp60sp peptide. In a further embodiment the Hsp60sp peptide comprises consecutive amino acids having the sequence set forth in SEQ ID NO:2. In a further embodiment the peptide has the sequence Xaa-Met/Leu-Xaa-Xaa-Xaa-Xaa-Xaa-Xaa-Leu (SEQ ID NO:15). In a further embodiment the peptide is a nonomer which binds to HLA-E. In a further embodiment the peptide does not bind to the CD94/NKG2A receptor. In a further embodiment the peptide is recognized by the regulatory CD8+ T cells when bound to HLA-E. In a further embodiment the peptide can compete with B7sp for binding to HLA-E.

In embodiments, the agent is a dendritic cell-derived, HLA-E-bearing exosome loaded with type B self peptide, the agent is a dendritic cell-derived, HLA-E-bearing exosome loaded with Hsp60sp peptide, the agent is an HLA-E/IgG fusion protein, the agent is an HLA-E tetramer or an HLA-E/Hsp60sp tetramer. Fusion proteins are described in U.S. Pat. Nos. 5,116,964 and 5,336,603, which are hereby incorporated by reference. HLA-E tetramers are described in, for example, Braud et al., Nature. 1998 Feb. 19; 391(6669):740-1, 743; and in Garcia et al., Eur. J. Immunol. 2002 April; 32(4):936-44, both of which are hereby incorporated by reference. HLA-E protein sequences are described by NCBI accession nos. CAA05527, CAA40172, BAB63328, and BAF31260.

A method is provided for enhancing or activating down-regulation of an antigen-activated T cell by a Qa-1-dependent CD8+ T cell comprising contacting the Qa-1+ T cell and CD8+ T cell with an agent which enhances or activates binding between (i) T cell receptor (TCR) on the surface of the CD8+ T cell and (ii) a type B self peptide presented by Qa-1 on the surface of the Qa-1+ T cell, thereby enhancing or activating down-regulation of the antigen-activated Qa-1+ T cell. In a further embodiment the peptide has the sequence Xaa-Met/Leu-Xaa-Xaa-Xaa-Xaa-Xaa-Xaa-Leu (SEQ ID NO:15). In a further embodiment the peptide is a nonomer which binds to Qa-1. In a further embodiment the peptide does not bind to the CD94/NKG2A receptor. In a further embodiment the peptide is recognized by regulatory CD8+ T cells when bound to the Qa-1. In a further embodiment the peptide can compete with Qdm for binding to Qa-1.

In embodiments, the Qa-1+ T cell is a CD4+/Qa-1+ T cell, the Qa-1+ T cell is a CD8+/Qa-1+ T cell, the type B self peptide is Hsp60sp peptide. In a further embodiment, the Hsp60sp peptide comprises consecutive amino acids having the sequence set forth in SEQ ID NO:2. In embodiments, the agent is a dendritic cell-derived, Qa-1-bearing exosome loaded with type B self peptide; the agent is a dendritic cell-derived, Qa-1-bearing exosome loaded with Hsp60sp peptide. In a further embodiment, the Hsp60sp peptide comprises consecutive amino acids having the sequence set forth in SEQ ID NO:2.

In embodiments, the agent is a Qa-1/IgG fusion protein, the agent is a Qa-1 tetramer or Qa-1/Hsp60sp tetramer. Qa-1 tetramers are described in, for example, Salcedo et al., Eur. J. Immunol. 2000 April; 30(4):1094-101, which is hereby incorporated by reference.

A method is provided for enhancing or activating down-regulation of antigen-activated HLA-E+ T cells by HLA-E-dependent or HLA-E-restricted CD8+ T cells in a human subject comprising administering to the subject an effective amount of an agent which enhances or activates binding between (i) a T cell receptor (TCR) on the surface of an HLA-E-restricted or HLA-E-dependent CD8+ T cell and (ii) a type B self peptide presented by HLA-E on the surface of an HLA-E+ T cell, thereby enhancing or activating down-regulation of antigen-activated HLA-E+ T cells in the subject.

In embodiments, the HLA-E+ T cell is a CD4+/HLA-E+ T cell, the HLA-E+ T cell is a CD8+/HLA-E+ T cell, the type B self peptide is Hsp60sp peptide. In a further embodiment, the Hsp60sp peptide comprises consecutive amino acids having the sequence set forth in SEQ ID NO:2. In embodiments, the agent is (i) a dendritic cell-derived, HLA-E-bearing exosome loaded with type B self peptide, or (ii) an HLA-E-bearing membrane-bounded composition loaded with type B self peptide; the agent is (i) a dendritic cell-derived, HLA-E-bearing exosome loaded with Hsp60sp peptide, or (ii) an HLA-E-bearing membrane-bounded composition loaded with Hsp60sp peptide. In further embodiments, the Hsp60sp peptide comprises consecutive amino acids having the sequence set forth in SEQ ID NO:2. In embodiments, the agent is a Qa-1/IgG fusion protein, the agent is a Qa-1/Hsp60sp tetramer, the agent is administered intravenously, intramuscularly or orally.

A method is provided for enhancing or activating down-regulation of antigen-activated Qa-1+ T cells by Qa-1-dependent CD8+ T cells in a non-human subject comprising administering to the subject an effective amount of an agent which enhances or activates binding between (i) a T cell receptor (TCR) on the surface of a Qa-1-dependent CD8+ T cell and (ii) a type B self peptide presented by Qa-1 on the surface of a Qa-1+ T cell, thereby enhancing or activating down-regulation of the antigen activated Qa-1+ T cells in the subject.

In embodiments, the Qa-1+ T cell is a CD4+/Qa-1+ T cell, the Qa-1+ T cell is a CD8+/Qa-1+ T cell, the type B self peptide is Hsp60sp peptide. In further embodiments, the Hsp60sp peptide comprises consecutive amino acids having the sequence set forth in SEQ ID NO:2. In embodiments, the agent is a dendritic cell-derived, Qa-1-bearing exosome loaded with type B self peptide, or a Qa-1-bearing membrane-bounded composition loaded with type B self peptide; the agent is a dendritic cell-derived, Qa-1-bearing exosome loaded with Hsp60sp peptide or a Qa-1-bearing membrane-bounded composition loaded with Hsp60sp peptide. In a further embodiment, the Hsp60sp peptide comprises consecutive amino acids having the sequence set forth in SEQ ID NO:2. In embodiments, the agent is administered intravenously, intramuscularly or orally.

A method is provided for treating a human subject afflicted with a disorder selected from the group consisting of an autoimmune disease, graft transplant rejection and bacterial infection comprising administering to the subject a therapeutically effective amount of an agent which enhances or activates binding between (i) a T cell receptor (TCR) on the surface of an HLA-E-dependent or HLA-E-restricted CD8+ T cell and (ii) a type B self peptide presented by HLA-E on the surface of an HLA-E+ T cell, thereby treating the subject.

In embodiments, the HLA-E+ T cell is a CD4+/HLA-E+ T cell, the HLA-E+ T cell is a CD8+/HLA-E+ T cell, the type B self peptide is Hsp60sp peptide. In a further embodiment, the Hsp60sp peptide comprises consecutive amino acids having the sequence set forth in SEQ ID NO:2. In an embodiment, the autoimmune disease is rheumatoid arthritis, multiple sclerosis, type 1 diabetes, psoriasis, scleroderma, systemic lupus erythematosus. In embodiments the autoimmune disease is alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis—juvenile, discoid lupus, essential mixed cryoglobulinemia, fibromyalgia—fibromyositis, Grave's disease, Guillain-Barre, Hashimoto's thyroiditis, idiopathic pulmonary fibrosis, idiopathic thrombocytopenia purpura (ITP), IGA nephropathy, insulin dependent diabetes (type I), juvenile arthritis, lupus, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, takayasu arteritis, temporal arteritis/giant cell arteritis, ulcerative colitis, uveitis, vasculitis, vitiligo, Wegener's granulomatosis.

In embodiments, the agent is a dendritic cell-derived, HLA-E-bearing exosome loaded with type B self peptide, or an HLA-E-bearing membrane-bounded composition loaded with type B self peptide. In embodiments, the agent is a dendritic cell-derived, HLA-E-bearing exosome loaded with Hsp60sp peptide, or an HLA-E-bearing membrane-bounded composition loaded with Hsp60sp peptide. In a further embodiment, the Hsp60sp peptide comprises consecutive amino acids having the sequence set forth in SEQ ID NO:2. In embodiments, the agent is an HLA-E/IgG fusion protein, the agent is a HLA-E/Hsp60sp tetramer. In an embodiment, the agent is administered intravenously, intramuscularly or orally.

A method is provided for inhibiting in a human subject the onset of a disorder selected from the group consisting of an autoimmune disease, graft transplant rejection and bacterial infection comprising administering to the subject a prophylactically effective amount of an agent which enhances or activates binding between (i) a T cell receptor (TCR) on the surface of an HLA-E-dependent or HLA-E-restricted CD8+ T cell and (ii) a type-B self peptide presented by HLA-E on the surface of an HLA-E+ T cell, thereby treating the subject.

In embodiments, the HLA-E+ T cell is a CD4+/HLA-E+ T cell, the HLA-E+ T cell is a CD8+/HLA-E+ T cell, the type B self peptide is Hsp60sp peptide. In an embodiment, the autoimmune disease is selected from the group consisting of rheumatoid arthritis, multiple sclerosis and type 1 diabetes. In an embodiment, the agent is a dendritic cell-derived, HLA-E-bearing exosome loaded with type B self peptide, or an HLA-E-bearing membrane-bounded composition loaded with type B self peptide. In embodiments, the agent is (i) a dendritic cell-derived, HLA-E-bearing exosome loaded with Hsp60sp peptide, or (ii) an HLA-E-bearing membrane-bounded composition loaded with Hsp60sp peptide.

In embodiments, the agent is a HLA-E/IgG fusion protein, the agent is a HLA-E/Hsp60sp tetramer. In an embodiment, the agent is administered intravenously, intramuscularly or orally.

A dendritic cell-derived, Qa-1-bearing exosome loaded with self peptide is provided. In an embodiment, the dendritic cell-derived, Qa-1-bearing exosome comprises self peptide. In an embodiment, the Qa-1 is expressed or present on the surface of the exosome.

In embodiments, the exosome is loaded with a type B self peptide, the exosome is loaded with Hsp60sp peptide.

A dendritic cell-derived, HLA-E-bearing exosome loaded with self peptide is provided. In an embodiment, the dendritic cell-derived, HLA-E-bearing exosome comprises self peptide. In an embodiment, the HLA-E is expressed or present on the surface of the exosome.

In embodiments, the exosome is loaded with a type B self peptide, the exosome is loaded with Hsp60sp peptide. In a further embodiment, the Hsp60sp peptide comprises consecutive amino acids having the sequence set forth in SEQ ID NO:2.

A membrane-bounded composition bearing Qa-1 and comprising type B self peptide is provided. In an embodiment the type B self peptide is Hsp60sp peptide.

A membrane-bounded composition bearing HLA-E and comprising type B self peptide is provided. In an embodiment the type B self peptide is Hsp60sp peptide.

A method is provided for inhibiting down-regulation of an antigen-activated HLA-E+ T cell by an HLA-E-dependent or HLA-E-restricted CD8+ T cell comprising contacting the HLA-E+ T cell and CD8+ T cell with an agent which inhibits binding between (i) T cell receptor (TCR) on the surface of the CD8+ T cell and (ii) a type B self peptide presented by HLA-E on the surface of the HLA-E+ T cell, thereby inhibiting down-regulation of the antigen-activated HLA-E+ T cell.

In embodiments, the HLA-E+ T cell is a CD4+/HLA-E+ T cell, the HLA-E+ T cell is a CD8+/HLA-E+ T cell, the type B self peptide is the leader sequence of Heat Shock Protein 60 (Hsp60sp peptide). In a further embodiment, the Hsp60sp peptide comprises consecutive amino acids having the sequence set forth in SEQ ID NO:2. In embodiments, the agent is an antibody which specifically binds to a complex comprising type B self peptide and HLA-E, the agent is an antibody which specifically binds to a complex comprising Hsp60sp peptide and HLA-E.

In embodiments of the antibodies described herein the antibody is a monoclonal antibody, the antibody is a humanized antibody.

An "antibody" shall include, without limitation, an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Methods for humanizing antibodies are well known to those skilled in the art. "Antibody" also includes, without limitation, a fragment or portion of any of the afore-mentioned immunoglobulin molecules and includes a monovalent and a divalent fragment or portion. Antibody fragments include, for example, Fc fragments and antigen-binding fragments (Fab).

"Monoclonal antibodies," also designated a mAbs, are antibody molecules whose primary sequences are essentially identical and which exhibit the same antigenic specificity. Monoclonal antibodies may be produced by hybridoma, recombinant, transgenic or other techniques known to those skilled in the art.

A "humanized" antibody refers to an antibody wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules, whereas some, most or all amino acids within one or more CDR regions are unchanged. Small additions, deletions, insertions, substitutions or modifications of amino acids are permissible as long as they do not abrogate the ability of the antibody to bind a given antigen. Suitable human immunoglobulin molecules include IgG1, IgG2, IgG3, IgG4, IgA, IgE and IgM molecules. A "humanized" antibody retains an antigenic specificity similar to that of the original antibody.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. No. 5,585,089 (73) and U.S. Pat. No. 5,693,761 (74) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (75) also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. The affinity and/or specificity of the binding of the humanized antibody may be increased using methods of directed evolution as described in Wu et al. (1999) J. Mol. Biol. 284:151 and U.S. Pat. Nos. 6,165,793; 6,365,408 and 6,413,774.

A method for inhibiting down-regulation of an antigen-activated Qa-1$^+$ T cell by a Qa-1-dependent CD8$^+$ T cell is provided comprising contacting the Qa-1$^+$ T cell and CD8$^+$ T cell with an agent which inhibits binding between (i) T cell receptor (TCR) on the surface of the CD8$^+$ T cell and (ii) a type B self peptide presented by Qa-1 on the surface of the Qa-1$^+$ T cell, thereby inhibiting down-regulation of the antigen-activated Qa-1$^+$ T cell.

In embodiments, the Qa-1$^+$ T cell is a CD4$^+$/Qa-1$^+$ T cell, the Qa-1$^+$ T cell is a CD8$^+$/Qa-1$^+$ T cell, the type B self peptide is Hsp60sp peptide, the agent is an antibody which specifically binds to a complex comprising type B self peptide and Qa-1, the agent is an antibody which specifically binds to a complex comprising Hsp60sp peptide and Qa-1.

A method for inhibiting down-regulation of antigen-activated HLA-E$^+$ T cells by HLA-E-dependent CD8$^+$ T cells in a human subject is provided comprising administering to the subject an effective amount of an agent which inhibits binding between (i) a T cell receptor (TCR) on the surface of an HLA-E-dependent CD8$^+$ T cell and (ii) a type B self peptide presented by HLA-E on the surface of an HLA-E$^+$ T cell, thereby inhibiting down-regulation of antigen-activated HLA-E$^+$ T cells in the subject.

In embodiments, the HLA-E$^+$ T cell is a CD4$^+$/HLA-E$^+$ T cell, the HLA-E$^+$ T cell is a CD8$^+$/HLA-E$^+$ T cell, the type B self peptide is Hsp60sp peptide. In a further embodiment, the Hsp60sp peptide comprises consecutive amino acids having the sequence set forth in SEQ ID NO:2. In embodiments, the agent is an antibody which specifically binds to a complex comprising type B self peptide and HLA-E, the agent is an antibody which specifically binds to a complex comprising Hsp60sp peptide and HLA-E, the agent is administered intravenously, intramuscularly or orally.

A method for treating a human subject afflicted with a disorder characterized by excessive CD8$^+$ T cell-mediated immunosuppression is provided comprising administering to the subject a therapeutically effective amount of an agent which inhibits binding between (i) a T cell receptor (TCR) on the surface of an HLA-E-dependent CD8$^+$ T cell and (ii) a type B self peptide presented by HLA-E on the surface of an HLA-E$^+$ T cell, thereby treating the subject.

In embodiments, the HLA-E$^+$ T cell is a CD4$^+$/HLA-E$^+$ T cell, the HLA-E$^+$ T cell is a CD8$^+$/HLA-E$^+$ T cell, the type B self peptide is Hsp60sp peptide, the agent is an antibody which specifically binds to a complex comprising type B self and HLA-E, the agent is an antibody which specifically binds to a complex comprising Hsp60sp peptide and HLA-E. In embodiments, the subject is afflicted with AIDS, the subject is afflicted with a tumor, the subject has previously undergone treatment with a tumor vaccine or autologous T cell therapy. In an embodiment, the agent is administered intravenously, intramuscularly or orally.

An isolated antibody is provided which specifically binds to a type B self peptide presented by Qa-1. In an embodiment the antibody specifically binds to Hsp60sp peptide presented by Qa-1. In a further embodiment, the Hsp60sp peptide comprises consecutive amino acids having the sequence set forth in SEQ ID NO:2. In an embodiment, the antibody is a monoclonal antibody.

An isolated antibody is provided which specifically binds to a complex comprising type B self peptide and Qa-1. In an embodiment the type B self peptide is Hsp60sp peptide.

An isolated antibody which specifically binds to a type B self peptide presented by HLA-E is provided. In an embodiment, the antibody specifically binds to Hsp60sp peptide presented by HLA-E. In a further embodiment, the Hsp60sp peptide comprises consecutive amino acids having the sequence set forth in SEQ ID NO:2. In an embodiment, the antibody is a monoclonal antibody.

An isolated antibody which specifically binds to a complex comprising type B self peptide and HLA-E is provided. In an embodiment, the type B self peptide is Hsp60sp peptide.

An isolated antibody is provided which binds to an HLA-E/type B peptide complex so as to enhance or activate binding between (i) T cell receptor (TCR) on the surface of a $CD8^+$ T cell and (ii) a type B self peptide presented by HLA-E on the surface of the HLA-$E^+$ T cell, thereby enhancing or activating down-regulation of an antigen-activated HLA-$E^+$ T cell.

A composition is provided consisting essentially of membrane-bound or lipid solublized HLA-E and a type B self peptide bound thereto. In an embodiment, the type B self peptide is Hsp60sp peptide. In a further embodiment, the Hsp60sp peptide comprises consecutive amino acids having the sequence set forth in SEQ ID NO:2.

A composition consisting essentially of (i) a membrane-bound or lipid solublized HLA-E and a type B self peptide bound thereto, and (ii) a pharmaceutically acceptable carrier is provided.

A composition consisting essentially of membrane-bound or lipid solublized Qa-1 and a type B self peptide bound thereto is provided. In an embodiment, the type B self peptide is Hsp60sp peptide. In a further embodiment, the Hsp60sp peptide comprises consecutive amino acids having the sequence set forth in SEQ ID NO:2.

A composition consisting essentially of (i) a membrane-bound or lipid solubilized Qa-1 and a self peptide bound thereto, and (ii) a pharmaceutically acceptable carrier is provided. A composition comprising a pharmaceutically acceptable carrier and an antibody which specifically binds to a type B self peptide presented by Qa-1 is provided. In an embodiment, the type B self peptide is Hsp60sp peptide. A composition comprising a pharmaceutically acceptable carrier and an antibody which specifically binds to a type B self peptide presented by HLA-E is provided. In an embodiment, the type B self peptide is Hsp60sp peptide. In a further embodiment, the Hsp60sp peptide comprises consecutive amino acids having the sequence set forth in SEQ ID NO:2.

A composition containing a described exosome and a pharmaceutically acceptable carrier is provided. A composition containing a described exosome and a pharmaceutically acceptable carrier is provided.

A method for determining if a $CD8^+$ T cell is a Qa-1-dependent $CD8^+$ T cell is provided comprising contacting the $CD8^+$ T cell with a type-B self peptide presented by Qa-1, and determining whether binding occurs between the $CD8^+$ T cell and the type B self peptide, whereby binding indicates that the $CD8^+$ T cell is a Qa-1-dependent $CD8^+$ T cell.

In an embodiment, the type B self peptide is Hsp60sp peptide. In an embodiment, the Hsp60sp peptide comprises consecutive amino acids having the sequence set forth in SEQ ID NO:2. In an embodiment, the type B self peptide is presented by Qa-1 present on (i) a dendritic cell-derived, Qa-1-bearing exosome or (ii) a Qa-1-bearing membrane-bounded composition.

A method for determining if a $CD8^+$ T cell is an HLA-E-dependent $CD8^+$ T cell is provided comprising contacting the $CD8^+$ T cell with a type B self peptide presented by HLA-E, and determining whether binding occurs between the $CD8^+$ T cell and the type B self peptide, whereby binding indicates that the $CD8^+$ T cell is an HLA-E-dependent $CD8^+$ T cell.

In an embodiment, the type B self peptide is Hsp60sp peptide. In an embodiment, wherein the Hsp60sp peptide comprises consecutive amino acids having the sequence set forth in SEQ ID NO:2. In an embodiment, the type B self peptide is presented by HLA-E present on (i) a dendritic cell-derived, HLA-E-bearing exosome or (ii) an HLA-E-bearing membrane-bounded composition.

A method for isolating Qa-1-dependent $CD8^+$ T cells present in a T cell-containing sample is provided comprising:
 (a) contacting the sample with an immobilized Qa-1-presented type B self peptide under conditions permitting binding of the type B self peptide with Qa-1-dependent $CD8^+$ T cells in the sample;
 (b) removing unbound T cells; and
 (c) dissociating from the immobilized type B self peptide any bound Qa-1-dependent $CD8^+$ T cells,
 thereby isolating Qa-1-dependent $CD8^+$ T cells from the sample.

In an embodiment, the type B self peptide comprises the signal peptide of Heat Shock Protein60 as set forth in SEQ ID NO:2.

A method for isolating HLA-E-dependent $CD8^+$ T cells present in a T cell-containing sample is provided comprising:
 (a) contacting the sample with immobilized HLA-E-presented type B self peptide under conditions permitting binding of the type B self peptide with HLA-E-dependent $CD8^+$ T cells in the sample;
 (b) removing unbound T cells; and
 (c) dissociating from the immobilized type B self peptide any bound HLA-E-dependent $CD8^+$ T cells,
 thereby isolating HLA-E-dependent $CD8^+$ T cells from the sample.

In an embodiment, the type B self peptide comprises the leader sequence of Heat Shock Protein60 as set forth in SEQ ID NO:2.

In each of the above embodiments describing Hsp60sp, a structurally related peptide can be employed in place of the Hsp60sp.

A method of identifying an agent as an enhancer of down-regulation of antigen-activated intermediate avidity Qa-$1^+$ T cells by Qa-1-dependent $CD8^+$ T cells is provided comprising:
a) providing an antigen-activated Qa-$1^+$ T cell and a Qa-1-dependent $CD8^+$ T cell;
b) contacting the antigen-activated Qa-$1^+$ T cell with the Qa-1-dependent $CD8^+$ T cell;
c) quantitating down-regulation of the antigen-activated Qa-$1^+$ T cell;
d) repeating steps b) and C) in the presence of the agent
e) comparing the down-regulation quantitated in step d) with the down-regulation quantitated in step c),
wherein down-regulation quantitated in step d) greater than that quantitated in step c) indicates that the agent is an enhancer of down-regulation of antigen-activated intermediate avidity Qa-$1^+$ T cells by Qa-1-dependent $CD8^+$ T cells.

A method of identifying an agent as an enhancer of down-regulation of antigen-activated intermediate avidity HLA-$E^+$ T cells by HLA-E-dependent $CD8^+$ T cells is provided comprising:
a) providing an antigen-activated HLA-$E^+$ T cell and a HLA-E-dependent $CD8^+$ T cell;
b) contacting the activated HLA-$E^+$ T cell with the HLA-E-dependent $CD8^+$ T cell;
c) quantitating down-regulation of the activated HLA-$E^+$ T cell;
d) repeating steps b) and C) in the presence of the agent; and
e) comparing the down-regulation quantitated in step d) with the down-regulation quantitated in step c), wherein down-regulation quantitated in step d) greater than that quantitated in step c) indicates that the agent is an enhancer of down-regulation of antigen-activated intermediate avidity HLA-E$^+$ T cells by HLA-E-dependent CD8$^+$ T cells.

A method of identifying an agent as an inhibitor of down-regulation of intermediate avidity antigen-activated Qa-1$^+$ T cells by Qa-1-dependent CD8$^+$ T cells is provided comprising:
a) providing an activated Qa-1$^+$ T cell and a Qa-1-dependent CD8$^+$ T cell;
b) contacting the activated Qa-1$^+$ T cell with the Qa-1-dependent CD8$^+$ T cell;
c) quantitating down-regulation of the activated Qa-1$^+$ T cell;
d) repeating steps b) and C) in the presence of the agent; and
e) comparing the down-regulation quantitated in step d) with the down-regulation quantitated in step c),
wherein down-regulation quantitated in step d) less than that quantitated in step c) indicates that the agent is an inhibitor of down-regulation of intermediate avidity antigen-activated Qa-1$^+$ T cells by Qa-1-dependent CD8$^+$ T cells.

A method of identifying an agent as an inhibitor of down-regulation of intermediate avidity antigen-activated HLA-E$^+$ T cells by HLA-E-dependent CD8$^+$ T cells is provided comprising:
a) providing an activated HLA-E$^+$ T cell and a HLA-E-dependent CD8$^+$ T cell;
b) contacting the activated HLA-E$^+$ T cell with the HLA-E-dependent CD8$^+$ T cell;
c) quantitating down-regulation of the activated HLA-E$^+$ T cell;
d) repeating steps b) and C) in the presence of the agent; and
e) comparing the down-regulation quantitated in step d) with the down-regulation quantitated in step c),
wherein down-regulation quantitated in step d) less than that quantitated in step c) indicates that the agent is an inhibitor of down-regulation of intermediate avidity antigen-activated HLA-E$^+$ T cells by HLA-E-dependent CD8$^+$ T cells.

In an embodiment the HLA-E$^+$ T cells are human HLA-E$^+$ T cells. In an embodiment, the HLA-E+ T cells are human HLA-E+ T cells. In an embodiment, the agent is a nonomer peptide. In an embodiment, the nonomer peptide has a methionine or a leucine at P2 and a leucine at P9.

This invention also provides a method of inhibiting down-regulation of an antigen-activated HLA-E$^+$ T cell by an HLA-E-dependent or HLA-E-restricted CD8$^+$ T cell comprising introducing a nucleic acid into the HLA-E$^+$ T cell or CD8$^+$ T cell so as to inhibit binding between (i) T cell receptor (TCR) on the surface of the CD8$^+$ T cell and (ii) a type B self peptide presented by HLA-E on the surface of the HLA-E$^+$ T cell, thereby inhibiting down-regulation of the antigen-activated HLA-E$^+$ T cell. In one embodiment, the nucleic acid is siRNA. In another embodiment, the siRNA is a single-stranded, hairpin siRNA. In another embodiment, the siRNA is a double-stranded siRNA. In one embodiment, the nucleic acid is a DNAzyme. In another embodiment, the nucleic acid is a ribozyme. In another embodiment, the nucleic acid is an anti-sense molecule. In one embodiment the nucleic acid inhibits expression of HLA-E. In another embodiment the nucleic acid inhibits expression of T cell receptor. In another embodiment the nucleic acid inhibits expression of the type B self peptide.

This invention also provides a method of inhibiting down-regulation of an antigen-activated Qa-1$^+$ T cell by an Qa-1-dependent CD8$^+$ T cell comprising introducing a nucleic acid into the Qa-1$^+$ T cell or CD8$^+$ T cell so as to inhibit binding between (i) T cell receptor (TCR) on the surface of the CD8$^+$ T cell and (ii) a type B self peptide presented by Qa-1 on the surface of the Qa-1$^+$ T cell, thereby inhibiting down-regulation of the antigen-activated Qa-1$^+$ T cell. In one embodiment, the nucleic acid is siRNA. In another embodiment, the siRNA is a single-stranded, hairpin siRNA. In another embodiment, the siRNA is a double-stranded siRNA. In one embodiment, the nucleic acid is a DNAzyme. In another embodiment, the nucleic acid is a ribozyme. In another embodiment, the nucleic acid is an anti-sense molecule. In one embodiment the nucleic acid inhibits expression of Qa-1. In another embodiment the nucleic acid inhibits expression of T cell receptor. In another embodiment the nucleic acid inhibits expression of the type B self peptide.

In an embodiment the described siRNA comprises a sense strand and an antisense strand. RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire, A. et al. (1998), Nature 391: 806-811). These short dsRNA molecules, called "short interfering RNA" or "siRNA," cause the destruction of messenger RNAs ("mRNAs") which share sequence homology with the siRNA to within one nucleotide resolution (Elbashir, S. M. et al. (2001), Genes Dev, 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Elbashir, S. M. et al. (2001), supra, has shown that synthetic siRNA of 21 and 22 nucleotides in length, and which have short 3' overhangs, are able to induce RNAi of target mRNA in a *Drosophila* cell lysate. Cultured mammalian cells also exhibit RNAi degradation with synthetic siRNA (Elbashir, S. M. et al. (2001) Nature, 411: 494-498), and RNAi degradation induced by synthetic siRNA has recently been shown in living mice (McCaffrey, A. P. et al. (2002), Nature, 418: 38-39: Xia, H. et al. (2002), Nat. Biotech., 20: 1006-1010). The therapeutic potential of siRNA-induced RNAi degradation has been demonstrated in several recent in vitro studies, including the siRNA-directed inhibition of HIV-1 infection (Novina, C. D. et al. (2002), Nat. Med. 8: 681-686) and reduction of neurotoxic polyglutamine disease protein expression (Xia, H. et al. (2002), supra). In an embodiment the siRNA is 21 or 22 nucleotides in length. Methods and compositions for gene silencing techniques are described in U.S. Pat. Nos. 6,573,099; 6,506,599; 7,109,165; 7,022,828; 6,995,259; 6,617,438; 6,673,611; 6,849,726; and 6,818,447, which are hereby incorporated by reference.

A method is provided of selectively activating a HLA-E-restricted regulatory CD8+ T cell comprising contacting the HLA-E-restricted regulatory CD8+ T cell with an HLA-E/Hsp60sp tetramer or an HLA-e/IgG fusion protein so as to thereby selectively activate the HLA-E-restricted regulatory CD8+ T cell.

In an embodiment, the HLA-E-restricted CD8+ T cell is contacted with an HLA-E/Hsp60sp tetramer. In an embodiment, the HLA-E-restricted CD8+ T cell is contacted with an HLA-e/IgG fusion protein.

A method is provided of inhibiting an antigen-activated HLA-E+ T cell comprising contacting an HLA-E-restricted CD8+ T cell with an HLA-E/Hsp60sp tetramer or an HLA-e/IgG fusion protein so as to activate the HLA-E-restricted CD8+ T cell and thereby inhibit the HLA-E+ T cell.

In an embodiment, the HLA-E-restricted CD8+ T cell is contacted with an HLA-E/Hsp60sp tetramer. In an embodiment, the HLA-E-restricted CD8+ T cell is contacted with an HLA-E/IgG fusion protein.

A method is provided of treating an autoimmune disease in a subject comprising administering to the subject an amount of an agent effective to activate an HLA-E-restricted CD8+ T cell so as to thereby inhibit an activated HLA-E+ T cell in the subject and thereby treat the autoimmune disease.

In an embodiment, the agent is an HLA-E/Hsp60sp tetramer or an HLA-E/IgG fusion protein.

A method is provided of determining the efficacy of an autoimmune disease treatment comprising:
a) quantifying the activated HLA-E+ T cells in a first sample obtained from the subject before treatment;
b) treating the subject with the autoimmune disease treatment;
c) quantifying the activated HLA-E+ T cells in a second sample obtained from the subject after treatment;
d) comparing the level of activated HLA-E+ T cells quantified in steps a) and c) wherein a lower level quantified in step c) than step a) indicates that the autoimmune disease treatment is efficacious.

In an embodiment, the autoimmune disease is rheumatoid arthritis, multiple sclerosis, type 1 diabetes, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, crest syndrome, Crohn's disease, Dego's disease, dermatomyositis, juvenile dermatomyositis, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, lupus, Meniere's disease, mixed connective tissue disease, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiffman syndrome, takayasu arteritis, temporal arteritis/giant cell arteritis, ulcerative colitis, uveitis, vasculitis, vitiligo, or Wegener's granulomatosis.

In an embodiment, the activated HLA-E+ T cells are quantified by contacting the sample with an HLA-E/Hsp60sp tetramer or an HLA-E/IgG fusion protein and quantifying the binding of the HLA-E+ T cells to the HLA-E/Hsp60sp tetramer or to the HLA-E/IgG fusion protein. In an embodiment, the HLA-E/Hsp60sp tetramer or the HLA-E/IgG is immobilized. In an embodiment, the samples are derived from the subject's blood or derived from the subject's lymph.

In embodiments of all of the methods described hereinabove employing antigen-activated HLA-E+ T cell(s) and/or HLA-E-restricted CD8+ T cell(s) the cell or cells are human. In embodiments of the methods described hereinabove the subject is a human.

The methods disclosed herein permit control and/or amelioration of autoimmune diseases that can be achieved independent of the knowledge of the particular self-antigens involved in the given autoimmune disease due to the common target structure(s). Thus, even without identification of the target antigen of the autoimmune disease, the disease can be treated.

A process of manufacturing a pharmaceutical for treating an autoimmune disease is provided comprising:
c) identifying an agent that enhances binding between an HLA-E-restricted $CD8^+$ T cell and an antigen-activated $HLA-E^+$ T cell; and
d) admixing the agent identified in step a) with a pharmaceutically acceptable carrier so as to thereby manufacture the pharmaceutical.

In an embodiment of the process, in step a) the agent is identified as enhancing binding by i) providing an antigen-activated HLA-E+ T cell and a HLA-E-restricted CD8+ T cell; ii) contacting the activated HLA-E+ T cell with the HLA-E-restricted CD8+ T cell; iii) quantitating down-regulation of the activated HLA-E+ T cell; iv) repeating steps ii) and iii) in the presence of the agent; v) comparing the down-regulation quantitated in step iv) with the down-regulation quantitated in step iii), wherein down-regulation quantitated in step iv) greater than that quantitated in step iii) identifies the agent an enhancer of down-regulation of antigen-activated HLA-E+ T cells by HLA-E-restricted CD8+ T cells.

A process of manufacturing a pharmaceutical for enhancing an immune response mediated by intermediate avidity antigen-activated $HLA-E^+$ T cell is provided comprising:
e) identifying an agent that inhibits binding between an HLA-E-restricted $CD8^+$ T cell and an antigen-activated $HLA-E^+$ T cell; and
f) admixing the agent identified in step a) with a pharmaceutically acceptable carrier so as to thereby manufacture the pharmaceutical.

In an embodiment of the process, in step a) the agent is identified as inhibiting binding by i) providing an antigen-activated HLA-E+ T cell and a HLA-E-restricted CD8+ T cell; ii) contacting the activated HLA-E+ T cell with the HLA-E-restricted CD8+ T cell; iii) quantitating down-regulation of the activated HLA-E+ T cell; iv) repeating steps ii) and iii) in the presence of the agent; v) comparing the down-regulation quantitated in step iv) with the down-regulation quantitated in step iii), wherein down-regulation quantitated in step iv) less than that quantitated in step iii) identifies the agent an inhibitor of down-regulation of antigen-activated HLA-E+ T cells by HLA-E-restricted CD8+ T cells.

A vaccine composition is provided comprising a membrane-bound HLA-E or lipid-solublized HLA-E and a type B self peptide bound thereto. In an embodiment the type B self peptide is Hsp60sp peptide or a structurally related peptide. In a further embodiment the Hsp60sp peptide comprises consecutive amino acids having the sequence set forth in SEQ ID NO:2. In an embodiment the type B self peptide has the sequence set forth in SEQ ID NO:15, wherein Xaa at positions 1 and 3-8 are, independently, any amino acid.

A vaccine composition is provided comprising (i) a membrane-bound HLA-E or lipid-solublized HLA-E and a type B self peptide bound thereto, and (ii) a pharmaceutically acceptable carrier. In an embodiment the type B self peptide is Hsp60sp peptide or a structurally related peptide. In a further embodiment the Hsp60sp peptide comprises consecutive amino acids having the sequence set forth in SEQ ID NO:2. In an embodiment the type B self peptide has the sequence set forth in SEQ ID NO:15.

It is understood that the steps of the processes described hereinabove may be performed by different parties, and may be performed in different locations.

In the methods compositions and processes described hereinabove it is understood that an HLA-E/type b self peptide tetramer may be substituted for the recited HLA-E/Hsp60sp tetramer. In an embodiment the type b self peptide has the sequence set forth in SEQ ID NO:15.

Hsp60sp has the sequence QMRPVSRAL (SEQ ID NO:2).

All combinations of the various elements of methods, compositions and processes described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

It is known that the predominant peptide bound to Qa-1 is Qdm, a hydrophobic peptide derived from leader sequence of MHC Class Ia molecules (95-98). This peptide (AMAPRTLLL) (SEQ ID NO:1) binds with high affinity and accounts for the majority of the peptides associated with Qa-1 which complex to CD94/NKG2A on NK cells and inhibit NK activity (98,99). All Ga-1/HLA-E binding peptides are nonomers. The Qdm or Qdm-like peptides are defined as type A peptides. However, Qa-1 can also bind other self-peptides including those derived from heat shock proteins (100) and pre-proinsulin leader sequences (101). The Qa-1 binding peptides that do not bind to CD94/NKG2A (77) are classified as type B peptides.

Here, it is disclosed that a signal peptide from the leader sequence of Heat Shock Protein60 (Hsp60sp), presented by the MHC class Ib molecule, Qa-1, is a surrogate target structure, preferentially expressed at a higher level on the intermediate avidity T cells and specifically recognized by the Qa-1 dependent CD8+ T cells. Thus, as a unique mechanism, perceiving the avidity of T cell activation can be translated into peripheral T cell regulation in vivo, providing a new concept to understand how peripheral self-tolerance is maintained. The biological significance of this concept is demonstrated hereinbelow by the ability of Hsp60sp-loaded relevant dendritic cells (DCs) to induce a Qa-1 dependent CD8+ T cell mediated significant protection from autoimmune encephalopathy in the Experimental Allergic Encephalomyelitis (EAE) model.

Qa-1 dependent CD8+ T cells were initially identified as regulators which mediate the resistance to autoimmune Experimental Allergic Encephalomyelitis (EAE) induced by the first episode of the disease (3 and 4). It has been noted that more severe symptoms of EAE develop, in a much less controllable fashion, during the relapse of EAE in CD8−/− (4) or the re-induction of EAE in Qa-1−/− mice (5), indicating that these Qa-1 dependent CD8+ T cells play an important role in maintaining peripheral self-tolerance.

Intrathymic deletion of high avidity T cell clones, reactive to the majority of self-antigens, generates a truncated peripheral self-reactive repertoire composed of only intermediate and low avidity clones but devoid of high avidity clones compared with the foreign-reactive repertoire (6). Potentially pathogenic self-reactive T cells are included in the pool of the intermediate avidity thymic escapees that have avidity lower than the ones deleted in the thymus, but cover a wide range of avidity from a high end close to the threshold of thymic negative selection to a quite low end, under which thymic escapees can be activated in the periphery to initiate autoimmune diseases (7 and 8).

The resultant distinctive composition of peripheral T cell repertoires to self versus to foreign antigens provides a unique opportunity for the immune system to discriminate self from non-self, in the periphery, by selectively down-regulating intermediate avidity T cells to both self and foreign antigens. Selective down-regulation of intermediate avidity T cell populations containing the potentially pathogenic self-reactive T cells would enable the immune system to specifically control autoimmune disease without damaging the on going anti-infection immunity, which is largely mediated by high avidity T cells specific to the foreign pathogens.

It was hypothesized that the molecular and cellular mechanism that accounts for such action is the specific recognition by regulatory CD8+ T cells of particular Qa-1/self-peptide complexes expressed on target cells as a function of intermediate avidity T cell activation (1 and 2).

To test this hypothesis, it was crucial to identify the Qa-1 binding peptide/s that render the activated T cells susceptible to down-regulation by the Qa-1 dependent CD8+ T cells. It is known that the predominant peptide bound to the MHC Class Ib molecule Qa-1, is Qdm, a hydrophobic peptide derived from leader sequence of MHC Class Ia molecules (9 and 10). This peptide binds with high affinity and accounts for the majority of the peptides associated with Qa-1. Qa-1/Qdm interacts with CD94/NKG2A on NK cells and inhibits NK activity (11). Here, the Qdm or Qdm like peptides are classified as "type A" peptides. Type A peptides can interact with CD94/NKG2A when bound to Qa-1 or HLA-E and inhibit NK activity. Qa-1 can also bind other self-peptides, however, including those derived from heat shock proteins (12) and preproinsulin leader sequences (13). In this regard, human studies have shown that a signal peptide derived from the leader sequence of a stress protein Hsp60 (Hsp60sp) is capable of competing with B7sp peptide, the human counterpart of Qdm, for occupancy of HLA-E, the human counter part of Qa-1 (14). The resultant HLA-E/Hsp60sp complex does not interact with CD94/NKG2A and therefore is not capable of inhibiting the NK activity.

Herein, Qa-1 binding peptides that do not interact with CD94/NKG2A, when coupled with Qa-1, are classified as "type B" peptides. It was hypothesized that some of the type B Qa-1-binding peptides, capable of competing with Qdm for binding to Qa-1 may be preferentially expressed on the intermediate avidity T cells and serve as a specific target for the Qa-1 dependent regulatory CD8+ T cells.

Figure 1:
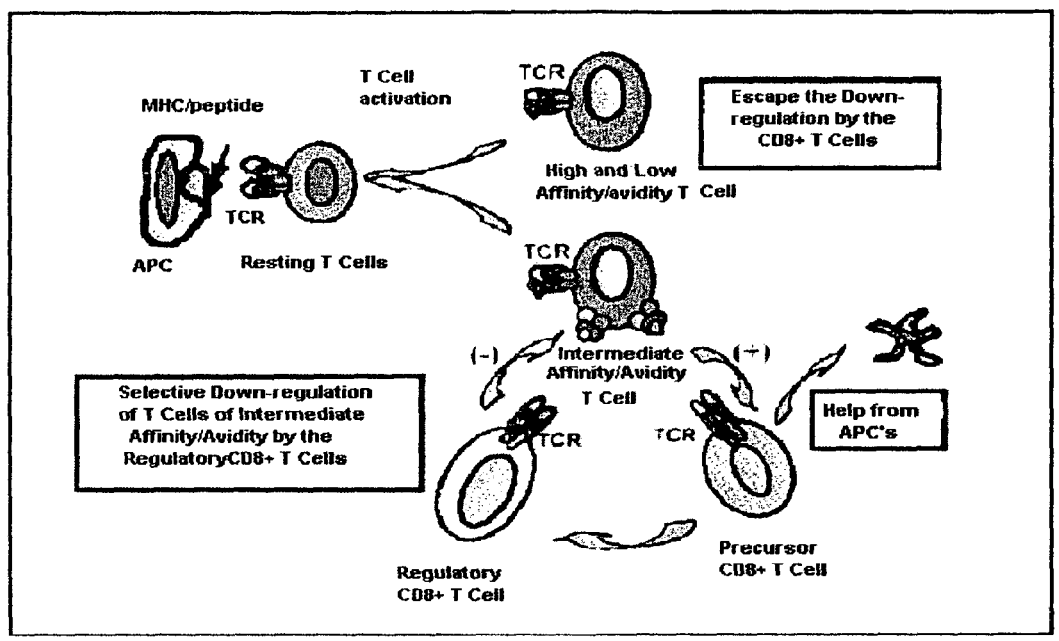
FIG. 1: The cellular events of Qa-1 dependent CD8+ T cell mediate pathway, initiated by the activation of naïve T cells during the primary immune response in which the TCRs on T cells interact with MHC/antigen peptide complexes presented by conventional APCs. One of the consequences of the initial T cell activation is the differential expression of a specific "target antigen", which, in this case, include the "Qa-1/self-peptide complex", on the surface of target T cells. Importantly, the expression of the "target antigen", which is recognized by the TCR on regulatory T cells, is determined by the avidity interactions of T cell activation, regardless of which antigen the target T cells are triggered by. In this regard, since T cells are not professional APCs, the professional APCs, such as dendritic cells may be recruited and function to provide co-stimulatory signals during the induction phase of the regulatory T cells. The "target antigen" expressed on certain activated T cells triggers the regulatory T cells to differentiate into effector cells, which in turn down-regulate any activated T cells expressing the same target antigen during the secondary immune response.
Figure 2:
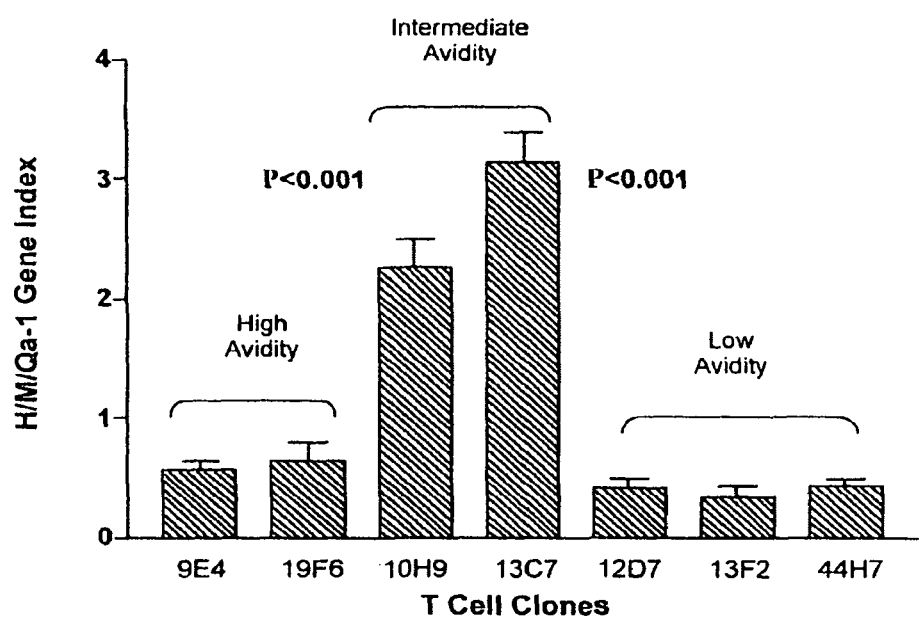
FIG. 2: H/M/Qa-1 Gene Indexes are significantly higher in intermediate avidity T cell clones than in high and low avidity clones. The Real time PCR was performed at 60 hours after the T cell clones were activated by 10 uM of specific antigen HEL as described (1). The figure summarizes three separate experiments. H/M/Qa-1 Gene Index is calculated as: [Hsp60 Gene Expression index/MHC Class Ia (H-2D$^d$) Gene Expression Index]×Qa-1 Gene Expression Index, which represents the ratio of Hsp60 versus MHC Class Ia (H-2D$^d$) normalized to Qa-1 at gene expression level. Gene Expression Index: the ratio of gene expression between a given gene and β-actin in the same cells. ED$_{50}$ (μM) of the clones are: 9E4 and 19F6<1 μM; 10H9, 3 μM; 13C7, 10 μM; 12D7, 13F2 and 44H7>20 μM.
Figure 3:
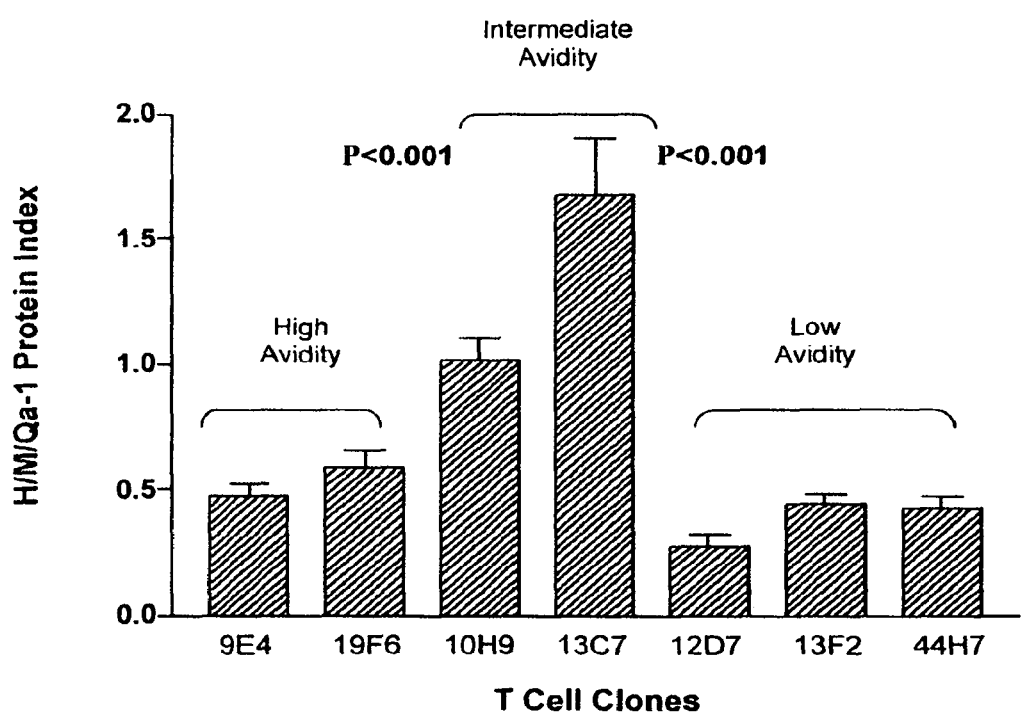
FIG. 3: H/M/Qa-1 Protein Indexes obtained by Western blotting assay. H/M/Qa-1 Protein Indexes are significantly higher in intermediate avidity T cell clones than in high and low avidity clones. The Western blotting assay was performed at 72 hours after the T cell clones were activated by 10 μM of specific antigen HEL as described (1). The figure summarizes three separate experiments. H/M/Qa-1 Protein Index is calculated as: [Hsp60 Protein Expression index/MHC Class Ia (H-2D$^d$) Protein Expression Index]×Qa-1 Protein Expression Index, which represents the ratio of Hsp60 versus MHC Class Ia (H-2D$^d$) normalized to Qa-1 at protein expression level. Protein Expression Index: the ratio of protein expression between a given protein and β-actin in the same cells.

A comparison was performed, at both mRNA and protein levels in T cell clones, of the expression of Qa-1 as well as the Hsp60 and MHC Class Ia (H-2D$^d$) molecules. These molecules are able to generate the Hsp60sp and Qdm (15) peptides, respectively, during T cell activation. A panel of HEL-specific T cell clones established from the Qa-1b strain Balb/c mice previously identified (1) were employed. FIGS. 2, 3 and Tables 1 and 2 list seven representative T cell clones chosen from the 28 HEL-specific clones to represent a range of avidity to HEL. As previously reported, the clones have different susceptibility to the down-regulation by the Qa-1 dependent CD8+ T cells (1).

Table 1 shows results from experiments where mice vaccinated with dendritic cells loaded with Hsp60sp, but not Qdm, are significantly protected from the subsequent induction of EAE. Control: Mice induced to develop EAE without vaccination. In experiments 3 and 4 mice were also treated with control Rat Ig, as control for anti-CD8 mAb 53-6.72, before EAE induction. DC w/Hsp60sp: Mice injected with DCs loaded with Hsp60sp peptide before EAE induction. DC w/Qdm: Mice injected with DCs loaded with Qdm peptide before EAE induction. CD8−/DC w/Hsp60sp: Mice were depleted of CD8+ T cells by injection of anti CD8 mAb 53-6.72, as described in the methods, one week after DC vaccination and three days before EAE induction.

dent CD8+ T cells selectively down-regulate T cells of intermediate but not high or low avidity (1). Importantly, there were no significant differences among H/M/Qa-1 Protein

TABLE 1

Comparisons of gene expression among HEL-specific clones in a real time PCR assay

| T cell Clone | Avidity | $ED_{50}$ (μm) | Gene Expression Index* | | | Hsp60/MHC Class Ia (H/M) | H/M/Qa-1 Gene Index ◇ |
|---|---|---|---|---|---|---|---|
| | | | Qa-1 | Hsp60 | MHC Class Ia ($H$-$2D^d$) | H/M Gene Expression ratio∞ | |
| 9E4 | High | <1 | 0.35 | 0.60 | 0.44 | 1.36 | 0.48 |
| 19F6 | High | <1 | 0.50 | 0.53 | 0.51 | 1.04 | 0.52 |
| 10H9 | Inter | 3 | 0.45 | 1.43 | 0.31 | 4.61 | 2.08 |
| 13C7 | Inter | 10 | 0.40 | 2.10 | 0.29 | 7.24 | 2.89 |
| 12D7 | Low | >20 | 0.42 | 0.46 | 0.56 | 0.82 | 0.35 |
| 13F2 | Low | >20 | 0.45 | 0.25 | 0.45 | 0.56 | 0.25 |
| 44H7 | Low | >20 | 0.46 | 0.35 | 0.61 | 0.57 | 0.26 |

Comparisons of gene expression among HEL-specific clones in real time PCR assay.
The Real time PCR was performed at 60 hours after the T cell clones were activated by 10 μM of specific antigen HEL as described (1). The Table represents one of three separate experiments.
*Gene Expression Index: the ratio of gene expression between a given gene and β-actin in the same cells.
∞H/M Gene Expression ratio is the ratio of Gene Expression Index between Hsp60 and MHC Class Ia ($H$-$2D^d$).
◇ H/M/Qa-1 Gene Index is calculated as H/M Gene Expression Ratio times Gene Expression Index of Qa-1, which represents the ratio of Hsp60 versus MHC Class Ia ($H$-$2D^d$) normalized to Qa-1 at gene expression level.

TABLE 2

Comparisons of protein expression among HEL-specific clones in a Western blotting assay

| T cell Clone | Avidity | $ED_{50}$ (μM) | Protein Expression Index* | | | Hsp60/MHC Class Ia (H/M) | H/M/Qa-1 Protein Index ◇ |
|---|---|---|---|---|---|---|---|
| | | | Qa-1 | Hsp60 | MHC Class Ia ($H$-$2D^d$) | H/M Protein Expression ratio∞ | |
| 9E4 | High | <1 | 0.54 | 0.68 | 0.58 | 1.17 | 0.63 |
| 19F6 | High | <1 | 0.53 | 0.75 | 0.66 | 1.14 | 0.60 |
| 10H9 | Inter | 3 | 0.57 | 1.07 | 0.45 | 2.34 | 1.35 |
| 13C7 | Inter | 10 | 0.54 | 1.18 | 0.37 | 3.19 | 1.72 |
| 12D7 | Low | >20 | 0.57 | 0.43 | 0.71 | 0.61 | 0.35 |
| 13F2 | Low | >20 | 0.54 | 0.44 | 0.57 | 0.77 | 0.42 |
| 44H7 | Low | >20 | 0.60 | 0.52 | 0.67 | 0.78 | 0.47 |

Comparisons of protein expression among HEL-specific clones in Western blotting assay.
The Western blotting assay was performed at 72 hours after the T cell clones were activated by 10 μm of specific antigen HEL as described (1). The table represents one of three separate experiments.
*Protein Expression Index: the ratio of protein expression between a given protein and β-actin in the same cells.
∞H/M protein Expression ratio is the ratio of protein Expression Index between Hsp60 and MHC Class Ia ($H$-$2D^d$).
◇ H/M/Qa-1 protein Index is calculated as H/M Protein Expression Ratio times Protein Expression Index of Qa-1, which represents the ratio of Hsp60 versus MHC Class Ia ($H$-$2D^d$) normalized to Qa-1 at protein expression level.

The ratio of the expression of Hsp60 versus MHC Class Ia was measured in relation to the expression of Qa-1 as a function of avidity of T cell activation and calculated the H/M/Qa-1 Gene or Protein Indexes to reflect the relative expression of Qa-1/Hsp60sp versus Qa-1/Qdm in each T cell clone tested.

Figure 4:
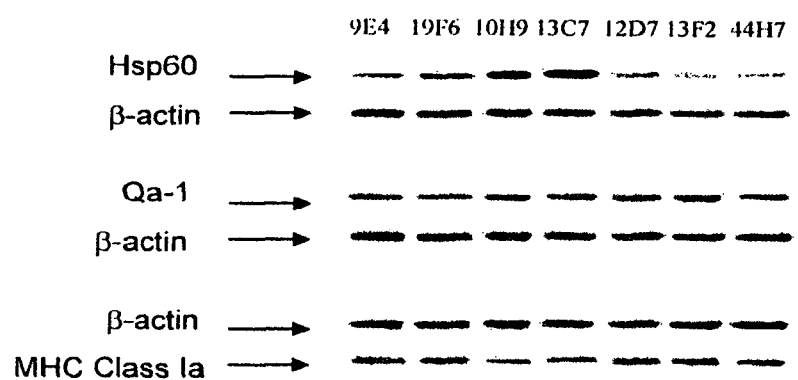
FIG. 4: Protein levels of Hsp60, MHC Class Ia and Qa-1 expressed in different HEL clones in Western blotting assay. The figure is representative of three separate experiments in FIG. 3.
Figure 5:
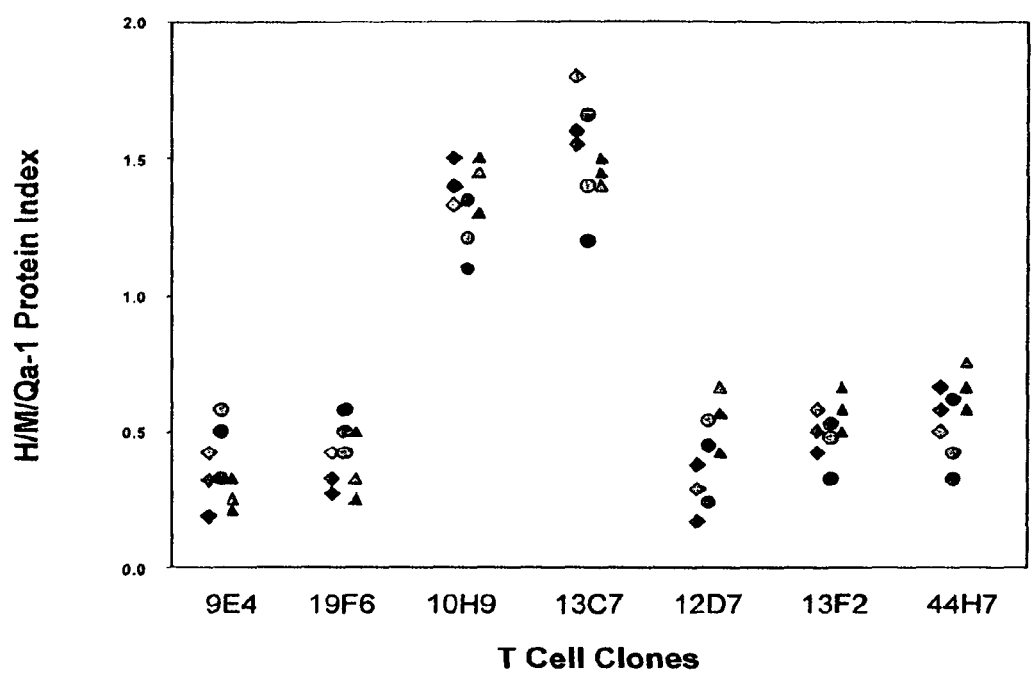
FIG. 5: There are no significant differences among H/M/Qa-1 Protein Indexes of T cell clones with known ED$_{50}$ activated by different doses of antigen HEL ranging from 1 uM to 50 μM. The figure summarizes three separate experiments. When H/M/Qa-1 Protein Indexes were compared for each clone stimulated with three doses (1, 10 and 50 μM), there was no significant differences for each clone tested (P>0.05), while significant differences between intermediate versus high and low avidity groups at all three doses were shown (P<0.001).

In a real time PCR assay, the H/M/Qa-1 Gene Index was significantly higher in the two intermediate avidity clones, 10H9 and 13C7, compared with the two high avidity clones 9E4 and 19F6 (P<0.001) as well as the three low avidity clones 12D7, 13F2 and 44H7 (P<0.001) (FIG. 2 and Table 1). Similarly, at the level of protein expression, the H/M/Qa-1 Protein Index was also significantly higher in the intermediate than in the high and low avidity clones in a Western blotting assay (FIGS. 3, 4 and Table 2). This set of results correlated with the particular pattern of T cell regulation observed in previous in vivo and in vitro studies showing that Qa-1 depen- Indexes obtained when the same clones were activated with different doses of antigen ranging from 1 μM to 50 μM (FIG. 5). Taken together, these observations support the hypothesis that a higher expression ratio between Qa-1/Hsp60sp and Qa-1/Qdm in T cells is a function of the intermediate avidity activation of T cell activation, which may determine the susceptibility of the T cells to the down-regulation by the Qa-1 dependent CD8+ T cells.

To further test this hypothesis, it was subsequently determined if Qa-1/Hsp60sp is indeed the specific target structure recognized by the regulatory CD8+ T cells in EAE susceptible Qa-1a strain B10PL in order to better understand the biology of Qa-1 dependent CD8+ T cells, at a molecular level, in the context of an autoimmune disease model. It is known that most of the differences between Qa-1a and Qa-1b are located peripheral to the binding cleft so that these two molecules associate with structurally similar peptides (16). Qdm (AMAPRTLLL) (SEQ ID NO:1) was used as a model "type A" peptide in the studies to evaluate the relationship and function of a "type B" peptide, Hsp60sp, in B10PL mice. Qa-1a expressing cells were established by transfecting the human B cell line C1R with recombinant murine Qa-1a cDNA. One of Qa-1a positive transfectants detected by RT-PCR, 3F4, was capable of expressing surface Qa-1a when the cells were passively sensitized with exogenous Qa-1 binding peptides at 26° C. (FIG. 6). 3F4 was thus chosen as a Qa-1 binding peptide-presenting cell to test if Hsp60sp (QMR-PVSRAL) (SEQ ID NO:2) serves as specific target for the Qa-1 dependent CD8+ T cells.

The capacity of the peptides to bind to Qa-1 was first assessed by their ability to stabilize Qa-1 surface expression on 3F4 cells. The 3F4 cells were incubated at 26° C. for approximately 18 hours with Hsp60sp or Qdm peptides and a Qa-1 non-binding peptide HEL 74-96 served as control peptide (12, 14 and 17). As shown by FIG. 6, the binding of exogenous peptide at 26° C. causes a shift in the intensity of Qa-1a surface staining analyzed by FACS. This result showed that not only Qdm, but also other peptides, such as Hsp60sp peptide, could bind to Qa-1.

Since a significant number of murine CD8+ T cells express CD94/NKG2A, it was investigated whether Qa-1/Hsp60sp generated in activated murine T cells is capable of interacting with CD94/NKG2A in a functional NK assay. As shown in FIG. 7, 3F4 cells loaded with control Qa-1 non-binding peptide are susceptible targets for NK killing. In contrast, 3F4 cells loaded with Qdm, but not Hsp60sp, were resistant to the NK killing, consistent with prior reports that Qa-1/Qdm (11), but not Qa-1/Hsp60sp (14), interacts with CD94/NKG2A, leading to the inhibition of NK activity. This is also compatible with the notion that two types of Qa-1/HLA-E binding peptides could be distinguished by their ability of interact with CD94/NKG2A in both humans (14) and mice.

The ability of the Hsp60sp to compete with Qdm for binding to Qa-1 was further tested in a functional NK assay. As shown in FIG. 8 Hsp60sp peptide but not control peptide abrogated the protection of NK killing of 3F4 by Qdm in a dose dependent manner, indicating that Hsp60sp is capable of competing with Qdm for binding to Qa-1. This result is consistent with the observations shown in human studies that human Hsp60sp is capable of competing with the signal peptide of HLA Class Ia leader sequence B7sp for binding to HLA-E (14).

It was next tested if Qa-1/Hsp60sp is the target for the regulatory CD8+ T cells. In this regard, it has previously been demonstrated that the CD8+ T cells selectively down-regulate intermediate avidity T cell clones (1) and the suppression mediated by the CD8+ T cells, in a variety of experimental settings, is Qa-1 restricted (1, 5, 8, 18 and 19). The Qa-1 expressing 3F4 cell was used as the Qa-1 peptide presenting cell to test if Hsp60sp is preferentially recognized by the regulatory CD8+ T cells in a CD8+ T cell inhibition assay. The 1-9NacMBP (myelin basic protein) specific, intermediate avidity clone 1AE10, capable of inducing EAE in vivo (8, 19) served as a positive control, and a non-encephalitogenic, low avidity clone 4D10 as well as 3F4 loaded with control non-Qa-1 binding peptide or Qdm served as negative controls. The 1AE10 clone but not 4D10 was efficiently down-regulated by the CD8+ T cells isolated from EAE recovered mice FIG. 9). These mice are known to be resistant to the re-induction of EAE and have been shown to possess Qa-1 dependent regulatory CD8+ T cells (3 and 8). Interestingly, only 3F4 cells loaded with Hsp60sp, but not Qdm or control peptide, rendered the 3F4 cells susceptible to the down-regulation by the CD8+ T cells. Thus, Hsp60sp is, indeed, a specific target recognized by the CD8+ T cells, when presented by Qa-1.

To directly test whether Hsp60sp is involved in CD8+ T cell mediated regulation in vivo, Hsp60sp was assessed for its potential use as a vaccine to activate the Qa-1 dependent CD8+ T cells to protect animals from EAE. Naïve B10PL mice were injected with bone marrow derived dendritic cells (DCs) loaded with Hsp60sp at least one week before the induction of EAE. The DCs used for vaccination express Qa-1 on their surface but do not express CD8. Vaccination with DCs loaded with Hsp60sp, but not Qdm, significantly protected animals from EAE compared with the control unvaccinated group (Tables 3 and 4).

TABLE 3

Mice vaccinated with dendritic cells loaded with Hsp60sp but not the Qdm are significantly protected from the subsequent induction of EAE.

| | | Severity | | Mean Days | |
|---|---|---|---|---|---|
| Group | Incidence | Mean | Max | Onset | Max Duration |
| Experiment 1 | | | | | |
| Control | 4/4 | 2.0 | 4 | 27 | 23 |
| DC w/Hsp60sp | 0/4 | 0 | 0 | 60 | 0 |
| DC w/Qdm | 2/4 | 1.5 | 3 | 39 | 22 |
| Experiment 2 | | | | | |
| Control | 4/4 | 2.5 | 4 | 24 | 22 |
| DC w/Hsp60sp | 2/5 | 1.2 | 3 | 45 | 5 |
| DC w/Qdm | 4/4 | 3.0 | 4 | 22 | 15 |
| Experiment 3 | | | | | |
| Control | 3/4 | 2.5 | 4 | 28 | 22 |
| DC w/Hsp60sp | 0/4 | 0 | 0 | 60 | 0 |
| DC w/Qdm | 3/4 | 1.5 | 4 | 39 | 12 |
| CD8−/DCw/Hsp60sp | 4/8 | 1.7 | 4 | 34 | 15 |
| Experiment 4 | | | | | |
| Control | 4/4 | 3.5 | 4 | 20 | 16 |
| DC w/Hsp60sp | 2/5 | 1.2 | 2 | 48 | 5 |
| DC w/Qdm | 4/4 | 3.0 | 4 | 26 | 19 |
| CD8−/DCw/Hsp60sp | 6/8 | 2.6 | 5 | 30 | 17 |
| Summary | | | | | |

| | Incidence | Mean Severity | Mean Days Onset | Max Duration |
|---|---|---|---|---|
| Control | 15/16 (94%) | 2.6 +/− 0.63 | 25 +/− 3.6 | 21 +/− 3.2 |
| DC w/Hsp60sp | 4/18 (22%) | 0.6 +/− 0.66 | 53 +/− 7.9 | 3 +/− 2.9 |
| DC w/Qdm | 13/16 (81%) | 2.3 +/− 0.87 | 32 +/− 8.8 | 17 +/− 4.4 |
| CD8−/DC w/Hsp60sp | 10/16 (63%) | 2.1 +/− 0.59 | 32 +/− 2.6 | 16 +/− 1.6 |

TABLE 4

Statistic analysis (Student's t test) of major parameters of EAE induced in the group vaccinated with DCs loaded w/Hsp60sp peptide and EAE induced in different control groups.

| | | | Mean Days | |
|---|---|---|---|---|
| Groups compared | Incidence | Mean Severity | Onset | Max Duration |
| DC w/Hsp versus Control | P < 0.003 | P < 0.001 | P < 0.001 | P < 0.001 |
| DC w/Hsp versus DC w/Qdm | P < 0.01 | P < 0.01 | P < 0.01 | P < 0.002 |

TABLE 4-continued

Statistic analysis (Student's t test) of major parameters
of EAE induced in the group vaccinated with DCs loaded w/Hsp60sp
peptide and EAE induced in different control groups.

| Groups compared | Incidence | Mean Severity | Mean Days Onset | Max Duration |
|---|---|---|---|---|
| DC w/Hsp versus CD8−/DC w/Hsp60sp | P < 0.02 | P < 0.01 | P < 0.002 | P < 0.002 |

Importantly, the protection is CD8+ T cell dependent because depletion of CD8+ T cells in vivo abolished the protection. Thus, Qa-1 dependent CD8+ T cells, which are capable of down-regulating 1-9NacMBP reactive encephalitogenic CD4+ T cells (3 and 8), can be specifically induced in vivo by DCs loaded with Hsp60sp to protect animals from the disease. The precise cellular and molecular mechanisms of DCs' involvement in the induction of the Qa-1 dependent CD8+ T cells are being investigated in separate studies.

It is proposed herein that, in the described "Avidity Model", Qa-1 dependent CD8+ T cells perceive the consequence of the avidity of T cell activation to guide their regulatory functions in vivo (1 and 2). Here a molecular and cellular mechanism is provided, suggesting that selective down-regulation of intermediate avidity T cells by the Qa-1 dependent CD8+ T cells can be accomplished by the specific recognition of Qa-1/Hsp60sp expressed on intermediate avidity T cells by the CD8+ T cells. A significantly higher ratio between the expression of Hsp60 protein and the Qdm-containing MHC Class Ia protein preferentially occurs mainly in the T cell clones activated by intermediate avidity interactions. As a consequence of higher expression of Hsp60 versus MHC Class Ia, Qa-1/Hsp60sp, the specific target for the regulatory CD8+ T cells, is predominantly expressed on the surface of intermediate avidity T cells with or without co-expression of Qa-1/Qdm. The observations disclosed herein provide evidence that preferential expression of particular surrogate target structures, such as Qa-1/Hsp60sp, recognized by the regulatory T cells, on the surface of activated T cells of intermediate avidity, enables the immune system to regulate peripheral immunity by perceiving the avidity of T cell activation. The biological significance of this concept was demonstrated by the ability of Hsp60sp-loaded relevant DCs to induce a CD8+ T cell mediated significant protection from autoimmune encephalopathy in the EAE model.

It is known that in addition to Hsp60sp, three potential Qa-1/HLA-E binding peptides could be generated from Hsp60 protein (14 and 20). It is also known that these three peptides either do not efficiently bind to Qa-1/HLA-E (Hsp60.2 and 3 peptides) (14), or are unable to compete with Qdm for occupancy of Qa-1 (Hsp60.4 peptide) (21). It is thus unlikely that these peptides would interfere with the overall biological outcome of the predominant expression of Qa-1/Hsp60sp on activated intermediate avidity T cells. In this regard, Hsp60sp peptide may represent one example of a type B Qa-1 binding peptide, capable of competing with Qdm or Qdm-like type A peptide/s for occupancy of Qa-1 and serve as specific target structure. The studies presented herein do not exclude the possibility that other Hsp60sp-like peptides may exist which function as targets for the Qa-1 dependent regulatory CD8+ T cells.

To identify other relevant Qa-1/HLA-E binding nonomer sequences the following criteria are observed:
1) the peptide must contain the dominant anchor residues including a Leu at P9, and a Leu or Met at P2. Both of these anchors are known to be critical for Qa-1/HLA-E binding (158, 159); and
2) the peptides must be capable of being generated via proteolysis by the proteasome complex, based on the three major catalytic activities of the eukaryotic proteasome (160).

The steps of an assay system to functionally identify and characterize Qa-1/HLA-E binding peptides that render the activated T cells susceptible to the CD8+ T cell down-regulation are as follows:
1) ability of the peptide to bind to Qa-1/HLA-E—determined by testing Qa-1/HLA-E binding peptides for stabilizing the Qa-1/HLA-E surface expression on Qa-1 transfectants;
2) the peptide is unable to bind to CD94/NKG2A receptor so as to inhibit NK activity in a standard NK assay;
3) ability of type B Qa-1 binding peptides to compete with Qdm or Qdm-like type A peptides, for Qa-1 binding or B7sp for HLA-E binding by peptide competition, for example in a standard NK assay.
4) identification of peptides which render Qa-1+ cells susceptible to the down-regulation by CD8+ T cells in a CD8+ T cell inhibition assay.

The candidate Qa-1/HLA-E type B peptides should fulfill either or both of the above two structural and the four functional requirements.

In the current studies, it was also observed that there were no significant differences among H/M/Qa-1 Protein Indexes obtained when the same clones were activated with varying doses of antigen HEL ranging from 1 μM to 50 μM under standard T cell culture conditions (FIG. 5). This observation indicates that the biological consequence of T cell activation, the differential expression of Qa-1/Hsp60sp versus Qa-1/Qdm, is predominantly depending on the avidity of TCRs on T cells, with a wide range of antigen doses used to activate T cells in an environment providing relatively constant co-stimulation. It is likely that a variation of this consequence of peripheral T cell activation determined by the avidity of TCRs on activated T cells is quite limited, in vivo, within a biological range of antigen presented because somatic hypermutation is rare in TCR post thymic selection in the periphery (22). However, to what extent the extremely high and low doses of antigens as well as the drastic change of intensity and duration of co-stimulation could influence this particular biological outcome of activation of T cells with fixed TCR avidity (affinity and density of TCRs expressed on each T cell) is unknown.

Manipulation of such target structures could be the basis for therapeutic interventions to specifically enhance or block the Qa-1 dependent CD8+ T cell mediated regulation in vivo. In this regard, the application of such interventions in man is based on the evidence that the human homologue of Qa-1, HLA-E, can function as a restricting element for human regulatory CD8+ T cells (23).

Because the Qa-1/HLA-E dependent CD8+ T cell pathway is centrally involved the regulation of immune responses, methods to enhance or suppress this pathway can be employed for treatment or prevention of autoimmune disease, allergy and rejection of transplanted grafts as well as enhancement of effective anti-infectious immunity. Since the Qa-1 or HLA-E binding peptides that are responsible for rendering activated T cells susceptible to the down-regulation by the CD8+ T cells have been identified herein, Qa-1 or HLA-E bearing exosomes loaded with Qa-1 binding peptides of choice can be used to activate this pathway in vivo (161). In this regard, it is noted that dendritic cell-derived exosomes which bear functional MHC class I and class II molecules that can be loaded with synthetic peptides of choice can be used as a peptide-based vaccines (161). Alternatively, a molecular engineered complex composed of Qa-1/self-peptide or HLA-E/self-peptide could also be used as an antigen to specifically activate Qa-1/HLA-E dependent CD8+ T cells. In this regard, it is known that MHC-multimers can be valuable tools for both the stimulation of as well as the analysis of antigen specific T cells in immune response as part of an artificial antigen presenting cells (162-167).

On the other hand, the Qa-1 dependent CD8+ T cell mediated pathway may also play a central role to induce tolerance during tumorigenesis. Thus, in certain tumor patients, blockade of the CD8+ T cell mediated regulatory pathway to rescue the intermediate affinity/avidity anti-tumor T cells may be a necessary anti-tumor therapy, in combination with other approaches. Similarly, blockade of the HLA-E pathway is encompassed herein. In addition, there is a drop of CD4+ T cells after efficient control of AIDS virus in certain AIDS patients. One interpretation is that the Qa-1/HLA-E dependent CD8+ T cell mediated pathway, which is naturally induced to control pathogenic autoimmunity in normal individuals, may play certain roles in these AIDS patients. If this pathway overwhelmingly functions in certain AIDS patients, the regulatory CD8+ T cells may constantly kill newly generated CD4+ T cells regardless of whether these CD4+ T cells are HIV infected. Thus, this would provide a route to therapeutic intervention by specifically blocking the Qa-1/HLA-E dependent CD8+ T cell mediated pathway. Blockade of CD8+ T cell mediated regulatory pathway may be also necessary to prevent a constant drop of CD4+ T cell counts in certain AIDS patients after the efficient control of HIV infection.

In this regard, the specific target structure, such as Qa-1/Hsp60sp, may be differentially expressed on anti-tumor T cells in certain tumor patients or newly generated CD4+ T cells in certain AIDS patients, which is specifically recognized by the TCR on the regulatory CD8+ T cells. Thus, monoclonal antibodies (mAbs), which specifically recognize the target structure expressed on the target T cells, such as the HSP60sp complex, could be used to block this regulatory pathway in vivo.

Making mAbs to Qa-1a/Hsp60sp complex or the HLA-E equivalent can be used as an example of generating this type of mAbs. At a technical level, a stable Qa-1a transfectant J2 has been established which expresses a relatively high level of Qa-1 when passively loaded with Qa-1 binding peptides Qdm or Hsp60sp. It has been shown that in human studies that co-transferring Hsp60sp coding sequence into HLA-E transfectants induces stable surface expression of HLA-E (168). In order to ensure the high level of surface expression of Qa-1 and more efficiently function as an "immunogen" to immunize animals we plan to establish an additional Qa-1 (HLA-E) transfectants, which co-express Qa-1 and Hsp60 signal peptide (J2a). This transfectant can be used to immunize mice in order to generate antisera, which could identify Qa-1 coupled with Hsp60sp expressed on the cell surface. The constructs encoding the recombined Qa-1a/Hsp60sp molecules are generated by replacing the leader nucleotide sequences from +10 to +36 of Qa-1a molecule by either nucleotide sequence encoding HSP-60 sp peptide sequence (5'-catctagaggatgt-tgcttcaaatgcgcccggtcagccgcgctctcagcgcca-3') (SEQ ID NO:3) by PCR method (169). The nucleotide sequences generated are then subcloned into the pRK-5-C-GFP mammalian expression vector after digestion with Xba I and EcoR V. The constructs will be transfected into C1R cell line after confirmed by DNA sequencing. Surface expression of Qa-1a complex will be detected by FACS using Qa-1a specific antiserum as described. Alternatively, J2 cells will be transfected with DNA coding sequence of Hsp60sp in pEGFP-N3 expression vector as described (168).

To generate anti Qa-1a antisera, Balb/C mice will be immunized with J2a (Qa-1/Hsp60sp) cells at 2×106/mouse intravenously. The mice will then be boosted four times by IP injection of 2×106 J2 cells every two weeks. The serum will be tested for staining J2 loaded with Hsp60sp or Qa-1/Hsp60sp expressing J2a transfectants and/or Qa-1a expressing murine T cell clone 1AE10. Anti-Qa-1a sera will be generated by immunizing animals with Qa-1 transfectants co-expressing Hsp60sp. The spleen cells from high title mice will then be used to fuse with fusion partner SP2/0 cells and cloned by limiting dilution in 96 well plates after a successful fusion. The supernatant from each well will be differentially screened by staining J2a and C1R cells with supernatant followed by ELISA assay (170). Briefly, $5 \times 10^4$ J2a transfectants and C1R cells will be plated into flat bottom 96 well plate, rabbit anrti-C1R anti-serum (Pocono Rabbit Farm and Laboratory INC. Canadensis, Pa.) will be added to each well before adding the supernatant to block any antigenic determinants expressed by C1R and J2a cells except Qa-1a/Hsp60sp on J2a transfectants. The plate will be washed and the supernatant will be added into the wells followed by HRP labeled rabbit anti mouse IgG. TMB substrate will be added into each well for 10-15 minutes incubation, the reaction will be stopped by adding 2N $H_2SO_4$. The absorption will be determined using a 96-well plate reader (Molecular Devices, Menlo Park, Calif.). The positive control for staining will be anti-Qa-1a sera. The wells in which the supernatants are only positive for J2a but not for C1R will be chosen for further sub-cloning. The general methods for producing these mAbs were previously successfully employed by our lab in the identification of the mAbs to CD40L and VLA-1 (171, 172).

Materials and Methods

Real Time PCR

RNA was isolated using the RNEasy system (Promega). Reverse transcription and real-time PCR were performed using the AMV reverse transcriptase (Promega) and Light-Cycler Faststar™ DNA Master SYBR Green I Systems on a Roche Light Cycler (Roche, Indianapolis, Ind.). The cycling parameters are: 95° C., 10 min denaturation; 95° C., 10 sec at 55-61° C. (55° C. for H-2$D^d$, 59° C. for Qa-1b, 61° C. for Hsp60), 8 sec at 72° C., 13 sec to 20 sec (13 sec for Hsp 60 and Qa-1b, 20 sec for H-2$D^d$)×40 cycles. PCR primers: Qa-1b forward, CCCAGAGTAGCCCACACTCGCTGCGGT (SEQ ID NO:5); reverse, CCCGAGGCTCCATCCTCG-GATTT (SEQ ID NO:6); mHsp60 forward, GGGATG-GCACCACCACTGCCACTGTT (SEQ ID NO:7); reverse, TCCATGGTGCTAGCCATATGC (SEQ ID NO:8); H-2$D^d$ forward, GGGCGATGGCTCCGCGCACGCTGCTCCT-GCTCCTGCT (SEQ ID NO:9); reverse, CCGTGTTGTC-CACGTAGCCGACTTCCATGT (SEQ ID NO:10).

SDS-PAGE and Western Blot Analysis

SDS-PAGE and Western blotting were conducted following standard procedures. Abs used: anti-actin, anti-Hsp60, anti-MHC Class Ia (H-2$D^d$) and anti-Qa-1b, and the secondary Ab rabbit anti-mouse HRP or rabbit anti-Rat HRP. Target proteins were detected using the ECL detection kit (Amersham Biosciences). All blots were densitometrically quantitated using ChemiDoc XRS Imager Quantity one-4.5.0 software (Bio-rad).

Qa-1a Transfectants and T Cell Clones

The cDNA encoding full-length Qa-1a was isolated from the T cells of B10PL mice by reverse-transcription polymerase chain reaction (RT-PCR) using the following primers: forward, CATGGTGAGGATGTTGCTTTTTGC-CCACTTGCTCCAGCTGCTGGTCAGCG (SEQ ID NO:10); and reverse, A GAACATGAGCATAGCATCCTTT (SEQ ID NO:11). The Qa-1a cDNA was subcloned into the mammalian expression vector pcDNA3.1 (Invitrogen) and transfected by electroporation (Gene-Pulser™, Biorad) into the human B cell line C1R, following which stably transfected clones were isolated by limiting dilution under G418 selection (Invitrogen Life Technologies).

Qa-1 Binding Assay

Selected Qa-1a-PcDNA3.1 positive transfectants detected by RT-PCR were assayed for their Qa-1 surface expression after loading with known Qa-1 binding peptides. In brief, Qa-1a transfectants were incubated at 26° C. for approximately 18 hours with Hsp60sp or Qdm peptides (10, 12 and 17). The surface expression of Qa-1a was assessed by staining with anti-Qa-1a sera followed by Phycoerythorine (PE)-goat anti-mouse Ig, analyzed on a FACScan flow cytometer and CellQuest™ software (Becton Dickinson, Mountain View, Calif.)(1). All peptides were used at 50 µM unless specifically indicated.

NK Assay

NK cell lines are routinely established from B10PL mice (24). Unlabeled 3F4 cells were loaded with test peptides at 26° C. overnight and mixed with an equal number of CFSE labeled human EBV transformed LCL cells which are not susceptible to the killing by mouse NK cells. Graded numbers of mouse NK cells were added to the mixture of 3F4 and LCL cells and further incubated at 37° C. for 2 hrs. 3F4 cells, which were not loaded with peptides or loaded with non-Qa-1 binding peptides served as controls. The cell mixtures were then stained with anti mouse H-2$^U$ mAb 3-8-3P-PE to distinguish NK cells from target cells. The change in the ratio of 3F4 to LCL cells in the presence or absence of NK cells in each group detected by FACS (1) reflects the specific NK killing: % specific killing={[the killing ratio in control wells (without NK)–the killing ratio in experimental wells (with NK)]/the killing ratio of control wells}×100%.

Peptide Competition Assay

Peptide unloaded 3F4 cells showed high susceptibility to NK killing (E/T ratio 2:1), and served as a positive control in the peptide competition assay. 3F4 cells loaded with Qdm (20 µM), which were resistant to the NK killing, served as targets for competition. Competing peptides (Hsp60sp or control non-Qa-1 binding peptide) at 50, 100, 200 µM were added to the 3F4 cells, together with 20 µM Qdm for 18 hrs at 26° C. (14). Equal numbers of CFSE labeled LCL cells were mixed with 3F4 cells and NK cells were then added into the mixture of peptide loaded 3F4 cells and LCL cells. The percent NK killing of 3F4 cells was evaluated. In the presence of the peptides that are capable of effectively competing with Qdm for occupancy for Qa-1, but do not interact with CD94/NKG2A, the abrogation of inhibition of 3F4 target cell lysis by NK cells in the presence of Qdm serves as a functional parameter of effective competition.

CD8+ T Cell Inhibition Assay

CD8+ T cells were purified with CD8 MACS magnetic beads (Miltenyibiotec, Inc. Auburn Calif.) (1). 3F4 cells were passively loaded with peptides overnight at 26° C. Equal number of unlabeled 3F4 cells loaded with peptides and CFSE labeled 3F4 cells that are not loaded with peptide were mixed and a graded number of CD8+ T cells were added to the targets. CD8+ T cells from naïve mice serve as control and it was established that these CD8+ T cells have no effect on the activated target T cells. 4 days later, the cell mixtures were stained with anti-mouse CD8-PE mAb to distinguish CD8+ T cells from target cells. The ratio between peptide-loaded (non-CFSE-labeled) 3F4 cells and non-loaded (CFSE labeled) 3F4 cells in the presence of CD8+ T cells was determined as % of specific inhibition: {[the ratio of loaded to unloaded 3F4 cells in control cultures (without CD8+ T cells)–the ratio in experimental cultures (with CD8+ T cells)]/the ratio in control cultures}×100% (1).

Vaccination of Animals with Dendritic Cells (DCs) Loaded with Qa-1 Binding Peptides in EAE Model Bone marrow-derived DCs were generated from B10PL mice as described (25). On Day 6, assessed by cell surface staining, these DCs routinely express Qa-1 on their surface but are CD8 negative. Day 6 DCs were loaded with either Hsp60sp or Qdm at 50 µM for 2 hours at 37° C. Cells were then washed once with 50 mls of PBS and injected into naïve B10PL mice intravenously at 1×10$^6$ cells/mouse at least one week before EAE induction.

Discussion

Avidity Model of Self/Non-Self Discrimination

The results suggested herein support an "avidity model" of self/non-self discrimination which is achieved by both central thymic selection and peripheral immune regulation. The conceptual framework that links these two events is the understanding that both in the thymus and in the periphery the survival or the fate of T cells is determined by the avidity of the interactions between TCRs on T cells, specific to any antigens and MHC/antigen peptides presented by APCs.

It is envisioned that the immune system achieves the goal of self/non-self discrimination, during adaptive immunity, not by recognizing the structural differences between self versus foreign antigens, but by sensing the avidity of T cell activation. Intrathymic deletion of high avidity self-reactive T cell clones generates a truncated peripheral self-reactive repertoire composed of only intermediate and low but devoid of high avidity clones compared with the foreign-reactive repertoire which also contains high avidity clones.

The existence of intermediate avidity self-reactive T cells in the periphery represents a potential danger of pathogenic auto-immunity inherited in each individual because potentially pathogenic self-reactive T cells are included in the pool of intermediate avidity T cells and can often be functionally activated, by "danger signals", to elicit autoimmune diseases. The distinctive compositions of peripheral T cell repertoires to self versus to foreign antigens provides a unique opportunity for the immune system to discriminate self from non-self, in the periphery, by selectively down-regulating intermediate avidity T cells to both self and foreign antigens. Selective down-regulation of the intermediate avidity T cell populations containing the potentially pathogenic self-reactive T cells provides a mechanism to specifically control autoimmune diseases without damaging the effective anti-infection immunity, which is, largely, mediated by high avidity T cells specific to the infectious pathogens. In this regard, it was recently shown that regulatory Qa-1 dependent CD8+ T cells selectively down-regulate intermediate avidity T cells, to both self and foreign antigens, and as a consequence, specifically dampen autoimmunity yet optimize the immune response to foreign antigens. This is accomplished via specific recognition, by the TCRs on Qa-1 dependent CD8+ T cells, of particular Qa-1/self-peptide complexes which function as surrogate markers expressed on activated intermediate avidity T cells, to any antigens, that are hence specifically targeted for down-regulation.

This regulatory pathway thus represents one example of a peripheral mechanism that the immune system evolved to complete self non-self discrimination that is achieved, imperfectly, by thymic negative selection, in order to maintain self-tolerance.

The "Avidity Model" described here incorporates the concepts of thymic negative selection, the "Tunable Activation Thresholds Hypothesis" and the "Danger Model" to understand how the immune system achieves self non-self discrimination during adaptive immunity. It provides a unified and simple paradigm to explain various seemingly unrelated biomedical problems inherent in immunological disorders that can not be uniformly interpreted by any currently existing paradigms.

The Implications of the Conceptual Framework of the Avidity Model on Our Understanding of Peripheral T Cell Regulation 1. The "Avidity Model" proposes that the specificity of the regulation is not at the level of antigens that activate the target T cells. The specificity is at the level of recognizing or sensing a common consequence of T cell activation regardless of which antigens the target T cells are triggered by. It thus differs from the "Idiotypic Model" (103), which functions to distinguish immune response to each individual antigen, via recognition of countless idiotypic peptide/s derived from the V regions of either T cell receptors or Immunoglobulins generated by activated T or B cells (104-106). In contrast, the "Avidity Model" functions to discriminate immune responses by recognizing and distinguishing the only two types of the consequences of the immune responses determined by the avidity interactions between TCRs on T cells, specific to any antigens, and MHC/antigen peptides presented by APCs (42, 43). Conceptually, the "Avidity Model" contains some elements of "ergotypic regulation" in that both types of regulation recognize the consequence of T cell activation. But it also differs from "ergotypic regulation" because the "ergotypic regulation" does not consider the avidity of the interactions that activate the T cells (107-108). The "Avidity Model" thus represents a general alternative approach that enables the immune system to control peripheral immunity with sufficient specificity but does not demand a huge repertoire for the regulatory T cells. For example, in the Qa-1 dependent CD8+ T cell pathway, the actual target structure that is recognized by the CD8+ T cells is likely to be certain self-peptides, presented by Qa-1, differentially expressed on target T cells as a function of avidity interactions of T cell activation. Since the diversity of self-peptides binding to Qa-1 that are responsible for rendering T cells susceptible to the down-regulation by CD8+ T cells is limited, the model enables the immune system to regulate immune responses to almost infinite diverse self and foreign antigens in a effectively specific but simple way.

2. The model predicts that the immune system employs a unified mechanism of suppression to regulate peripheral immune responses to both self and foreign antigens, which appears to have opposing effects: preserving tolerance to "self" while facilitating T cell affinity maturation to "foreign". Because the compositions of the naïve peripheral TCR repertoires to self and foreign antigens are different due to thymic negative selection, the biological consequences of selective down-regulation of the intermediate avidity T cells to self and foreign antigens are also different (42, 43) (see FIG. 10). This forms the conceptual framework for a new paradigm to explain, at a biological system level, how the immune system achieves the goal of self non-self discrimination, during the adaptive immunity, without the necessity to distinguish self from non-self in the periphery at the level of T cell regulation.

3. The conceptual framework of the "Avidity Model" may also well be suited for other peripheral regulatory pathways, for example, the "specialized CD4+ Tregs". These CD4+ Tregs may control the peripheral pathogenic auto-immunity by either non-specifically regulating the magnitude and class of autoimmune response (26, 27) or by discriminating self from non-self. It is conceivable that, at least certain subset of the CD4+ Tregs, may, like the Qa-1 dependent CD8+ T cells, be involved in self non-self discrimination by down-regulating activated T cells of intermediate avidity but employing different recognition and effector mechanisms.

Self/Non-Self Discrimination Achieved During Thymic Negative Selection Determines how the Adaptive Immunity is Regulated in the Periphery to Maintain Self-Tolerance a. The Immune System can Discriminate Self from Non-Self by Sensing the Consequences of Different Avidity of T Cell Activation, but not by Recognizing the Structural Differences Between Self Versus Foreign.

Unlike the mechanisms employed by the immune system to discriminate self from non-self during innate immunity (28-30), the immune system appears to utilize a completely different approach to achieve self non-self discrimination during adaptive immunity in both the thymus and the periphery. The basic question is: "Does the immune system discriminate self from non-self by distinguishing what is self from what is foreign?" It is envisaged that the immune system does not "know" the differences between the distinctive structures of a self-antigen versus a foreign antigen during thymic negative selection because foreign antigens presented during fetal life are thereafter considered self (44, 45).

Furthermore, the immune system does not "know" the differences between the T cell immune response to a self versus to a foreign antigen at the level of peripheral T cell regulation either. For example, Qa-1 dependent CD8+ T cells regulate the peripheral immune responses by selectively down-regulating activated T cells of intermediate avidity to both self and foreign antigens, regardless of which antigen the target T cells are triggered by (43).

It appears that one major mechanism that the immune system uses to achieve self/non-self discrimination is to perceive, at different stages of development, differentially, the avidity of the interactions of T cells responding to any antigens, both in the thymus and in the periphery. In the thymus, the immune system negatively selects for intermediate and low avidity T cells by eliminating high avidity T cells (33-35), whereas in the periphery, it negatively selects for high and low avidity T cells by eliminating intermediate avidity T cells (42,43). The preservation of low avidity self-reactive T cells, by allowing these cells to survive both the thymic and peripheral negative selection, is biologically significant. It is not only because low avidity to self MHC is an essential requirement for MHC restriction in T cell response achieved by thymic positive selection, but also relies on the fact that these low avidity self-reactive T cells would have high or intermediate avidity to foreign antigens (47,109,110) due to the sufficient plasticity of their TCRs (111). These low avidity self-reactive T cells are thus preserved as a naive pool for the foreign repertoire in the periphery (43).

b. Why and how do Intermediate Avidity Self-Reactive T Cells Escape Thymic Negative Selection?

The activation state of thymocytes in the thymus is crucial for thymic selection, which is determined by two major parameters: the avidity of the TCRs and the level of self-antigens presented (36, 37, 112). The avidity of a thymocyte is determined by the affinity of its TCRs, dictated by the structures generated by VDJ rearrangement, and the density of the TCRs expressed. The level of self-antigens presented in the thymus is determined by the number and the affinity of the MHC/self-peptide complex expressed on the surface of APCs (113), which could be influenced by the concentrations of extracellular antigens in the circulation, the expression of intracellular antigens in the thymic APCs as well as the capacities of the APCs to process and present self-antigens. In general, high level presentation of antigens tends to activate thymocytes with a wide spectrum of avidity covering all high and the majority of intermediate range. In contrast, low level presentation of antigens tends to only activate thymocytes of high avidity. The intermediate level presentation of antigens might activate thymocytes with high and certain extent of intermediate avidity (37, 114-116) (see FIG. 11).

Each individual thymocyte must be negatively selected in the thymus to enable the immune system to respond to virtually any foreign antigens but avoid harmful responses to self in the periphery. The education process of the thymocytes could, in principle, be accomplished either by recognizing one or a set of "common" peptides, which could represent all peripheral self-antigens in the thymus (118,119), or by "seeing" the actual peripheral, tissue-restricted or age-dependent, self-peptides expressed in the thymus, or by both. Discovery of the autoimmune regulator (Aire) gene (120,121) provided the first direct evidence for the latter hypothesis. Thus, Aire, functions as a transcription factor which promotes the ectopic expression of peripheral tissue-restricted antigens, from a particular set of organs, in medullary epithelial cells in the thymus (122,123) and also enhances the antigen-presentation capacity of these cells (124). It is unclear if "Aire" is an isolated unique event or it represents an example of a class of genes controlling the expression and presentation of all presentable peripheral self-antigens in the thymus. Nevertheless, the discovery of the Aire gene makes it possible to predict that thymic APCs, under the control of Aire or other not yet identified Aire like genes, express and present a full array of peripheral tissue-restricted or age-dependent self-antigens that the thymocytes would, otherwise, have no access to, during thymic negative selection.

Independent of how peripheral self-antigens are "seen" by the thymocytes, thymic negative selection has evolved to delete all self-reactive T cells that could potentially be functionally activated in the periphery in order to eliminate any "imminent danger" of pathogenic autoimmunity. This could be achieved either by a higher level presentation of self-antigens in the thymus than in the periphery (125) or by a lower or less "stringent" threshold of activation state of thymocytes for apoptosis in the thymus than for active function of these cells in the periphery (35). Thus, self-reactive T cells that could be functionally activated by endogenous self-antigens in the periphery would be guaranteed to be activated in the thymus in order to undergo apoptosis and be deleted. Self-reactive T cells that could not be sufficiently activated in the thymus due to insufficient presentation of self-antigens and escape thymic negative selection would not be, for the same reason, functionally activated in the periphery by endogenous self-antigens. In addition, "Tunable Activation Thresholds Mechanism" enables the thymic escapees to "ignore" the endogenous self-ligands that are repetitively and constantly presented to them in the periphery (36,37). So that under biologically normal circumstances there would be no pathogenic auto-immunity in the periphery unless the system is perturbed by, for example, "danger signals" (38,39) generated during active infections or injuries.

On the other hand, thymic negative selection has also evolved to provide a peripheral T cell repertoire with sufficiently large size and maximum flexibility in order to respond efficiently to foreign antigens. A threshold for the activation of thymocytes, therefore, must be established during thymic negative selection to determine the degree of activation, which would allow apoptotic cell death to occur. The immune system uses self-antigen as a standard to establish this threshold. In general, thymocytes of high avidity specific to self-antigens presented at any level must be deleted and thymocytes of low avidity specific to self-antigens presented at any level, which could be activated at a baseline or very low level, must be preserved. The flexible area would be the self-reactive thymocytes of intermediate avidity. Thus, thymocytes of intermediate avidity specific to self-antigens presented at high levels would be deleted whereas thymocytes of intermediate avidity specific to self-antigens presented at low levels would be preserved. In FIG. 11 a line, which is drawn between the intersection of high end of low TCR avidity and the highest biological level of antigen presented and the intersection of the low end of high TCR avidity and the lowest level of antigen presented, represents a hypothetical threshold of the activation state. Thymocytes of activation state beyond the threshold undergo apoptosis and thymocytes of activation state below the threshold are spared from apoptosis. Thus, thymocytes, which escape thymic negative selection, are all the thymocytes of low avidity and at least half of the thymocytes of intermediate avidity which are specific to the self-antigens that are presented at low to certain extent of intermediate to high levels.

At this point, a third parameter that must be considered is the effect of co-stimulatory molecules (126, 127) as well as cytokines, chemokines, integrins and their respective receptors involved in T cell activation. There is currently little information available to assess the functional relationship of these molecules in the thymus versus in the periphery. In this regard, our basic thinking follows the same theme. In principle, molecular interactions involved in activation, such as CD28/B7 and CD40/CD40L, are likely higher or at least comparable in the thymus than in the periphery where as molecular interactions involved in inactivation, such as CTLA-4/B7, might be lower or the same in the thymus than in the periphery. The rationale for defining these molecules as a separate parameter that influences the activation state of thymocytes is based on the consideration that manipulation of these signals is more feasible than manipulation of TCR avidity and the level of antigen presented during an immune response in the periphery. The former is known to be relatively "fixed" by TCR VDJ rearrangement (128-131) and the latter is usually the primary cause of the immunological disease. This third parameter could thus provide a potential window to practically enhance or block the peripheral immune responses of certain kind for therapeutic purpose, but the price to pay would be non-specific affects of such therapy on normal on going immune responses.

Taken together, the view that self non-self discrimination is a continuous process involving both thymic negative selection and peripheral immune regulation requires an understanding of how these two general events are connected. The "Avidity Model" provides a unified conceptual framework to understand the biological necessity of the connection between the thymic negative selection and the peripheral immune regulation. The physical link between these two events is the fact that release of intermediate avidity self-reactive T cells into the periphery, which contain potentially pathogenic self-reactive T cells (40,41), is a biological consequence of thymic negative selection and must be specifically dealt with by peripheral regulatory mechanisms.

c. Can the Intermediate Avidity Self-Reactive T Cells that are Released from Thymic Negative Selection and Activated in the Periphery Gain Elevated Avidity to Escape the Peripheral Down-Regulation?

The distinctive compositions of peripheral T cell repertoires to self versus to foreign antigens provides a unique opportunity for the immune system to discriminate self from non-self, in the periphery, by selectively down-regulating intermediate avidity T cells to both self and foreign antigens. Selective down-regulation of the intermediate avidity T cell populations containing the potentially pathogenic self-reactive T cells is a mechanism that the immune system evolved to specifically control autoimmune diseases without damaging the effective anti-infection immunity, which is, largely, mediated by high avidity T cells specific to the infectious pathogens. Qa-1 dependent CD8+ T cell pathway represents one of such mechanisms. This type of mechanisms must deal with the question of whether it is powerful enough to control the pathogenic auto-immunity that is induced by the intermediate avidity T cells which might gain an elevated avidity following peripheral activation to enable them to escape the peripheral down-regulation. In this regard, the Qa-1 dependent CD8+ T cell pathway has been shown to be inherently built with sufficient flexibility to particularly deal with the possibility that intermediate avidity T cells may gain certain elevated avidity when activated in the periphery.

Figure 12:
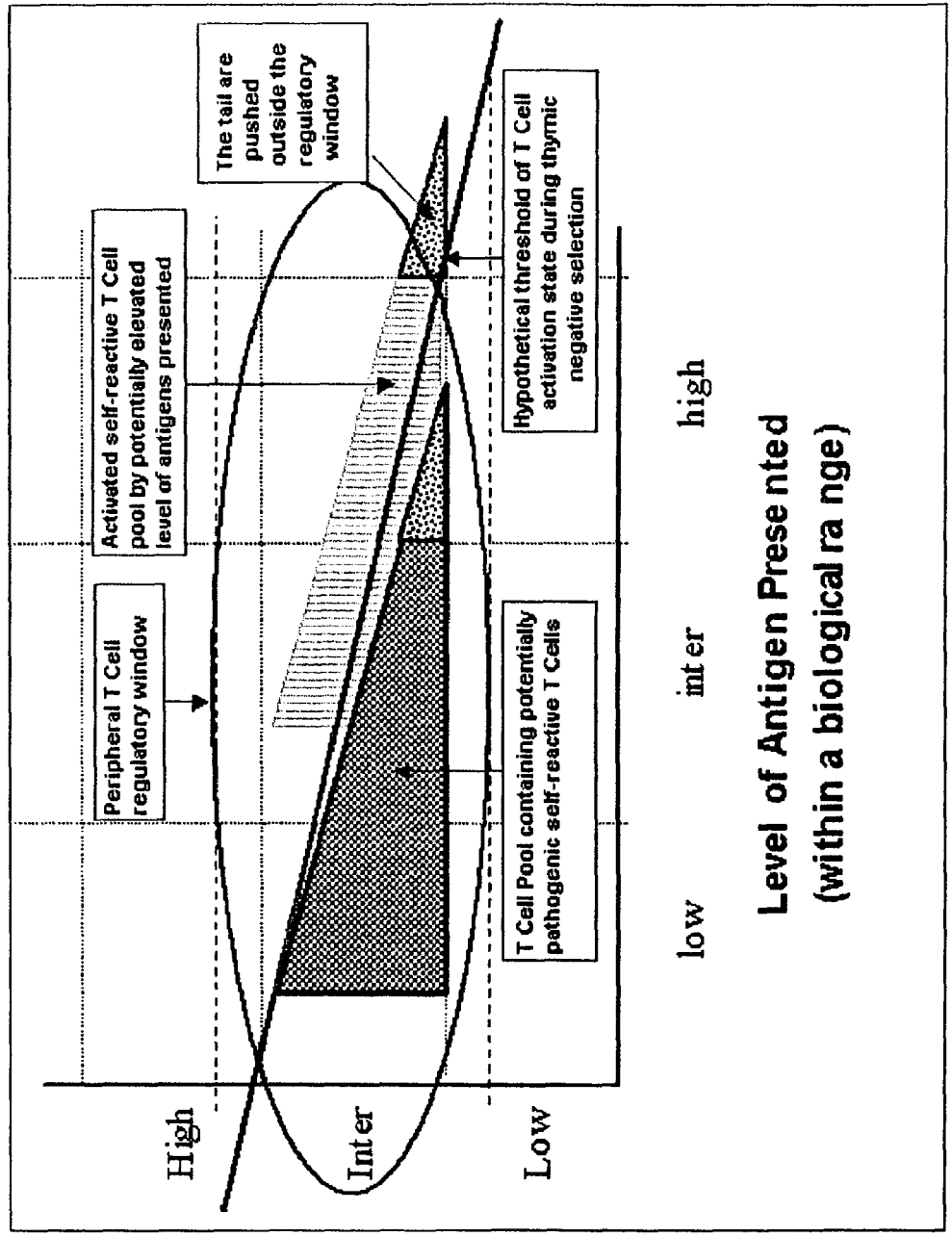

First, it has been shown that Qa-1 dependent CD8+ T cells down-regulate the intermediate avidity T cells activated by a wide range of antigen dose (43). It is thus proposed that the window of the regulation is likely to cover the intermediate avidity T cells activated over a spectrum of physiologically relevant levels of antigen presentation, especially when level of antigen presented moves from low to intermediate or from intermediate to middle high (FIG. 12). In this regard, an important controlling factor is the absence of frequent somatic hypermutation in TCRs post thymic selection which effectively confines the extent of the elevation of the avidity of self-reactive T cells when these cells would be activated in the periphery (128-130). The variables would be the concentrations of the self-antigens and the capacity of the APCs to present the self-antigens, which is mainly influenced by the functional stage of the co-stimulatory molecules involved. There may be a small tail area, occupied by the T cells that are originally with relatively very low avidity and could only be functionally activated by high levels of antigens presented, pushed outside the regulatory window. Since the T cells fallen into this tail area can only be functionally activated by high level presentation of antigens, close to the highest biological limit, the room for the antigen presentation level moving towards higher range is small. Thus, the situations that could push the tail area outside the window of regulation would likely only occur under certain exceptional circumstances and rare, for example, the extremely potent co-stimulation induced during immunological therapy (see below). In principle, the acquired elevated avidity of the intermediate avidity T cells, during the infections or injuries, would unlikely push these T cells outside the window of peripheral regulation.

Second, an overlapping zone of avidity between the low boundary of the activation state of thymocytes for apoptosis in the thymus and the high boundary of the activation state of T cells for peripheral down-regulation exists in the periphery and functions to safe guard self-tolerance. In analyzing the HEL-reactive repertoire in HEL TG and WT mice it has been observed that HEL reactive clones bearing a common canonical TCR Vβ motif GTGQ are susceptible to the down-regulated by the CD8+ T cells in the periphery (43). Interestingly, although GTGQ motif frequently appears in the HEL-reactive repertoire in WT mice where HEL functions as a foreign antigen (43), this motif has never been found in HEL-reactive repertoire in HEL TG mice where HEL functions as a self-antigen (unpublished observation). This observation suggests that clones bearing GTGQ motif are self-reactive and are deleted during thymic negative selection. Since the avidity of an actual T cell clone bearing GTGQ motif measured by $ED_{50}$ is 3 μM (43), the low boundary of avidity for activation state of HEL reactive thymocytes to be intrathymically deleted is likely at least 3 μM or lower. On the other hand, it has been demonstrated that the high boundary of avidity for peripheral down-regulation of HEL reactive clones by the Qa-1 dependent CD8+ T cells is higher than 1 μM (43). Thus, these observations indicate the possibility that the low boundary of avidity for thymocytes to undergo apoptosis during thymic negative selection could be much lower than the high boundary of avidity of T cell activation state for peripheral T cell regulation. This creates an overlapping zone in the periphery between the low boundary of the activation state of thymocytes for apoptosis in thymus, which allows intermediate avidity T ells to escape into the periphery, and the high boundary of the T cell activation state for down-regulation (FIG. 13). The existence of such an overlapping zone is important to understand the functional relationship between thymic selection and peripheral regulation. For example, if the intermediate avidity self-reactive T cells, which escaped thymic negative selection, were functionally activated in the periphery, even though these clones may gain certain elevated avidity, they would hardly pass the overlapping zone to escape peripheral down-regulation. The overlapping zone thus provides a second level safe guard, superimposed on the sufficient flexibility of the regulatory window described above, to maintain the peripheral self-tolerance. There may be some exceptions that the self-reactive T cells are not only pushed outside the regulatory window but also exceed the high boundary of overlapping zone due to extremely potent co-stimulation that enables these clones to escape the peripheral down-regulation. Such cases would likely occur during immunological therapies to manipulate the co-stimulatory pathways, such as anti-CTLA-4 treatment in tumor vaccine therapy and provides an possible interpretation of the inverse relationship between the control of tumor and the increased tendency of organ specific pathogenic auto-immunity (132-134). In general, the T cell clones fallen into the overlapping regulatory zone would be mainly foreign reactive and much fewer are self-reactive clones with avidity that are originally close to the low boundary during thymic negative selection but have gained an elevated avidity when accidentally activated in the periphery.

d. Self/Non-Self Discrimination and Autoimmune Disease

Based on the conceptual framework of the "Avidity Model", defects of self/non-self discrimination at either central or peripheral levels would cause pathogenic autoimmunity in the periphery with distinctive characteristic features.

Autoimmune Disease Develop as the Consequence of Failure of Central Thymic Selection Defects in genes primarily involved in thymic negative selection or some genes controlling general homeostasis in the thymus would lead to the release of high avidity self-reactive T cells, specific to a wide array of self-antigens expressed in multiple organs, from thymus. These high avidity self-reactive T cells are capable of being functionally activated by endogenous self-antigens presented at any levels, which are biologically available in the periphery. Different degrees of rather immediate and global autoimmunity develop as a direct consequence of the activation of high avidity self-reactive T cells in the periphery, such as symptoms seen in Autoimmune polyglandular syndrome type 1 (APECED) (95) or in Aire deficient mice (121, 135). In general, pathogenic auto-immunity due to failure of thymic negative selection, which are usually rare genetic defects, develops spontaneously and early in life and reveals a rather global and diffuse auto-immunity affecting multiple organs.

One consequence of failure of thymic negative selection, due to the release of high avidity self-reactive T cells, is the formation of a self-reactive T cell repertoire with the composition that is indistinguishable from the foreign-reactive repertoire. It is unlikely that peripheral regulatory mechanisms would evolve to specifically deal with this type of rare genetic defect, which requires mechanisms that permit discrimination between high avidity T cells specific to self versus to foreign antigens and no working hypothesis has ever been proposed to deal with this problem. Nevertheless, the intrinsic mechanisms that control the magnitude and class of immune response, such as Th1 versus Th2 or Tr1 and Tr3 cells, may play major roles in non-specific amelioration of overwhelming global pathogenic auto-immunity caused by genetic defect of thymic negative selection (27).

"Danger Signals" and Peripheral Regulation Play Central Roles in the Development and Control of Organ Specific Autoimmune Disease On the other hand, as a consequence of thymic negative selection, peripheral T cell repertoire is composed of intermediate and low avidity self-reactive T cells. As discussed above, self-reactive T cells of low avidity are "innocent" and constitute the major portion of the naïve peripheral T cell repertoire to foreign antigens. The fact that self-reactive T cells of intermediate avidity are part of the naturally formed peripheral T cell repertoire is biologically significant because it represents a potential danger of pathogenic auto-immunity inherited in each individual. In general, self-reactive T cells of intermediate avidity, which can not be sufficiently activated in the thymus to be deleted, due to insufficient presentation of self-antigens, would not be functionally activated in the periphery either (36, 37), unless they encounter "self-peptides" presented at a sufficiently higher level by the professional APCs. The sufficient presentation of "self-peptides" could occur in the periphery either during certain infections, due to molecular mimicry between infectious agents and self-antigens (136, 137) or when large amount of self-antigens, a type of the "danger signals", is released from the injured cells at the inflammation sites, as a consequence of unrelated infections or injuries (38, 39). In addition, increased expression of co-stimulatory or MHC molecules on professional APCs as a consequence of the release of certain cytokines, such as γ-INF, from the inflammation sites may also play a crucial role in the accidental activation of intermediate avidity self-reactive T cells. Because infections or injuries are usually confined within the organ affected, an active auto-immunity evoked by such insults, from a biologically normal peripheral T cell repertoire, is likely organ specific.

Since the potentially pathogenic self-reactive T cells are included in the pool of intermediate avidity self-reactive T cells (40, 41), the potential for pathogenic autoimmunity during infections or injuries is great. Selective down-regulation of intermediate avidity T cells is one mechanism that the immune system evolves to specifically deal with this biologically inherited problem without paying the price to damage normal anti-infection immunity (33). Thus in the absence of a proper peripheral regulation, "danger signals", generated from the "dangerous self", during infections or injuries (38, 39) play a central role for an organ specific pathogenic auto-immunity.

In summary, the "Avidity Model" provides a unified conceptual framework of the cellular and molecular basis to understand the development and control of pathogenic auto-immunity. Since the immune system evolved to be engaged in such a way that biologically available self-antigens would not be presented at a sufficient level in the periphery to functionally activate any self-reactive T cells, which escape thymic negative selection, peripheral self-tolerance is, indeed, established by thymic negative selection and reinforced by the "Tunable Activation Thresholds Mechanism". (36,37). However, the peripheral regulatory mechanisms have also evolved to maintain peripheral self-tolerance by selectively down-regulating intermediate avidity self-reactive T cells, which are released from thymus as a biological consequence of thymic negative selection and could often be functionally activated during environmental insults, such as infections or injuries. In this regard, the conceptual framework of the "Danger Model" (38, 39) provides a solution to answer the central question of how the escaped intermediate avidity self-reactive T cells could be functionally activated in the periphery to elicit autoimmune disease. It is thus proposed that the peripheral regulatory mechanisms of selective down-regulation of intermediate avidity T cells play a central role in control of organ specific autoimmune disease, including multiple sclerosis, type 1 diabetes and rheumatoid arthritis, which are usually triggered by the "danger signals" generated during infections or injuries (38, 39).

The "Avidity Model of Self/Non-Self Discrimination" and Immunological Relevant Clinical Problems The "Avidity Model" represents an example of a "System Biological Hypothesis" applied to the immune system, which could provide a unified and simple conceptual framework to understand the process of self/non-self discrimination and also the theoretical basis, which allows the translation of this concept for novel clinical applications. Using the regulatory pathway mediated by Qa-1 dependent CD8+ T cells as an example the potential impact of the "Avidity Model" on immunological relevant clinical problems is set forth below. In this regard, the future application of this pathway in man is based on the evidence that the human homologue of Qa-1, HLA-E, can function as a restricting element for human regulatory CD8+ T cells (138, 139).

a. Autoimmune Disease

As discussed above, organ specific autoimmune diseases that are commonly seen are likely the consequence of deregulation of the peripheral auto-immunity. These diseases could be treated by activating peripheral regulatory mechanisms, such as the Qa-1/HLA-E dependent CD8+ T cell mediated pathway, to selectively suppress the intermediate avidity T cell populations. Because the specificity of the regulation is not at the level of the antigens which activate the target T cells, this approach offers a theoretical basis for treating and preventing autoimmune disease without relying on the knowledge of the particular self-antigens involved, in any given autoimmune disease, which are largely undetermined at the present time. Since infections could play a central role in organ specific autoimmune disease in the absence of peripheral regulation, control of infections in these patients should be the primary treatment, when immunological therapy is considered.

b. Infections Versus Autoimmune Disease and Allergy

The clinical impact of this regulatory pathway relies on the fact that the pathway can be induced by T cells of intermediate avidity, activated by any antigens, to control pathogenic auto-immunity, as its primary task, yet it strengthens or at least, does not damage the anti-infection immunity. The "Avidity Model" thus provides a unique window to envision the relationship between auto-immunity and anti-infection immunity which could offer a simple answer, in addition to different hypothesis, for a well-established phenomenon of "hygiene hypothesis" (140). In highly developed industrialized countries increased autoimmune disease and allergy are often associated with decreased infectious disease as a result of antibiotics, vaccinations, or more simply, improved hygiene and better socioeconomic conditions (140). Based on the "Avidity Model", certain natural infections during early childhood could activate the intermediate, in addition to high, avidity T cells, to induce the regulatory pathways, which would in turn suppress intermediate avidity T cells, activated by any self-antigens, to ensure peripheral self-tolerance in adult life. In the context of allergy mediated by Th2 cells, the in vitro studies have demonstrated that varying the strength of TCR signaling (avidity interaction) can strongly influence T helper cell polarization in a naïve T cell population (141-143). Following stimulation with lower avidity TCR ligands, the Tec kinase, Itk, is activated which promotes Th2 differentiation by negatively regulating T-bet mRNA expression which is known to be essential for Th1 differentiation (144). Connection of the association of lower avidity responses with Th2 phenotypes and higher avidity responses with Th1 phenotypes to the observations that the occurrence of an allergic response is often associated with the preferential mucosal antigen entry has led to a hypothesis for allergy based on the "Avidity Model". Although allergens are foreign antigens the immune responses to allergens might be dominated by Th2 cells that are activated by intermediate avidity interactions between TCRs on allergic T cells and MHC/allergen-peptide complexes presented by the local APCs in the mucosal environments. Thus, allergy could be normally controlled by peripheral regulatory mechanisms of selective down-regulation of intermediate avidity T cells, which also play major roles in control of pathogenic auto-immunity.

The inverse relationship of infections versus auto-immunity and allergy is further highlighted by the consistent observations that autoimmune disease in susceptible strains of animals developed earlier and at a higher rate among animals bred in a pathogen-free environment than in a conventional environment (140). In addition, treating susceptible animals with infectious agents such as mycobacteria or virus not only protects animals from various autoimmune disease including T1D (145), EAE (146, 147) and lupus (148, 149) but also asthma (150-152).

c. Organ Transplantation

Immunological rejection of transplants is a normal function of a healthy immune system to eliminate foreign antigens. The inevitable challenge is how to convert a foreign transplantation antigen into a self-antigen, biologically, without long term use of non-specific immunosuppressive drugs. In this regard, the "Avidity Model" provides an immunological definition of a self-antigen versus a foreign antigen during adoptive immunity, which is not defined by the antigen itself but by the distinctive compositions of peripheral TCR repertoires to self versus to foreign antigens. Unlike the foreign repertoire, the self-repertoire is only composed of intermediate and low avidity self-reactive T cells, which can be used to define a self-antigen. The "Avidity Model" could thus provide a theoretical basis for innovative approaches to convert a foreign antigen into a self-antigen, which is not to manipulate the antigen but to modify the host TCR repertoire based on the avidity of allo-reactive T cells specific to the transplant. The currently employed clinical manipulations of non-specific suppression of immune response during the acute rejection phase probably reshape the T cell repertoire to the graft by wiping out the most activated clones, which are likely of high avidity. This may place the transplanted graft in a unique position between a foreign antigen and a self-antigen in relation to the immune system. Thus, if the immunological nature of the transplanted graft is assessed at different stages after transplantation by monitoring the host TCR repertoire based on the avidity of anti-allogenic T cells, it is possible to enable the immune system to treat the graft as a self-antigen. For example, if the graft survives the acute rejection by use of immuno-suppressive agents, the following chronic rejection may mainly be mediated by the residual allo-reactive T cells with intermediate avidity which are constantly being activated by the accepted graft in vivo. An effective approach to down-regulate these cells could be to re-activate the Qa-1/HLA-E dependent CD8+ T cell mediated regulatory pathway, which may have been impaired by the prior anti-rejection treatment during the acute rejection phase.

d. Tumor Immunology

A central question in tumor immunology is whether recognition of tumor antigens by the immune system leads to activation (i.e. immune surveillance) or tolerance, which depends on the nature of the tumor antigens (153). The conceptual framework of the "Avidity Model" may provide a different perspective to understand the development and treatment of tumor. If the tumor antigens are, behaving like foreign antigens, capable of eliciting effective anti-tumor immunity, which is composed of both high and intermediate avidity anti-tumor T cells, the tumor will be eliminated as a consequence of immune surveillance against tumor. However, if tumor antigens behave like self-antigens, the tumor can either fail to activate or only activate T cells with intermediate avidity. This could occur because high avidity T cells to the particular self-antigens are deleted by thymic negative selection. Alternatively, the particular tumor antigens may only elicit "poor" immune response, which represent anti-tumor response with low or intermediate avidity interactions due to insufficient presentation of tumor antigens (154-157). The biological significance of eliciting intermediate avidity anti-tumor immunity during tumorigenesis can not be ignored because the consequence of such immunity is to induce tolerance based on the conceptual framework of the "Avidity Model". Thus, the intermediate avidity anti-tumor T cells would be inhibited by the normal peripheral regulatory mechanisms, which evolved to control the potentially pathogenic auto-immunity. For example, Qa-1/HLA-E dependent CD8+ T cell mediated pathway, which is naturally induced from early childhood during certain infections, would down-regulate intermediate avidity T cells activated by any antigens, including tumor antigens and self-antigens. In such patients anti-tumor immunity would be inhibited by the normal regulatory mechanisms leading to the state of tolerance. Since anti-tumor T cells with intermediate avidity may be the only anti-tumor immunity in certain tumor patients, blockade of the regulatory pathways, such as the Qa-1/HLA-E dependent CD8+ T cells, to rescue these anti-tumor T cells, may be a potentially necessary therapy, in combination with other approaches. However, a potential complication of such therapy could be the increasing susceptibility to the development of organ specific autoimmune diseases, which would only be triggered during certain infections or vaccination with tumor cells presenting the particular self-antigens.

Consistent with this prediction are the observations that in addition to an apparent clinical anti-tumor effect, treatment of mice with B16 melanoma GM-CSF vaccine and anti-CTLA-4 exclusively resulted in vitiligo, an autoimmune response restricted to melanocytes. Similarly, mice receiving the prostate cancer-GM-CSF vaccine and anti-CTLA-4 develop prostatitis but no signs of global autoimmunity (132-

134). Based on the conceptual framework of the "Avidity Model", anti-CTLA-4 may render the anti-tumor T cells to escape the peripheral down-regulation by potently elevating the avidity of these cells, which are initially activated by sufficient level of the particular "self-antigen" presented by the vaccine tumor cells (see FIGS. 12 and 13). This is evidence supporting the hypothesis that biologically available self-antigens presented in the periphery is not sufficient to functionally activate any self-reactive T cells released from natural thymic negative selection which functional activation requires a higher level of antigen triggering. Otherwise, blockade of CTLA-4 pathway itself, in this case, would likely induce a rather global but not organ specific pathogenic autoimmunity.

Taken together, the conceptual framework of the "Avidity Model" permits novel clinical interventions to treat autoimmune disease and allergy or control rejection of organ transplants, by selectively inhibiting intermediate avidity T cells, to any antigens, without damaging the normal anti-infection and anti-tumor immunity, which is the major side affect of the currently used immuno-therapeutic drugs.

Cross-Protection in Autoimmune Disease

The studies below describe results that aid understanding the specificity of T cell regulation in the context of the conceptual framework of the "Avidity Model" by investigating the mechanism of antigen-peptide vaccination induced "cross-protection" phenomenon in two distinctive autoimmune disease models, Experimental Allergic Encephalomyelitis (EAE) and Type 1 Diabetes (T1D). It is shown herein that Qa-1 restricted CD8+ T cells, induced during vaccination of animals with different peptides, cross-protect animals from either EAE or T1D without suppressing the overall immune responses to foreign antigens. This is achieved by the Qa-1 restricted CD8+ T cells, which selectively down-regulate potentially pathogenic self-reactive T cells included in the pool of intermediate avidity T cells that are capable of preferentially expressing common surrogate target structure on their surface to be specifically down-regulated, independent of their antigen specificity. Thus, these studies provide experimental evidence that in the periphery, without the necessity of distinguishing self from non-self, the immune system discriminates self from non-self to specifically control potentially pathogenic auto-immunity and maintains self-tolerance, by selectively down-regulating intermediate avidity T cells to both self and foreign antigens.

"Cross-Protection" Between EAE and T1D is Mediated by the CD8+ T Cells

Identification of a surrogate target structure, Qa-1/Hsp60sp, expressed on intermediate avidity T cells and recognized by the Qa-1 restricted CD8+ T cells (described hereinabove and in 172) allows the prediction that the specificity of the regulation by the CD8+ T cells is not at the level of antigens that activate the target T cells. The specificity is at the level of perceiving a particular biological consequence of intermediate avidity T cell activation by recognizing the common surrogate target structure expressed regardless of which antigens the target T cells are triggered by.

To test this prediction in the context of pathogenic autoimmunity an experimental protocol was designed to investigate cross-protection mediated by Qa-1 restricted CD8+ T cells in two autoimmune disease models of Qa-1a strains, EAE in B10PL mice and T1D in NOD mice. B10PL mice or NOD mice were vaccinated with either 1-9Nac MBP (peptide X), or p277 (peptide Y) followed by induction of EAE with 1-9Nac MBP in B10PL mice or spontaneously developed T1D in NOD mice, which could be elicited by several self-antigens, including peptide B: 9-23 derived from insulin (peptide Z) (173). If the prediction is correct, the Qa-1 restricted CD8+ T cells primed by intermediate avidity T cells activated by peptide X or Y should be able to suppress the intermediate avidity T cells activated by peptide X or Z therefore protecting the animals from autoimmune disease elicited by either self-peptide X or Z (FIG. 14).

B10PL mice were vaccinated with either 1-9NacMBP, a MHC Class II biding peptide derived from MBP or p277, a MHC Class II biding peptide derived from Hsp60. In this regard, it is well known that 1-9NacMBP is a pathogenic peptide in B10PL mice and p277 may be involved in the pathogenesis of T1D in certain mouse strains (174) but irrelevant to EAE. As shown by FIG. 15a, animals were equally effectively protected from EAE by either 1-9Nac MBP or p277 vaccination compared with control mice vaccinated with incomplete Freund's adjuvant (IFA) alone. Thus, even when vaccinated with an irrelevant peptide, B10PL mice can be effectively protected from EAE, probably due to induction of Qa-1 restricted CD8+ T cells capable of cross down-regulating 1-9Mac MBP activated CD4+ T cells, which are responsible for the clinical EAE (see below).

The T1D model in NOD mice was then investigated. In this regard, it is known that p277, when used as a vaccine, effectively protects NOD mice from T1D, perhaps due to the induction of a shift from Th1 to Th2 response to the particular self-antigen (175). NOD mice were vaccinated with p277 peptide emulsified with IFA, which completely protected NOD mice from spontaneously developed T1D up to 35 week's of age compared with control mice only vaccinated with IFA. Reciprocally, NOD mice were also vaccinated with 1-9Nac MBP emulsified with IFA, which equally protected NOD mice from spontaneously developed T1D (FIG. 15b). The effectiveness of both 1-9NacMBP and p277 in the protection of either EAE or T1D disease models is defined here as cross-protection.

To test if the induction of the regulatory CD8+ T cells in vivo accounts for the cross-protection of EAE by either MBP or p277 vaccination in B10PL mice, the CD8+ T cells isolated from either 1-9Nac MBP or p277 vaccinated B10PL mice were adoptively transferred into naïve B10PL mice followed by induction of EAE. As shown in FIG. 15c, the CD8+ T cells isolated from both 1-9Nac MBP or p277 vaccinated but not control naive mice significantly protected recipient mice from subsequently induced EAE when adoptively transferred. Equal protection from spontaneously developed T1D was also obtained when the CD8+ T cells isolated from either p277 or 1-9Nac MBP vaccinated NOD mice were adoptively transferred into naïve NOD mice (FIG. 15d). Thus, CD8+ T cells primed during the vaccination with different peptides in the protected mice are capable of further preventing the animals from the subsequent development of either EAE or T1D in vivo, regardless of which peptides were used to vaccinate the donor animals.

In this regard, immunization of B10PL or NOD mice with foreign antigen HEL or HEL peptides (in IFA) also induced a CD8+ T cell dependent protection from either EAE or T1D as effectively as immunization with 1-9Nac MBP or p277 (data not shown). Control animals immunization with IFA alone did not induce the regulatory CD8 cells that protect animals from disease. These observations are consistent with the conceptual framework of the "Avidity Model".

Qa-1/Hsp60sp is a Common Target Structure Recognized by the CD8+ T Cells Isolated from Both Cross-Protected EAE and T1D Mice The "cross-protection" observed suggests that the regulatory CD8+ T cells recognize certain common target structures expressed by the susceptible target T cells, which are responsible for both EAE and T1D in vivo. It was considered that Qa-1/Hsp60sp, preferentially expressed on the intermediate avidity T cells and specifically recognized by the Qa-1 restricted CD8+ T cells, may represent one such target structure recognized by the CD8+ T cells that mediate the "cross-protection". To test this hypothesis, a Qa-1a expressing cell 3F4 was used as peptide-presenting cell to determine the specificity of the CD8+ T cells isolated from either 1-9Nac MBP or p277 vaccination protected B10PL and NOD mice.

3F4 was established as a Qa-1a expressing cell by transfecting the human B cell line C1R with recombinant murine Qa-1a cDNA (176, 177) and has been successfully served as a Qa-1 binding peptide-presenting cell to test if Hsp60sp is specific target for the Qa-1 restricted CD8+ T cells in previous studies in this laboratory. Physiological target T cells, the intermediate avidity 1-9Nac MBP specific clone 1AE10 from B10PL mice and p277 specific clone 15A6 from NOD mice served as positive controls, and low avidity MBP specific clone 4D10 and p277 specific clone 1304 served as negative control to assess the function and the specificity of the CD8+ T cells. It is noted that "quantitative" but not "qualitative" differences between the Qa-1/Hsp60sp versus Qa-1/Qdm is a function of avidity of T cell activation which determines their susceptibility to the down-regulation by the CD8+ T.

A significantly higher ratio of Qa-1/Hsp60sp versus Qa-1/Qdm in intermediate avidity T cells, reflected by the M/H/Qa-1 Protein Index, is the molecular basis for the susceptibility of intermediate avidity T cells to the down-regulation by the Qa-1 dependent CD8+ T cells.

In the current studies, illustrated in FIG. 16, significantly higher M/H/Qa-1 Protein Indexes were expressed by the two intermediate avidity clone 1AE10 and 15A6, compared with the two low avidity clone 4D10 and 13C4, consistent with their susceptibility to the down-regulation by the CD8+ T cells. As shown, CD8+ T cells isolated from either 1-9Nac MBP or p277 vaccination protected B10PL mice, which inhibited the positive control clone 1AE10, but not negative control clone 4D10, also efficiently down-regulated the 3F4 cells sensitized with Hsp60sp but not Qdm or control irrelevant peptide (FIG. 17*a*).

Similarly, CD8+ T cells isolated from either p277 or 1-9Nac MBP vaccination protected NOD mice, which inhibited the positive control clone 15A6, but not negative control clone 13C4, efficiently down-regulated the 3F4 cells sensitized with Hsp60sp but not Qdm or control irrelevant peptide (FIG. 17*b*). CD8+ T cells isolated from naïve B10PL or NOD mice did not have any effect on the target cells (data not shown).

This set of experiments unequivocally demonstrated that Qa-1/Hsp60sp represents a common target structure, which can be specifically recognized by the Qa-1 restricted CD8+ T cells that are induced during vaccination of mice with different antigen peptides. Thus, Qa-1/Hsp60sp, expressed on the cell surface, can prime and be subject to the CD8+ T cells that account for the in vivo amelioration of both EAE and T1D. These results are consistent with the observation that Qa-1 restricted CD8+ T cells can be directly induced by Hsp60sp loaded DCs, which protect animals from subsequently induced EAE.

The CD8+ T Cells Suppress the Overall Immune Responses to Self but not to Foreign Antigens It is preferable to determine if the CD8+ T cells, accounting for the "cross-protection" of EAE and T1D, are capable of discriminating self from non-self in the periphery. This is important to understand the relationship between the specificity of T cell regulation and self non-self discrimination. Whether the down-regulation by the Qa-1 restricted CD8+ T cells induced during peptide vaccination is an intrinsic mechanism that non-specifically inhibits overall immune responses to both self and foreign antigens or whether it specifically suppresses auto-immunity without damaging the ongoing immune responses to foreign antigens was addressed herein (178).

The effect of the CD8+ T cells on the overall immune responses to self versus to foreign antigens was assessed by T cell adoptive transfer experiments. The two self-peptides chosen to assess the in vivo autoimmune responses were 1-9Nac MBP, which is the pathogenic peptide for EAE in B10PL mice and B: 9-23, a peptide from Insulin known to be involved in the pathogenesis of T1D in NOD mice (173). Thus, CD8+ T cells isolated from either 1-9NacMBP or p277 vaccinated mice were adoptively transferred into naïve mice which were subsequently challenged with either self or foreign antigens in vivo. The effect of the transferred CD8+ T cells on the immune responses to self versus to foreign antigens was assessed and compared by an ex-vivo assay.

As shown, T cells derived from mice, which were transferred with CD8+ T cells from either 1-9NacMBP or p277, vaccinated mice, revealed an inhibited overall response to self-antigens in a standard ex-vivo T cell proliferation assay. This was shown by a lower magnitude of T cell proliferation, to self-peptide 1-9NacMBP in B10PL mice (FIG. 18*a*), and B: 9-23 in NOD mice (FIG. 18*b*), in combination with a decreased overall avidity, reflected by a higher ED50, compared with mice received control CD8+ T cells. The inhibited in vivo T cell responses to pathogenic self-peptides 1-9Nac MBP and B: 9-23 by the adoptively transferred CD8+ T cells from either 1-9NacMBP or p277 vaccination protected mice is consistent with the in vivo cross-protection of the diseases observed.

In contrast, the same regulatory CD8+ T cells, when adoptively transferred, enhanced the overall primary immune response to the conventional foreign antigen HEL in both B10PL (FIG. 18*a*) and NOD (FIG. 18*b*) mice, shown by a higher magnitude of T cell proliferation combined with an increased overall avidity, reflected by a lower ED50, compared with mice received control CD8+ T cells. Thus, the overall inhibitory effect of suppression observed in "cross-protection", mediated by the Qa-1 restricted CD8+ T cells, is selectively confined within the immune responses to self but not to foreign antigens.

Human Studies

Data obtained in human studies support the concept established in the murine studies. It was found that that HLA-E/Hsp60sp is also the specific target recognized by the HLA-E restricted CD8+ T cells. The data showed that HLA-E restricted CD8+ T cell can be generated in vitro by priming the purified CD8+ T cells with Hsp60sp (experimental) or B7sp (control) loaded dendritic cells in vitro, CD8(H) or CD8(B). It was found that CD8(H) but not CD8(B) specifically inhibit the HLA-E transfected clones loaded with Hsp60sp but not B7sp.

Type 1 Diabetes

Studying the mechanisms that control the development of T1D in NOD mice has been a major focus to understand the development and control of auto-immune disease in the field of immune regulation. In this regard, particularly interesting are the studies of rodent models and preliminary studies in man showing that the completion of beta cell destruction can be considerably delayed or prevented by peritoneal administration of cell self-antigens-including insulin, GAD, and Hsp60. Although the mechanism of self-antigen vaccination induced protection of T1D is currently unclear, these advances have set the stage for developing a complete molecular understanding of the pathogenesis of this autoimmune disease and for an effective means of prevention. Prevention could then replace insulin therapy, which is effective but associated with long-term renal, vascular, and retinal complications.

Studies on cross-protection of auto-immune disease mediated by the Qa-1 restricted CD8+ T cells were extended into T1D model in NOD mice. Peptide vaccination induced complete protection of T1D in NOD mice showing mediation by Qa-1 restricted CD8+ T cells that function to discriminate self from nonself in the periphery. The function of self-nonself discrimination is accomplished via a specific recognition, by the Qa-1 restricted CD8+ T cells, of the common target structure, Qa-1/Hsp60sp complexes, preferentially expressed on the intermediate avidity T cells. Thus, in general, although a considerable research effort has centered on studying the role of immune regulation in the pathogenesis of autoimmunity and treatment of T1D, this research has focused predominately on mechanisms controlling the magnitude and class of immune responses and not on studies directed to the cognitive aspects of regulation, including the central issue of self-nonself discrimination. The strong association that exists between specific MHC class II alleles and disease susceptibility implies that the diabetogenic response involves antigen driven activation of CD4+ T cells. Studies in the NOD mouse from the neonatal period until disease onset suggest that the diabetogenic response can be viewed as a series of stages culminating in massive beta islet cell destruction and the establishment of overt diabetes. Peri-insulinitis, first seen at 4-6 weeks of age, is characterized by an accumulation of macrophages, dendritic cells, and B and T lymphocytes that enter the periductal areas but remain outside of the islet proper. Later intra-insulitis develops which is characterized by the direct invasion of the islets by infiltrating cells, and is dependent on the recognition of pancreatic beta cell antigen(s). The distribution of islets with insulitis in the pancreas of patients with newly diagnosed T1D can be strikingly uneven. Histologic studies suggest that an 80 percent reduction in the volume of beta cells is required to induce symptomatic T1D. Interestingly, although histologic evidence of islet regeneration is uncommon, it is found in the pancreas of some young patients with T1D. Taken together these observations suggest that there is a window of opportunity during the early stages in the pathogenesis of T1D, when immune intervention is more likely to significantly retard the progression of beta cell destruction mediated by self-reactive T cells. In this regard, model of T1D in NOD mice provides unique opportunity for in vivo studies of natural history of T1D, compared with the parallel human studies.

Figures 20A, 20B, 20C, 20D:
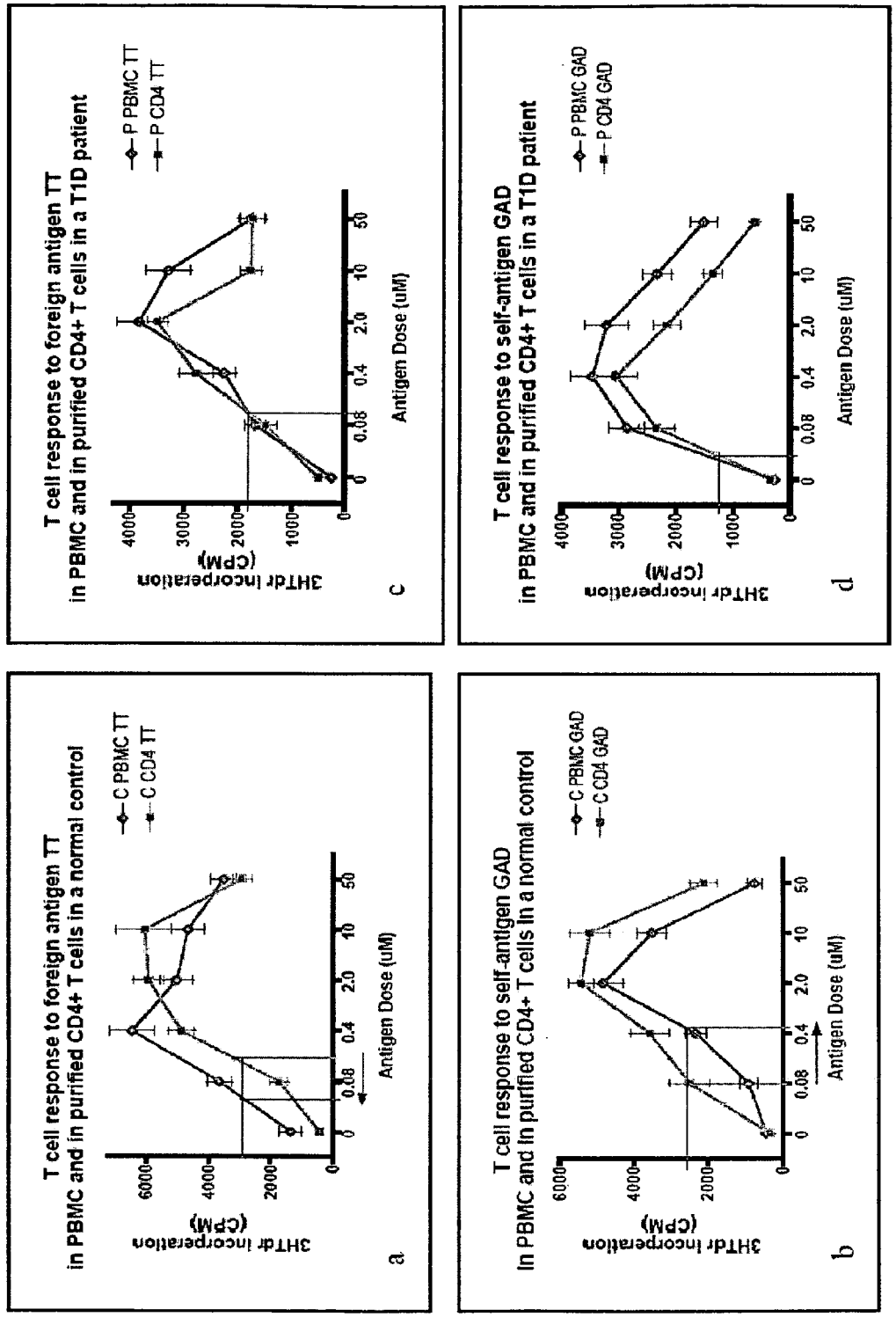
Figure 20E:
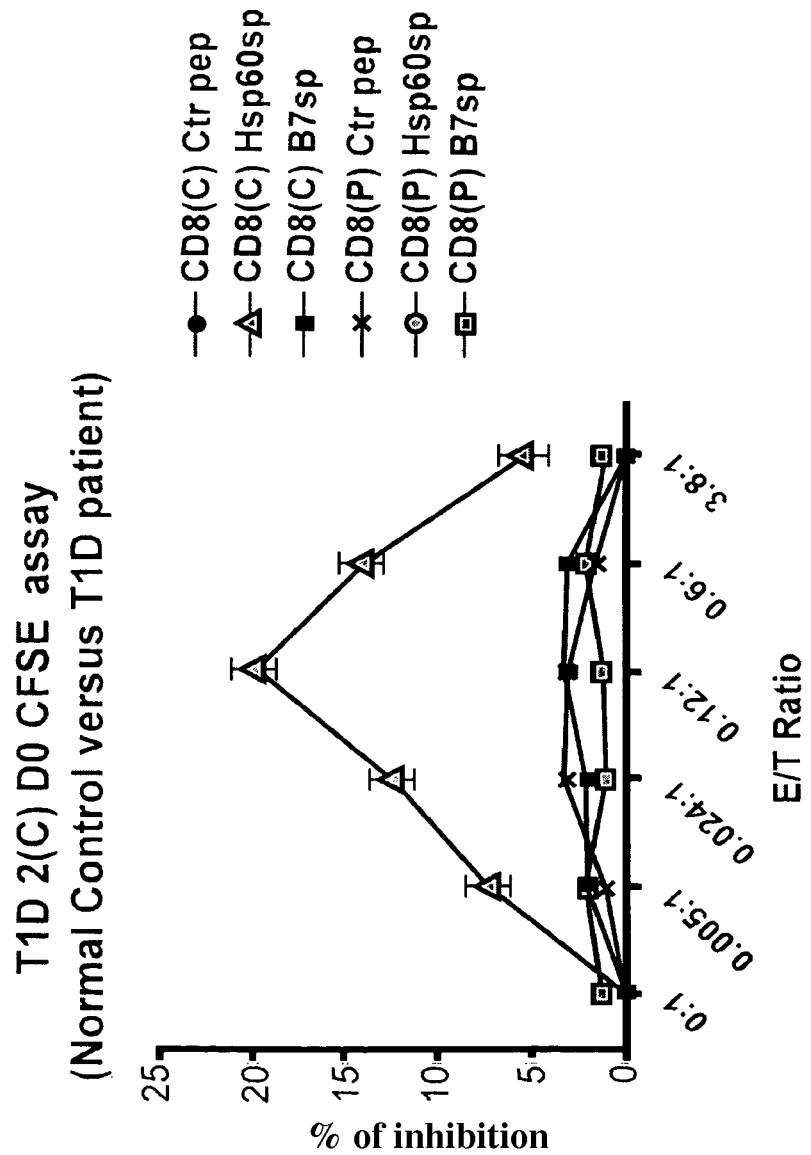

In the earlier studies herein it was demonstrated that Qa-1 restricted CD8+ T cells controls the development of T1D in NOD mice by means of discriminating self from nonself. To test if HLA-E restricted CD8+ T cells also play a similar role in the control of human T1D, the function of CD8+ T cells in freshly isolated PBMC from T1D patients was first tested. For this purpose two assays were employed. The first is a standard T cell proliferation assay measuring self non-self discrimination, comparing the overall immune responses of human PBMC to self versus foreign antigens in the presence or absence of CD8+ T cells. Thus, intact PBMC populations or purified CD4+ T cells were cultured with varying doses of the self-antigen GAD or foreign antigen TT. Comparing PBMC with purified CD4+ T cells could not alone definitively pinpoint the function of the CD8+ T cells contained in the PBMC. However, after large scale experiments performed using purified CD8+ T cells as effectors to show that HLA-E restricted CD8+ T cells, indeed, are capable of discriminating self from non-self, comparing the immune response of PBMC versus purified CD4+ T cells could then be used as a quick read out for the function of the CD8+ T cells in combination with other assays. This is the case in testing the function of CD8+ T cells in T1D patients combined with the CD8+ T cell inhibition CFSE assay, which can be applied as a relative simple and feasible clinical test. It was found that CD8+ T cells in PBMC from normal control significantly depressed the response to the self-antigen GAD, reflected by an increased ED50 (FIG. 20b), while enhancing the response to foreign antigen TT, reflected by a decreased ED50 (FIG. 20a), compared with purified CD4+ T cells. However, when the same test was performed on PBMC from T1D patients, there was no significant difference between PBMC and purified CD4+ T cells responding to either self-antigen GAD, or to foreign antigens TT (FIGS. 20c and d), suggesting that CD8+ T cells from T1D patients have lost the capacity to discriminate self from nonself. We then proceeded to further identify the specificity of the CD8+ T cells. Thus, purified CD8+ T cells from T1D patients were tested on HLA-E transfectant H3B2 cells loaded with Hsp60sp. H3B2 loaded with B7sp or non-HLA-E binding peptide served as controls. As shown in FIG. 20E, while CD8+ T cells from normal controls specifically inhibited H3B2 loaded with Hsp60sp, but not control peptides (C), CD8+ T cells from a T1D patient (P) failed to inhibit H3B2 loaded with Hsp60sp. In all the T1D patients tested (11 total patients tested), CD8+ T cells from freshly isolated PBMC failed to specifically inhibit H3B2 loaded with Hsp60sp, and also failed to discriminate self from nonself. These preliminary studies strongly suggest that HLA-E restricted CD8+ T cells participate in the immunopathogenesis of human T1D.

CD8+ T cells were in vitro primed with DCs loaded with either Hsp60sp [CD8(H)], or B7sp [CD8(B)] and tested for their specificity and the function of self-nonself discrimination using the two assays described above. As shown in FIGS. 21C and D, CD8+ T cells regained the function of self-nonself discrimination after in vitro boosting by DCs loaded with Hsp60sp, compared with the CD8+ T cell lines generated from normal controls (FIGS. 21A and B). To verify the restored function of the CD8+ T cells, these CD8+ T cell lines were also tested in a CFSE assay on HLA-E transfectant H3B2 cells loaded with Hsp60sp. A CD8(B) line from each patient served as control. As shown in FIGS. 21Ee and 21F, CD8(H) from a T1D patient specifically inhibited H3B2 loaded with Hsp60sp, as effectively as the normal healthy individual, but not when loaded with B7sp or control peptide. CD8(B) from the same patient did not inhibit at all. This phenomenon has been observed in about 60% of the 10 total T1D patients tested to date. This is evidence that HLA-E restricted CD8+ T cells that function by self-nonself discrimination exist in normal healthy humans and also participate in the control of human T1D As importantly, our preliminary studies also show that we have established innovative and novel assay systems as well as cellular and molecular reagents that should enable us to make significant progress in continuing to translate the basic science of the HLA-E/Qa-1 restricted CD8+ T cell mediated pathway that function by self-nonself discrimination to the direct study of human regulatory T cells and to human autoimmune diseases under the context of the "Avidity Model".

Discussion

These studies address the relationship between the specificity of peripheral immune regulation and self non-self discrimination in the control of autoimmune diseases. The intriguing feature of the in vivo "cross-protection" described in these studies is the observation that vaccination with same antigenic peptides efficiently protects animals from two distinctive autoimmune diseases in which the pathogenic self-antigens responsible for the diseases differ from each other and the target organs, attacked by the autoimmune process, also differ. Equally interesting is the observation that independent of whether or not the vaccine peptides are responsible for a given autoimmune disease, vaccinating animals with different antigen peptides effectively protects animals from the same autoimmune disease. Moreover, the suppression that mediates the cross-protection phenomenon is only confined within the overall immune responses to self-antigens without damaging the normal ongoing immune responses to foreign antigens.

The cross-protection phenomenon strongly points to recognition of a common target structure on potentially pathogenic self-reactive T cells, expressed as a consequence of T cell activation during autoimmune process, by the Qa-1 restricted CD8+ T cells, accounting for the effective in vivo amelioration of autoimmune diseases observed. In light of the experimental evidence that the potentially pathogenic self-reactive T cells are included in the pool of intermediate avidity self-reactive T cells, it was shown above that the preferential expression of Qa-1/Hsp60sp on certain activated T cells is a function of the avidity of their TCR-ligand interactions. It is further demonstrated in the current studies that Qa-1/Hsp60sp, indeed, represents a common target structure recognized by the Qa-1 restricted CD8+ T cells isolated from either cross-protected EAE or T1D mice (FIGS. 17a and 17b). "Cross-protection" occurs because potentially pathogenic self-reactive T cells included in the pool of intermediate avidity T cells, when activated, are capable of preferentially expressing Qa-1/Hsp60sp on their surface and as a consequence become subject to down-regulation by the CD8+ T cells, regardless of which self-antigens the target T cells are triggered by.

Preferential expression of a common target structure, such as Qa-1/Hsp60sp, on the intermediate avidity T cells activated by any self-antigens, which are responsible for a given autoimmune disease in vivo, establishes the molecular and cellular basis for the cross-protection. We envision that upon self peptide vaccination, the common target structure generated is essential to trigger the common target structure specific TCRs expressed by the regulatory CD8+ T cells to differentiate into effector cells in vivo (the induction phase). The primed CD8+ T cells then, in turn, down-regulate potentially pathogenic self-reactive T cells, by recognizing the common target structure preferentially expressed as a consequence of intermediate avidity T cell activation by any self-antigens (the effector phase). The animals are, therefore, protected from the development of any given autoimmune disease by these CD8+ T cells. Thus, the regulatory CD8+ T cells primed by intermediate avidity T cells activated by vaccine peptides during the primary responses would selectively down-regulate intermediate avidity T cells activated by any different set of self-antigens during later immune responses, which are responsible for a given autoimmune disease in vivo (FIG. 19).

Since T cells are not professional APCs, it may be that the professional APCs, such as dendritic cells may be recruited and function to provide co-stimulatory signals to prime the regulatory CD8+ T cells during the induction phase of the pathway. Alternatively, the regulatory CD8+ T cells could also be directly primed by the relevant Qa-1 expressing DCs which are capable of cross presenting the common target structure, such as Qa-1/Hsp60sp, by engulfing and processing Hsp60 protein released from damaged cells during the primary immune response initiated by infections or injuries. In the other studies above it was shown that regulatory CD8+ T cell can be directly induced by Qa-1 expressing DCs loaded with Hsp60sp in vivo to protect animals from the subsequently induced EAE. The precise function of DCs in priming the Qa-1 restricted CD8+ T cell pathway needs to be further investigated.

In the studies presented herein, the two self-peptides, functioning as effective vaccines are both MHC Class II binding peptides which are capable of eliciting effective MHC Class II responses in both B10PL and NOD mice. Although 1-9NacMBP is a self-peptide responsible for pathogenic autoimmune EAE in B10PL mice (179) and p277 can induce T1D in certain mouse strains (174) and therefore may be involved in T1D in NOD mice, there is no evidence that p277 can induce EAE in B10PL mice or that 1-9NacMBP can induce T1D in NOD mice. Interestingly, both peptides are equally capable of preventing either EAE or T1D in vaccinated animals. This key observation indicates that independent of whether or not the vaccine peptides are pathogenic to a given autoimmune disease, as long as they are able to initiate an immune response to provide the common target structures, such as Qa-1/Hsp60sp, to prime the Qa-1 restricted CD8+ T cells, they are capable of cross-protection (FIG. 19). Thus, via specific recognition of the common target structures, cross-protection is accomplished by a selective down-regulation of the relevant pathogenic self-reactive T cells activated by particular self-antigens responsible for a given autoimmune disease in vivo, which could be either relevant or irrelevant to the vaccine peptide/s.

It is important to emphasize that, conceptually, the intermediate avidity T cells described in the "Avidity Model" represent a rather large pool of thymic escapees that have the avidity lower than those deleted in the thymus but cover a wide spectrum of avidity. It could extend from a high end close to the low boundary of the threshold of thymic negative selection to a low end, which might be near the high boundary of the threshold of thymic positive selection. The exact biological threshold of the "intermediate avidity" has not yet been identified. It may vary to a certain extent in different experimental systems. In this regard, it has been shown in several studies that certain self-reactive T cells with "low avidity", presumably at the low end of the intermediate avidity referred to, can be activated in the periphery to initiate autoimmune diseases, such as 1-9NacMBP specific encephalitogenic clones in B10PL mice. On the other hand, in some autoimmune diseases, pathogenic self-reactive T cells appear to have much higher avidity to self-antigens, probably at the high end of the spectrum of the intermediate avidity, such as certain pathogenic diabetic clones in NOD mice (14). The observations that Qa-1 restricted CD8+ T cells protect animals from both EAE and T1D in our current studies are consistent with the notion that this regulatory pathway selectively down-regulate intermediate avidity self-reactive T cells, which are covered by a rather wide spectrum of avidity in the periphery.

"Cross-protection" across distinctive autoimmune diseases provides biological evidence for the hypothesis that perceiving the avidity of T cell activation can be translated into peripheral T cell regulation to discriminate self from non-self in the periphery independent of the antigen specificity of the T cells regulated. In this regard, the "Avidity Model" contains an important conceptual element of "ergotypic regulation" in that both types of regulation recognize the consequence of T cell activation, regardless what antigens that activate the target T cells. However, it also differs from "ergotypic regulation" because the "ergotypic regulation" does not consider the avidity of T cell activation (180, 181).

A truncated self-reactive repertoire, generated by thymic negative selection that is devoid of high avidity T cells, is the biological basis for the concept that self non-self discrimination can be achieved in the periphery by a simple and unified mechanism of selective down-regulation of intermediate avidity T cells to both self and foreign antigens. As a consequence of specific recognition of common surrogate target structures, which are preferentially expressed on intermediate but not high avidity T cells, intermediate avidity T cells activated by any self or foreign antigens are capable of, not only inducing but also, being targeted for the down-regulation whereas high avidity T cells activated by any foreign antigens would escape the down-regulation (FIG. 19). This explains why Qa-1 restricted CD8+ T cells that account for the in vivo cross-protection were also observed to specifically inhibit the overall immune responses to self-antigens 1-9NacMBP and B: 9-23 but not to foreign antigen HEL in the current studies (FIG. 18). This set of data are consistent with the prior observation that Qa-1 restricted CD8+ T cells inhibit the overall immune response to HEL in the biological context of self-antigen in the HEL TG mice but enhance the immune response to the same antigen in the biological context of foreign antigen in the WT mice. The studies, thereby, consistently reveal that the unified mechanism of selective down-regulation of intermediate avidity T cells has opposing overall effects on immune responses to self versus to foreign antigens: maintaining self-tolerance while optimizing, or at least not damaging, the immune responses to foreign antigens, a functional status of self non-self discrimination. This is because among T cells activated by foreign antigens only those of intermediate avidity are down-regulated by the CD8+ T cells while the T cells with high avidity to the foreign antigens not only escape the down-regulation, but could also be indirectly promoted to grow, probably due to less competition for space and nutrition. On the other hand, since the self-reactive repertoire is mainly composed of intermediate and low but devoid of high avidity T cells the overall effect of the down-regulation of intermediate avidity T cells in the context of self-antigen is the absolute suppression of autoimmunity.

Taken together, the distinctive composition of the naïve peripheral T cell repertoires to self versus to foreign antigens determines the opposing overall biological consequences of selective down-regulation of the intermediate avidity T cells to self versus to foreign antigens. This is the core value of the "Avidity Model" that forms the conceptual framework for a new paradigm to explain, at a biological system level, how the immune system achieves self non-self discrimination during adaptive immunity, without the necessity to distinguish self from non-self in the periphery at the level of T cell regulation. Thus, the immune system discriminates self from non-self, during adaptive immunity, not by recognizing the structural differences between self versus foreign antigens, but rather by perceiving the avidity of T cell activation. In general, selective down-regulation of intermediate avidity T cells specific to any antigens, in the context of a truncated repertoire devoid of high avidity T cells, is a biological approach that the immune system achieves peripheral self-tolerance. However, the same mechanism of selective down-regulation of intermediate avidity T cells specific to any antigens, in the context of a completed repertoire containing high avidity T cells, would facilitate the dominance of the high avidity T cells to enhance the particular immune response. It is essential to understand that self non-self discrimination achieved by selective down-regulation of intermediate avidity T cells in the periphery can only be sustained by the distinctive compositions of a truncated self-reactive repertoire versus a completed foreign-reactive repertoire generated by thymic negative selection.

In summary, the notion that "perceiving" the avidity of T cell activation can be translated into peripheral T cell regulation is the essence of the "Avidity Model" that provides a conceptual framework to understand the biological inevitability that the consequence of thymic negative selection determines how the adaptive immunity is regulated in the periphery to accomplish self/non-self discrimination. The physical link between thymic negative selection and peripheral immune regulation is the fact that release of intermediate avidity self-reactive T cells into the periphery, which contain potentially pathogenic self-reactive T cells, is a biological consequence of thymic negative selection and must be specifically dealt with by peripheral regulatory mechanisms. The Qa-1 restricted CD8+ T cell mediated regulatory pathway represents an example of peripheral mechanisms that the immune system evolved to complete the self non-self discrimination that is achieved, imperfectly, by thymic negative selection, in order to maintain self-tolerance. These regulatory mechanisms differ from the intrinsic mechanisms that control the magnitude and class of immune responses, such as antigen activation induced cell death or expression of co-stimulatory molecules, or the functional activation and differentiation of the CD4+ T cells into the Th1 versus Th2 or Tr1 and Tr3 regulatory cells (178). They also differ from the "naturally arising CD25+Foxp3+ Tregs" that negatively control the overall immune responses to both self and foreign antigens (182).

Notably, because the specificity of the regulation is not at the level of the antigens that activate the target T cells, control of autoimmune diseases can be achieved independent of the knowledge of the particular self-antigens involved in any given autoimmune disease, which antigens are largely undetermined at the present time.

Materials and Methods for Cross-Protection Study

Animals

All mice used (Jackson labs) are housed in the pathogen-free animal facility associated with the Columbia University Department of Comparative Medicine. Institutional Animal Care and Use Committee at Columbia University provided approval for all animal studies.

Reagents:

Anti-Qa-1a antisera are a kind gift from Dr. Lorraine Flaherty at D. Axelrod Institute for Public Health. The staining reagents, Fluorescein (Fl) 53-6.72 (anti mouse CD8), Phycoerythorine (PE)—GK1.5 (anti mouse CD4) were purchased from Pharmingen. Phycoerythorine (PE)—goat anti-mouse was purchased from Jackson ImmunoResearch Laboratory. Peptides Hsp60sp (QMRPVSRAL) (SEQ ID NO:2), B: 9-23 (SHLVEALYLVCGERG) (SEQ ID NO:12) are synthesized by GeneScript Corporation. Peptides Qdm (AMAPRTLLL), p277 (SEQ ID NO:1), (VLGGGVALLRVIPALDSLT-PANED) (SEQ ID NO:13) and 1-9NacMBP (AcAS-GLAPSGA) (SEQ ID NO:14) are synthesized by protein core facility at Columbia University.

SDS-PAGE and Western Blot Analysis

SDS-PAGE and Western blotting were conducted following standard procedures. 1-9Nac MBP or p277 specific CD4+ clones with different avidity were stimulated with irradiated splenic cells (APC) and antigen peptide/s (1-50 uM) for 72 hrs. The Abs used were: anti-actin, anti-Hsp60, anti-MHC Class Ia M1/42 and anti-Qa-1a sera, followed by incubation with the secondary Ab rabbit anti-mouse HRP or rabbit anti-Rat HRP. Target proteins were detected using the ECL detection kit (Amersham Biosciences). All blots were densitometrically quantitated using ChemiDoc XRS Imager Quantity one-4.5.0 software (Bio-rad).

CD8+ T Cell Inhibition Assay

CD8+ T cells were purified with CD8 MACS magnetic beads (Miltenyibiotec, Inc. Auburn Calif.). 3F4 cells were passively loaded with peptides overnight at 26° C. Equal number of unlabeled 3F4 cells loaded with peptides and CFSE labeled 3F4 cells that are not loaded with peptide were mixed and a graded number of CD8+ T cells were added to the targets. CD8+ T cells from naïve mice serve as control and we have established that these CD8+ T cells have no effect on the activated target T cells. The actual 1-9Nac MBP specific intermediate avidity T cell clone 1AE10, a physiological target of the Qa-1 restricted CD8+ T cells and a low avidity clone 4D10 as positive and negative controls were built in all the functional assays in B10PL mice, and p277 specific intermediate avidity T cell clone 15A6 and a low avidity clone 13C4 were in NOD mice. In addition, in all assays, CD8+ T cells tested have no effect on C1R cells pulsed with Hsp60sp or Qdm. 4 days later, the cell mixtures were stained with anti-mouse CD8-PE mAb to distinguish CD8+ T cells from target cells and the CD8+ T cells were gated out during the analysis when the ratio between two types of targets were calculated. The ratio between peptide-loaded (non-CFSE-labeled) 3F4 cells and non-loaded (CFSE labeled) 3F4 cells in the presence of CD8+ T cells was determined as % of specific inhibition: {[the ratio of loaded versus unloaded 3F4 cells in control cultures (without CD8+ T cells)–the ratio in experimental cultures (with CD8+ T cells)]/the ratio in control cultures}×100%.

Peptide Vaccination and Adoptive Transfer of CD8+ T Cells in EAE and T1D Models

In the standard protocol used throughout this study female 8-10 weeks old B10PL or 3-4 weeks old NOD mice were immunized subcutaneously with 1-9Nac MBP or p277 emulsified with IFA at 100 uM/mouse as described. EAE was induced at least one week after peptide vaccination. CD8+ T cells were purified from spleens and draining lymph nodes of peptide vaccination protected EAE/B10PL mice or T1D/NOD mice by positive selection with CD8 MACS magnetic beads (Miltenyibiotec, Inc. Auburn Calif.). The purity of CD8+ T cells is routinely >95%. 2-5×106 CD8+ T cells were intravenously adoptively transferred into naïve NOD mice or B10PL mice, which were subsequently induced to develop EAE one week later.

The effect of peptide vaccination or adoptive transfer of CD8+ T cells was evaluated by assessing the clinical EAE (181) or T1D in the recipient mice. Spontaneously developed T1D was assessed by measuring the serum levels of glucose every other day. Mice with glucose level beyond 250 dg/ml for two measurements were considered diabetic.

Ex-Vivo Assay to Assess the Effect of CD8+ T Cells on Immune Responses to Self Versus to Foreign Antigens The B10PL or NOD mice adoptively transferred, at 2-5×106 cells/mouse, with CD8+ T cells isolated from either 1-9NacMBP or p277 vaccination protected mice were challenged with either self-antigen (1-9MacMBP in B10PL mice or B: 9-23 in NOD mice) or foreign antigen (HEL) one day after the cell transfer. On day 7-9, single cell suspension were prepared from draining lymph nodes and 1×106 LNC or 0.25×106 purified CD4+ T cells plus 1×106 irradiated splenic cells were plated in flat bottom 96 well plates in AIM-V serum free lymphocyte medium (GIBCO) supplemented with L-glutamine at 1 mM. Antigens were added in the concentration ranging from 0.03-300 uM. During the last 18 hours of 4-day culture, 3H thymidine was added (1 uCi/well) and incorporation of labeling was measured by liquid scintillation counting. Cell proliferation, as counts per minute, was plotted against antigen concentration, and the ED50 value was derived by calculating the intercept of antigen concentration leading to half maximum proliferation (183,184).

REFERENCES

1. H. Jiang, Y. Wu, B. Liang et al., *J Clin Invest* 115 (2), 302 (2005).
2. H. Jiang and L. Chess, *Annu. Rev. Immunol.* 18, 185 (2000).
3. H. Jiang, S. I. Zhang, and B. Pernis, *Science* 256 (5060), 1213 (1992).
4. Dow-Rhoon Koh, Wai-Ping Fung-Leung, Alexandra Ho et al., *Science* 256, 1210 (1992).
5. D. Hu, K. Ikizawa, L. Lu et al., *Nat Immunol* 5 (5), 516 (2004).
6. J. W. Kappler, N. Roehm, and P. Marrack, *Cell* 49 (2), 273 (1987); H. Hengartner, B. Odermatt, R. Schneider et al., *Nature* 336 (6197), 388 (1988); H. Pircher, U. H. Rohrer, D. Moskophidis et al., *Nature* 351 (6326), 482 (1991).
7. S. M. Anderton, C. G. Radu, P. A. Lowrey et al., *J Exp Med* 193 (1), 1 (2001); B. Han, P. Serra, J. Yamanouchi et al., *J Clin Invest* 115 (7), 1879 (2005); D. Zehn and M. J. Bevan, *Immunity* 25 (2), 261 (2006).
8. H. Jiang, S. Curran, E. Ruiz-Vazquez et al., *Proc Natl Acad Sci USA* 100 (14), 8378 (2003).
9. C. J. Aldrich, R. Waltrip, E. Hermel et al., *J Immunol* 149 (12), 3773 (1992).
10. L. C. Lowen, C. J. Aldrich, and J. Forman, *J Immunol* 151 (11), 6155 (1993).
11. L. A. Cotterill, H. J. Stauss, M. M. Millrain et al., *Eur J Immunol* 27 (9), 2123 (1997); Z. Kurepa, C. A. Hasemann, and J. Forman, *J Exp Med* 188 (5), 973 (1998).
12. F. Imani and M. J. Soloski, *Proc Natl Acad Sci USA* 88 (23), 10475 (1991).
13. T. Chun, C. J. Aldrich, M. E. Baldeon et al., *Immunology* 94 (1), 64 (1998).
14. J. Michaelsson, C. Teixeira de Matos, A. Achour et al., *J Exp Med* 196 (11), 1403 (2002).
15. B T Sher, R Nairn, J E Coligan et al., *Proc Natl Acad Sci USA* 82 (4), 1175 (1985).
16. D. J. Connolly, L. A. Cotterill, R. A. Hederer et al., *J Immunol* 151 (11), 6089 (1993).
17. W. F. Lo, H. Ong, E. S. Metcalf et al., *J Immunol* 162 (9), 5398 (1999).
18. H. Jiang, R. Ware, A. Stall et al., *Immunity* 2 (2), 185 (1995).
19. H. Jiang, N. S. Braunstein, B. Yu et al., *Proc Natl Acad Sci USA* 98 (11), 6301 (2001).
20. A. Davies, S. Kalb, B. Liang et al., *J Immunol* 170 (10), 5027 (2003).
21. F. Gays, K. P. Fraser, J. A. Toomey et al., *J Immunol* 166 (3), 1601 (2001).
22. J. Hackett, Jr., C. Stebbins, B. Rogerson et al., *J Exp Med* 176 (1), 225 (1992); C. J. Jolly, S. D. Wagner, C. Rada et al., *Semin Immunol* 8 (3), 159 (1996); S. D. Wagner and M. S, Neuberger, *Annu Rev Immunol* 14, 441 (1996); M. K. Slifka and J. L. Whitton, *Nat Immunol* 2 (8), 711 (2001).
23. R. Ware, H. Jiang, N. Braunstein et al., *Immunity* 2 (2), 177 (1995); J. Li, I. Goldstein, E. Glickman-Nir et al., *J Immunol* 167 (7), 3800 (2001).
24. T. Takai, M. Li, D. Sylvestre et al., *Cell* 76 (3), 519 (1994).
25. S. Basu, R. J. Binder, T. Ramalingam et al., *Immunity* 14 (3), 303 (2001).
26. Cohn M. 2004. Whither T-suppressors: if they didn't exist would we have to invent them? *Cell Immunol* 227: 81-92

27. Jiang H, Chess L. 2006. Regulation of immune responses by T cells. *N Engl J Med* 354: 1166-76
28. Medzhitov R, Janeway C A, Jr. 2002. Decoding the patterns of self and nonself by the innate immune system. *Science* 296: 298-300
29. Janeway C A, Jr., Medzhitov R. 2002. Innate immune recognition. *Annu Rev Immunol* 20: 197-216
30. Medzhitov R, Janeway C, Jr. 2000. Innate immunity. *N Engl Med* 343: 338-44
31. Litman G W, Anderson M K, Rast J P. 1999. Evolution of antigen binding receptors. *Annu Rev Immunol* 17: 109-47
32. Davis M M. 2004. The evolutionary and structural 'logic' of antigen receptor diversity. *Semin Immunol* 16: 239-43
33. Kappler J W, Roehm N, Marrack P. 1987. T cell tolerance by clonal elimination in the thymus. *Cell* 49: 273-80
34. Hengartner H, Odermatt B, Schneider R, Schreyer M, Walle G, MacDonald H R, Zinkernagel R M. 1988. Deletion of self-reactive T cells before entry into the thymus medulla. *Nature* 336: 388-90
35. Pircher H, Rohrer U H, Moskophidis D, Zinkernagel R M, Hengartner H. 1991. Lower receptor avidity required for thymic clonal deletion than for effector T-cell function. *Nature* 351: 482-5
36. Grossman Z, Paul W E. 2001. Autoreactivity, dynamic tuning and selectivity. *Curr Opin Immunol* 13: 687-98
37. Grossman Z, Min B, Meier-Schellersheim M, Paul W E. 2004. Concomitant regulation of T-cell activation and homeostasis. *Nat Rev Immunol* 4: 387-95
38. Matzinger P. 1994. Tolerance, danger, and the extended family. *Annu Rev Immunol* 12: 991-1045
39. Matzinger P. 2002. The danger model: a renewed sense of self. *Science* 296: 301-5
40. Jiang H, Curran S, Ruiz-Vazquez E, Liang B, Winchester R, Chess L. 2003. Regulatory CD8+ T cells fine-tune the myelin basic protein-reactive T cell receptor V beta repertoire during experimental autoimmune encephalomyelitis. *Proc Natl Acad Sci USA* 100: 8378-83. Epub 2003 Jun. 24.
41. Han B, Serra P, Yamanouchi J, Amrani A, Elliott J F, Dickie P, Dilorenzo T P, Santamaria P. 2005. Developmental control of CD8 T cell-avidity maturation in autoimmune diabetes. *J Clin Invest* 115: 1879-87
42. Jiang H, Chess L. 2000. The Specific Regulation of Immune Responses by CD8+ T Cells Restricted by the MHC Class IB Molecule, QA-1. *Annu. Rev. Immunol.* 18: 185-216
43. Jiang H, Wu Y, Liang B, Zheng Z, Tang G, Kanellopoulos J, Soloski M, Winchester R, Goldstein I, Chess L. 2005. An affinity/avidity model of peripheral T cell regulation. *J Clin Invest* 115: 302-12
44. Burnet M, Fenner F. 1949. *Production of Antibodies.* Melbourne: McMillan
45. Billingham R E, Brent L, Medawar P B. 1953. Actively acquired tolerance of foreign cells. *Nature* 172: 603-6
46. Bouneaud C, Kourilsky P, Bousso P. 2000. Impact of negative selection on the T cell repertoire reactive to a self-peptide: a large fraction of T cell clones escapes clonal deletion. *Immunity* 13: 829-40
47. Sandberg J K, Franksson L, Sundback J, Michaelsson J, Petersson M, Achour A, Wallin R P, Sherman N E, Bergman T, Jornvall H, Hunt D F, Kiessling R, Karre K. 2000. T cell tolerance based on avidity thresholds rather than complete deletion allows maintenance of maximal repertoire diversity. *J Immunol* 165: 25-33
48. Lenardo M, Chan K M, Hornung F, McFarland H, Siegel R, Wang J, Zheng L. 1999. Mature T lymphocyte apoptosis—immune regulation in a dynamic and unpredictable antigenic environment [In Process Citation]. *Annu Rev Immunol* 17: 221-53
49. Durie F H, Foy T M, Masters S R, Laman J D, Noelle R J. 1994. The role of CD40 in the regulation of humoral and cell-mediated immunity. [Review]. *Immunology Today* 15: 406-11
50. Klaus S J, Pinchuk L M, Ochs H D, Law C L, Fanslow W C, Armitage R J, Clark E A. 1994. Costimulation through CD28 enhances T cell-dependent B cell activation via CD40-CD40L interaction. *J Immunol* 152: 5643-52
51. Koulova L, Clark E A, Shu G, Dupont B. 1991. The CD28 ligand B7/BB1 provides costimulatory signal for alloactivation of CD4+ T cells. *J Exp Med* 173: 759-62
52. Lenschow D J, Walunas T L, Bluestone J A. 1996. CD28/B7 system of T cell costimulation. *Annu Rev Immunol* 14: 233-58
53. Coffman R L, Mosmann T R. 1991. CD4+ T-cell subsets: regulation of differentiation and function. [Review] [14 refs]. *Res Immunol* 142: 7-9
54. Mosmann T R, Cherwinski H, Bond M W, Giedlin M A, Coffman R L. 1986. Two types of murine helper T cell clone. I. Definition according to profiles of lymphokine activities and secreted proteins. *J Immunol* 136: 2348-57
55. Mosmann T R, Coffman R L. 1989. TH1 and TH2 cells: different patterns of lymphokine secretion lead to different functional properties. *Annu Rev Immunol* 7: 145-73
56. Groux H, O'Garra A, Bigler M, Rouleau M, Antonenko S, de Vries J E, Roncarolo M G. 1997. A CD4+ T-cell subset inhibits antigen-specific T-cell responses and prevents colitis. *Nature* 389: 737-42
57. Levings M K, Roncarolo M G. 2000. T-regulatory 1 cells: a novel subset of CD4 T cells with immunoregulatory properties. *J Allergy Clin Immunol* 106: S109-12.
58. Roncarolo M G, Levings M K. 2000. The role of different subsets of T regulatory cells in controlling autoimmunity. *Curr Opin Immunol* 12: 676-83.
59. Jiang H, Chess L. 2004. An integrated view of suppressor T cell subsets in immunoregulation. *J Clin Invest* 114: 1198-208
60. Sakaguchi S, Fukuma K, Kuribayashi K, Masuda T. 1985. Organ-specific autoimmune diseases induced in mice by elimination of T cell subset. I. Evidence for the active participation of T cells in natural self-tolerance; deficit of a T cell subset as a possible cause of autoimmune disease. *J Exp Med* 161: 72-87.
61. Sakaguchi S, Sakaguchi N, Asano M, Itoh M, Toda M. 1995. Immunologic self-tolerance maintained by activated T cells expressing IL-2 receptor alpha-chains (CD25). Breakdown of a single mechanism of self-tolerance causes various autoimmune diseases. *J Immunol* 155: 1151-64.
62. Shevach E M. 2001. Certified professionals: CD4(+) CD25(+) suppressor T cells. *J Exp Med* 193: F41-6.
63. Khattri R, Cox T, Yasayko S A, Ramsdell F. 2003. An essential role for Scurfin in CD4+CD25+ T regulatory cells. *Nat Immunol* 4: 337-42.
64. Fontenot J D, Gavin M A, Rudensky A Y. 2003. Foxp3 programs the development and function of CD4+CD25+ regulatory T cells. *Nat Immunol* 4: 330-6.
65. Kretschmer K, Apostolou I, Hawiger D, Khazaie K, Nussenzweig M C, von Boehmer H. 2005. Inducing and expanding regulatory T cell populations by foreign antigen. *Nat Immunol* 6: 1219-27
66. Schubert L A, Jeffery E, Zhang Y, Ramsdell F, Ziegler S F. 2001. Scurfin (FOXP3) acts as a repressor of transcription and regulates T cell activation. *J Biol Chem* 276: 37672-9.

67. Brunkow M E, Jeffery E W, Hjerrild K A, Paeper B, Clark L B, Yasayko S A, Wilkinson J E, Galas D, Ziegler S F, Ramsdell F. 2001. Disruption of a new forkhead/winged-helix protein, scurfin, results in the fatal lymphoproliferative disorder of the scurfy mouse. *Nat Genet.* 27: 68-73.

68. von Boehmer H, Aifantis I, Gounari F, Azogui O, Haughn L, Apostolou I, Jaeckel E, Grassi F, Klein L. 2003. Thymic selection revisited: how essential is it? *Immunol Rev* 191: 62-78

69. Sakaguchi S. 2004. Naturally arising CD4+ regulatory t cells for immunologic self-tolerance and negative control of immune responses. *Annu Rev Immunol* 22: 531-62

70. Apostolou I, Sarukhan A, Klein L, von Boehmer H. 2002. Origin of regulatory T cells with known specificity for antigen. *Nat Immunol* 3: 756-63.

71. Kronenberg M, Rudensky A. 2005. Regulation of immunity by self-reactive T cells. *Nature* 435: 598-604

72. Sakaguchi S. 2005. Naturally arising Foxp3-expressing CD25+CD4+ regulatory T cells in immunological tolerance to self and non-self. *Nat Immunol* 6: 345-52

73. Fontenot J D, Rudensky A Y. 2005. A well adapted regulatory contrivance: regulatory T cell development and the forkhead family transcription factor Foxp3. *Nat Immunol* 6: 331-7

74. Jaeckel E, Kretschmer K, Apostolou I, von Boehmer H. 2006. Instruction of Treg commitment in peripheral T cells is suited to reverse autoimmunity. *Semin Immunol* 18: 89-92

75. Thornton A M, Shevach E M. 2000. Suppressor effector function of CD4+CD25+ immunoregulatory T cells is antigen nonspecific. *J Immunol* 164: 183-90.

76. Shevach E M. 2002. CD4+ CD25+ suppressor T cells: more questions than answers. *Nat Rev Immunol* 2: 389-400.

77. Apostolou I, von Boehmer H. 2004. In vivo instruction of suppressor commitment in naive T cells. *J Exp Med* 199: 1401-8

78. Hori S, Carvalho T L, Demengeot J. 2002. CD25+CD4+ regulatory T cells suppress CD4+ T cell-mediated pulmonary hyperinflammation driven by Pneumocystis carinii in immunodeficient mice. *Eur J Immunol* 32: 1282-91

79. Sakaguchi S. 2003. Control of immune responses by naturally arising CD4+ regulatory T cells that express toll-like receptors. *J Exp Med* 197: 397-401

80. Wood K J, Sakaguchi S. 2003. Regulatory T cells in transplantation tolerance. *Nat Rev Immunol* 3: 199-210.

81. Zhai Y, Kupiec-Weglinski J W. 1999. What is the role of regulatory T cells in transplantation tolerance? *Curr Opin Immunol* 11: 497-503.

82. Waldmann H, Cobbold S. 2001. Regulating the immune response to transplants. a role for CD4+ regulatory cells? *Immunity* 14: 399-406

83. Bluestone J A, Abbas A K. 2003. Natural versus adaptive regulatory T cells. *Nat Rev Immunol* 3: 253-7

84. Chen W, Jin W, Hardegen N, Lei K J, Li L, Marinos N, McGrady G, Wahl S M. 2003. Conversion of peripheral CD4+CD25− naive T cells to CD4+CD25+ regulatory T cells by TGF-beta induction of transcription factor Foxp3. *J Exp Med* 198: 1875-86.

85. Kasprowicz D J, Droin N, Soper D M, Ramsdell F, Green D R, Ziegler S F. 2005. Dynamic regulation of FoxP3 expression controls the balance between CD4(+) T cell activation and cell death. *Eur J Immunol* 35: 3424-32

86. Sakaguchi S. 2000. Regulatory T cells: key controllers of immunologic self-tolerance. *Cell* 101: 455-8.

87. von Herrath M G, Harrison L C. 2003. Antigen-induced regulatory T cells in autoimmunity. *Nat Rev Immunol* 3: 223-32

88. Bach J F. 2003. Regulatory T cells under scrutiny. *Nat Rev Immunol* 3: 189-98

89. Jiang H, Zhang S I, Pernis B. 1992. Role of CD8+ T cells in murine experimental allergic encephalomyelitis. *Science* 256: 1213-5

90. Koh D-R, Fung-Leung W-P, Ho A, Gray D, Acha-Orbea H, Mak T-W. 1992. Less Mortality but More Relapses in Experimental Allergic Encephalomyelitis in CD8−/− Mice. *Science* 256: 1210-3

91. Jiang H, Ware R, Stall A, Flaherty L, Chess L, Pernis B. 1995. Murine CD8+ T cells that specifically delete autologous CD4+ T cells expressing V beta 8 TCR: a role of the Qa-1 molecule. *Immunity* 2: 185-94

92. Jiang H, Kashleva H, Xu L X, Forman J, Flaherty L, Pernis B, Braunstein N S, Chess L. 1998. T cell vaccination induces T cell receptor Vbeta-specific Qa-1—restricted regulatory CD8(+) T cells. *Proc Natl Acad Sci USA* 95: 4533-7

93. Jiang H, Braunstein N S, Yu B, Winchester R, Chess L. 2001. CD8+ T cells control the TH phenotype of MBP-reactive CD4+ T cells in EAE mice. *Proc Natl Acad Sci USA* 98: 6301-6.

94. Hu D, Ikizawa K, Lu L, Sanchirico M E, Shinohara M L, Cantor H. 2004. Analysis of regulatory CD8 T cells in Qa-1-deficient mice. *Nat Immunol* 5: 516-23

95. Aldrich C J, Rodgers J R, Rich R R. 1988. Regulation of Qa-1 expression and determinant modification by an H-2D-linked gene, Qdm. *Immunogenetics* 28: 334-44

96. Aldrich C J, Waltrip R, Hermel E, Attaya M, Lindahl K F, Monaco J J, Forman J. 1992. T cell recognition of QA-1b antigens on cells lacking a functional Tap-2 transporter. *J Immunol* 149: 3773-7

97. Lowen L C, Aldrich C J, Forman J. 1993. Analysis of T cell receptors specific for recognition of class IB antigens. *J Immunol* 151: 6155-65

98. Kurepa Z, Hasemann C A, Forman J. 1998. Qa-1b binds conserved class I leader peptides derived from several mammalian species. *J Exp Med* 188: 973-8

99. Cotterill L A, Stauss H J, Millrain M M, Pappin D J, Rahman D, Canas B, Chandler P, Stackpoole A, Simpson E, Robinson P J, Dyson P J. 1997. Qa-1 interaction and T cell recognition of the Qa-1 determinant modifier peptide. *Eur J Immunol* 27: 2123-32

100. Imani F, Soloski M J. 1991. Heat shock proteins can regulate expression of the Tla region-encoded class Ib molecule Qa-1. *Proc Natl Acad Sci USA* 88: 10475-9

101. Chun T, Aldrich C J, Baldeon M E, Kawczynski L V, Soloski M J, Gaskins H R. 1998. Constitutive and regulated expression of the class IB molecule Qa-1 in pancreatic beta cells. *Immunology* 94: 64-71

102. Michaelsson J, Teixeira de Matos C, Achour A, Lanier L L, Karre K, Soderstrom K. 2002. A signal peptide derived from hsp60 binds HLA-E and interferes with CD94/NKG2A recognition. *J Exp Med* 196: 1403-14.

103. Jerne N K. 1974. The immune system: a web of V-domains. *Harvey Lect* 70: 93-110.

104. Dorf M E, Benacerraf B. 1984. Suppressor Cells and Immunoregulation. *Ann. Rev. Immunol.* 2: 127-58

105. Batchelor J R, Lombardi G, Lechler R I. 1989. Speculations on the specificity of suppression. *Immunol Today* 10: 37-40

106. Gammon G, Sercarz E. 1990. Does the presence of self-reactive T cells indicate the breakdown of tolerance? *Clin Immunol Immunopathol* 56: 287-97

107. Lohse A W, Mor F, Karin N, Cohen I R. 1989. Control of experimental autoimmune encephalomyelitis by T cells responding to activated T cells. *Science* 244: 820-2

108. Cohen I R, Quintana F J, Mimran A. 2004. Tregs in T cell vaccination: exploring the regulation of regulation. *J Clin Invest* 114: 1227-32

109. Kawai K, Ohashi P S. 1995. Immunological function of a defined T-cell population tolerized to low-affinity self antigens [published erratum appears in Nature 1995 Nov. 23; 378(6555):419]. *Nature* 374: 68-9

110. Goldrath A W, Bevan M J. 1999. Selecting and maintaining a diverse T-cell repertoire. *Nature* 402: 255-62

111. Garcia K C, Degano M, Pease L R, Huang M, Peterson P A, Teyton L, Wilson I A. 1998. Structural basis of plasticity in T cell receptor recognition of a self peptide-MHC antigen. *Science* 279: 1166-72

112. Anderton S M, Wraith D C. 2002. Selection and fine-tuning of the autoimmune T-cell repertoire. *Nat Rev Immunol* 2: 487-98

113. Peterson D A, DiPaolo R J, Kanagawa O, Unanue E R. 1999. Quantitative analysis of the T cell repertoire that escapes negative selection. *Immunity* 11: 453-62

114. Cook J R, Wormstall E M, Hornell T, Russell J, Connolly J M, Hansen T H. 1997. Quantitation of the cell surface level of Ld resulting in positive versus negative selection of the 2C transgenic T cell receptor in vivo. *Immunity* 7: 233-41

115. Chidgey A, Boyd R. 1997. Agonist peptide modulates T cell selection thresholds through qualitative and quantitative shifts in CD8 co-receptor expression. *Int Immunol* 9: 1527-36

116. Wang R, Nelson A, Kimachi K, Grey H M, Farr A G. 1998. The role of peptides in thymic positive selection of class II major histocompatibility complex-restricted T cells. *Proc Natl Acad Sci USA* 95: 3804-9

117. Rees W, Bender J, Teague T K, Kedl R M, Crawford F, Marrack P, Kappler J. 1999. An inverse relationship between T cell receptor affinity and antigen dose during CD4(+) T cell responses in vivo and in vitro. *Proc Natl Acad Sci USA* 96: 9781-6.

118. Nossal G J. 1994. Negative selection of lymphocytes. *Cell* 76: 229-39

119. Ignatowicz L, Kappler J, Marrack P. 1996. The repertoire of T cells shaped by a single MHC/peptide ligand. *Cell* 84: 521-9

120. Nagamine K, Peterson P, Scott H S, Kudoh J, Minoshima S, Heino M, Krohn K J, Lalioti M D, Mullis P E, Antonarakis S E, Kawasaki K, Asakawa S, Ito F, Shimizu N. 1997. Positional cloning of the APECED gene. *Nat Genet.* 17: 393-8

121. Mittaz L, Rossier C, Heino M, Peterson P, Krohn K J, Gos A, Morris M A, Kudoh J, Shimizu N, Antonarakis S E, Scott H S. 1999. Isolation and characterization of the mouse Aire gene. *Biochem Biophys Res Commun* 255: 483-90

122. Anderson M S, Venanzi E S, Klein L, Chen Z, Berzins S P, Turley S J, von Boehmer H, Bronson R, Dierich A, Benoist C, Mathis D. 2002. Projection of an immunological self shadow within the thymus by the aire protein. *Science* 298: 1395-401

123. Liston A, Gray D H, Lesage S, Fletcher A L, Wilson J, Webster K E, Scott H S, Boyd R L, Peltonen L, Goodnow C C. 2004. Gene dosage—limiting role of Aire in thymic expression, clonal deletion, and organ-specific autoimmunity. *J Exp Med* 200: 1015-26

124. Anderson M S, Venanzi E S, Chen Z, Berzins S P, Benoist C, Mathis D. 2005. The cellular mechanism of Aire control of T cell tolerance. *Immunity* 23: 227-39

125. Yagi J, Janeway C A, Jr. 1990. Ligand thresholds at different stages of T cell development. *Int Immunol* 2: 83-9

126. Buhlmann J E, Elkin S K, Sharpe A H. 2003. A role for the B7-1/B7-2:CD28/CTLA-4 pathway during negative selection. *J Immunol* 170: 5421-8

127. Foy T M, Page D M, Waldschmidt T J, Schoneveld A, Laman J D, Masters S R, Tygrett L, Ledbetter J A, Aruffo A, Claassen E, Xu J C, Flavell R A, Oehen S, Hedrick S M, Noelle R J. 1995. An essential role for gp39, the ligand for CD40, in thymic selection. *J Exp Med* 182: 1377-88

128. Hackett J, Jr., Stebbins C, Rogerson B, Davis M M, Storb U. 1992. Analysis of a T cell receptor gene as a target of the somatic hypermutation mechanism. *J Exp Med* 176: 225-31

129. Jolly C J, Wagner S D, Rada C, Klix N, Milstein C, Neuberger M S. 1996. The targeting of somatic hypermutation. *Semin Immunol* 8: 159-68

130. Wagner S D, Neuberger M S. 1996. Somatic hypermutation of immunoglobulin genes. *Annu Rev Immunol* 14: 441-57

131. Slifka M K, Whitton J L. 2001. Functional avidity maturation of CD8(+) T cells without selection of higher affinity TCR. *Nat Immunol* 2: 711-7

132. van Elsas A, Hurwitz A A, Allison J P. 1999. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. *J Exp Med* 190: 355-66

133. Hurwitz A A, Foster B A, Kwon E D, Truong T, Choi E M, Greenberg N M, Burg M B, Allison J P. 2000. Combination immunotherapy of primary prostate cancer in a transgenic mouse model using CTLA-4 blockade. *Cancer Res* 60: 2444-8

134. Hernandez J, Ko A, Sherman L A. 2001. CTLA-4 blockade enhances the CTL responses to the p53 self-tumor antigen. *J Immunol* 166: 3908-14

135. Chen Z, Benoist C, Mathis D. 2005. How defects in central tolerance impinge on a deficiency in regulatory T cells. *Proc Natl Acad Sci USA* 102: 14735-40

136. Zhao Z S, Granucci F, Yeh L, Schaffer P A, Cantor H. 1998. Molecular mimicry by herpes simplex virus-type 1: autoimmune disease after viral infection. *Science* 279: 1344-7.

137. Benoist C, Mathis D. 2001. Autoimmunity provoked by infection: how good is the case for T cell epitope mimicry? *Nat Immunol* 2: 797-801

138. Ware R, Jiang H, Braunstein N, Kent J, Wiener E, Pernis B, Chess L. 1995. Human CD8+ T lymphocyte clones specific for T cell receptor V beta families expressed on autologous CD4+ T cells. *Immunity* 2: 177-84

139. Li J, Goldstein I, Glickman-Nir E, Jiang H, Chess L. 2001. Induction of TCR Vbeta-specific CD8+ CTLs by TCR Vbeta-derived peptides bound to HLA-E. *J Immunol* 167: 3800-8.

140. Bach J F. 2002. The effect of infections on susceptibility to autoimmune and allergic diseases. *N Engl J Med* 347: 911-20

141. Tao X, Constant S, Jorritsma P, Bottomly K. 1997. Strength of TCR signal determines the costimulatory requirements for Th1 and Th2 CD4+ T cell differentiation. *J Immunol* 159: 5956-63

142. Leitenberg D, Bottomly K. 1999. Regulation of naive T cell differentiation by varying the potency of TCR signal transduction. *Semin Immunol* 11: 283-92

143. Brogdon J L, Leitenberg D, Bottomly K. 2002. The potency of TCR signaling differentially regulates NFATc/p activity and early IL-4 transcription in naive CD4+ T cells. *J Immunol* 168: 3825-32

144. Miller A T, Wilcox H M, Lai Z, Berg L J. 2004. Signaling through Itk promotes T helper 2 differentiation via negative regulation of T-bet. *Immunity* 21: 67-80

145. Martins T C, Aguas A P. 1999. A role for CD45RBlow CD38+ T cells and costimulatory pathways of T-cell activation in protection of non-obese diabetic (NOD) mice from diabetes. *Immunology* 96: 600-5.

146. Lehmann D, Ben-Nun A. 1992. Bacterial agents protect against autoimmune disease. I. Mice pre-exposed to *Bordetella pertussis* or *Mycobacterium tuberculosis* are highly refractory to induction of experimental autoimmune encephalomyelitis. *J Autoimmun* 5: 675-90

147. Hempel K, Freitag A, Freitag B, Endres B, Mai B, Liebaldt G. 1985. Unresponsiveness to experimental allergic encephalomyelitis in Lewis rats pretreated with complete Freund's adjuvant. *Int Arch Allergy Appl Immunol* 76: 193-9

148. Greenwood B M, Herrick E M, Voller A. 1970. Suppression of autoimmune disease in NZB and (NZB×NZW) F1 hybrid mice by infection with malaria. *Nature* 226: 266-7

149. Oldstone M B, Dixon F J. 1972. Inhibition of antibodies to nuclear antigen and to DNA in New Zealand mice infected with lactate dehydrogenase virus. *Science* 175: 784-6

150. Hansen G, Yeung V P, Berry G, Umetsu D T, DeKruyff R H. 2000. Vaccination with heat-killed *Listeria* as adjuvant reverses established allergen-induced airway hyperreactivity and inflammation: role of CD8+ T cells and IL-18. *J Immunol* 164: 223-30

151. Zuany-Amorim C, Manlius C, Trifilieff A, Brunet L R, Rook G, Bowen G, Pay G, Walker C. 2002. Long-term protective and antigen-specific effect of heat-killed *Mycobacterium vaccae* in a murine model of allergic pulmonary inflammation. *J Immunol* 169: 1492-9

152. Zuany-Amorim C, Sawicka E, Manlius C, Le Moine A, Brunet L R, Kemeny D M, Bowen G, Rook G, Walker C. 2002. Suppression of airway eosinophilia by killed *Mycobacterium vaccae*-induced allergen-specific regulatory T-cells. *Nat Med* 8: 625-9

153. Pardoll D. 2003. Does the immune system see tumors as foreign or self? *Annu Rev Immunol* 21: 807-39

154. Cox A L, Skipper J, Chen Y, Henderson R A, Darrow T L, Shabanowitz J, Engelhard V H, Hunt D F, Slingluff C L, Jr. 1994. Identification of a peptide recognized by five melanoma-specific human cytotoxic T cell lines. *Science* 264: 716-9

155. Slingluff C L, Jr., Hunt D F, Engelhard V H. 1994. Direct analysis of tumor-associated peptide antigens. *Curr Opin Immunol* 6: 733-40

156. Gervois N, Guilloux Y, Diez E, Jotereau F. 1996. Suboptimal activation of melanoma infiltrating lymphocytes (TIL) due to low avidity of TCR/MHC-tumor peptide interactions. *J Exp Med* 183: 2403-7

157. Slansky J E, Rattis F M, Boyd L F, Fahmy T, Jaffee E M, Schneck J P, Margulies D H, Pardoll D M. 2000. Enhanced antigen-specific antitumor immunity with altered peptide ligands that stabilize the MHC-peptide-TCR complex. *Immunity* 13: 529-38

158. Braud, V., E. Y. Jones, and A. McMichael. 1997. The human major histocompatibility complex class Ib molecule HLA-E binds signal sequence-derived peptides with primary anchor residues at positions 2 and 9. Eur J Immunol 27:1164.

159. Kraft, J. R., R. E. Vance, J. Pohl, A. M. Martin, D. H. Raulet, and P. E. Jensen. 2000. Analysis of Qa-1(b) peptide binding specificity and the capacity of CD94/NKG2A to discriminate between Qa-1-peptide complexes. J Exp Med 192:613.

160. Bond, J. S., and P. E. Butler. 1987. Intracellular proteases. Annu Rev Biochem 56:333.

161. Chaput, N., N. E. Schartz, F. Andre, J. Taieb, S. Novault, P. Bonnaventure, N. Aubert, J. Bernard, F. Lemonnier, M. Merad, G. Adema, M. Adams, M. Ferrantini, A. F. Carpentier, B. Escudier, T. Tursz, E. Angevin, and L. Zitvogel. 2004. Exosomes as potent cell-free peptide-based vaccine. II. Exosomes in CpG adjuvants efficiently prime naive Tc1 lymphocytes leading to tumor rejection. J Immunol 172: 2137.

162. Dal Porto, J., T. E. Johansen, B. Catipovic, D. J. Parfiit, D. Tuveson, U. Gether, S. Kozlowski, D. T. Fearon, and J. P. Schneck. 1993. A soluble divalent class I major histocompatibility complex molecule inhibits alloreactive T cells at nanomolar concentrations. Proc Natl Acad Sci USA 90:6671.

163. Oelke, M., and J. P. Schneck. 2004. HLA-Ig-based artificial antigen-presenting cells: setting the terms of engagement. Clin Immunol 110:243.

164. Casares, S., C. A. Bona, and T. D. Brumeanu. 1997. Engineering and characterization of a murine MHC class II-immunoglobulin chimera expressing an immunodominant CD4 T viral epitope. Protein Eng 10:1295.

165. Malherbe, L., C. Filippi, V. Julia, G. Foucras, M. Moro, H. Appel, K. Wucherpfennig, J. C. Guery, and N. Glaichenhaus. 2000. Selective activation and expansion of high-affinity CD4+ T cells in resistant mice upon infection with *Leishmania major*. Immunity 13:771.

166. Casares, S., C. A. Bona, and T. D. Brumeanu. 2001. Enzymatically mediated engineering of multivalent MHC class II-peptide chimeras. Protein Eng 14:195.

167. Altman, J. D., P. A. Moss, P. J. Goulder, D. H. Barouch, M. G. McHeyzer-Williams, J. I. Bell, A. J. McMichael, and M. M. Davis. 1996. Phenotypic analysis of antigen-specific T lymphocytes. Science 274:94.

168. Michaelsson, J., C. Teixeira de Matos, A. Achour, L. L. Lanier, K. Karre, and K. Soderstrom. 2002. A signal peptide derived from hsp60 binds HLA-E and interferes with CD94/NKG2A recognition. J Exp Med 196:1403.

169. Sanderson, S., and N. Shastri. 1994. LacZ inducible, antigen/MHC-specific T cell hybrids. International Immunology 6:369.

170. Bank, I., M. Hemler, M. B. Brenner, D. Cohen, V. Levy, J. Belko, C. Crouse, and L. Chess. 1989. A novel monoclonal antibody, 1B3.1, binds to a new epitope of the VLA-1 molecule. Cell Immunol 122:416.

171. Lederman, S., M. J. Yellin, A. Krichevsky, J. Belko, J. J. Lee, and L. Chess. 1992. Identification of a novel surface protein on activated CD4+ T cells that induces contact-dependent B cell differentiation (help). J Exp Med 175: 1091.

172. Chen, W., Zhang, L., Liang, B., Saenger, Y., Li, J., Ches, L., and Jiang, H. 2007. Perceiving the Avidity of T Cell Activation Can Be Translated into Peripheral T Cell Regulation. Proc Natl Acad Sci USA 104:20472-20477.

173. Liu, E., Moriyama, H., Abiru, N., Paronen, J., Devendra, D., Finkelman, F. D., and Eisenbarth, G. S. 2004. Prevent- 173. ing peptide-induced anaphylaxis: addition of C-terminal amino acids to produce a neutral isoelectric point. J Allergy Clin Immunol 114:607-613.
174. Elias, D., Marcus, H., Reshef, T., Ablamunits, V., and Cohen, I. R. 1995. Induction of diabetes in standard mice by immunization with the p277 peptide of a 60-kDa heat shock protein. Eur J Immunol 25:2851-2857.
175. Elias, D., Meilin, A., Ablamunits, V., Birk, O. S., Carmi, P., Konen-Waisman, S., and Cohen, I. R. 1997. Hsp60 peptide therapy of NOD mouse diabetes induces a Th2 cytokine burst and downregulates autoimmunity to various beta-cell antigens. Diabetes 46:758-764.
176. Aldrich, C. J., DeClousc, A., Woods, A. S., Cotter, R. J., Woloski, M. J., and Forman, J. 1994. Identification of a TAP-dependent header peptide recognized by alloreactive T cells specific for a Class I-b antigen. Cell 79:649-659.
177. Gays, F., Fraser, K. P., Toomey, J. A., Diamond, A. G., Millrain, M. M., Dyson, P. J., and Brooks, C. G. 2001. Functional analysis of the molecular factors controlling Qa1-mediated protection of target cells from NK lysis. J Immunol 166:1601-1610.
178. Cohn, M. 2004. Whither T-suppressors: if they didn't exist would we have to invent them? Cell Immunol 227: 81-92.
179. Jiang, H., Zhang, S. I., and Pernis, B. 1992. Role of CD8+ T cells in murine experimental allergic encephalomyelitis. Science 256:1213-1215.
180. Lohse, A. W., Mor, F., Karin, N., and Cohen, I. R. 1989. Control of experimental autoimmune encephalomyelitis by T cells responding to activated T cells. Science 244:820-822.
181. Cohen, I. R., Quintana, F. J., and Mimran, A. 2004. Tregs in T cell vaccination: exploring the regulation of regulation. J Clin Invest 114:1227-1232.
182. Sakaguchi, S. 2004. Naturally arising CD4+ regulatory T cells for immunologic self-tolerance and negative control of immune responses. Annu Rev Immunol 22:531-562.
183. Fasso, M., Anandasabapathy, N., Crawford, F., Kappler, J., Fathman, C. G., and Ridgway, W. M. 2000. T cell receptor (TCR)-mediated repertoire selection and loss of TCR vbeta diversity during the initiation of a CD4(+) T cell response in vivo. J Exp Med 192:1719-1730.
184. Targoni, O. S., and Lehmann, P. V. 1998. Endogenous myelin basic protein inactivates the high avidity T cell repertoire. J Exp Med 187:2055-2063.

---

What is claimed:

1. A composition comprising a dendritic cell loaded extracellularly with Hsp60sp peptide, wherein the dendritic cell is first cultured in vitro and is then loaded with the Hsp60sp peptide in vitro, and wherein the Hsp60sp peptide consists of the amino acid sequence set forth in SEQ ID NO: 2.

2. The composition of claim 1, wherein the dendritic cell is an autologous dendritic cell.

* * * * *

UNITED STATES PATENT AND TRADEMARK OFFICE
CERTIFICATE OF CORRECTION

PATENT NO. : 9,421,249 B2
APPLICATION NO. : 13/762249
DATED : August 23, 2016
INVENTOR(S) : Jiang et al.

Page 1 of 1

It is certified that error appears in the above-identified patent and that said Letters Patent is hereby corrected as shown below:

In the Specification

Column 1, Lines 15 - 19, should read:
"This invention was made with government support under AI039630, AI039675, AI065609, AI044927, and AI046132 awarded by the National Institutes of Health. The government has certain rights in the invention."

Signed and Sealed this
Twenty-ninth Day of August, 2023

Katherine Kelly Vidal
*Director of the United States Patent and Trademark Office*